US009216065B2

(12) United States Patent
Cohen et al.

(10) Patent No.: US 9,216,065 B2
(45) Date of Patent: Dec. 22, 2015

(54) FORMING AND DISPLAYING A COMPOSITE IMAGE

(75) Inventors: Ran Cohen, Petah Tikva (IL); Zohar Barzelay, Haifa (IL); Eldad Klaiman, Haifa (IL); Alexander Steinberg, Ra'anana (IL)

(73) Assignee: SYNC-RX, LTD., Netanya (IL)

( * ) Notice: Subject to any disclaimer, the term of this patent is extended or adjusted under 35 U.S.C. 154(b) by 148 days.

(21) Appl. No.: 12/781,366

(22) Filed: May 17, 2010

(65) Prior Publication Data

US 2010/0222671 A1 Sep. 2, 2010

Related U.S. Application Data

(63) Continuation-in-part of application No. 12/666,879, filed as application No. PCT/IL2009/001089 on Nov. 18, 2009, now Pat. No. 8,781,193, which is a continuation-in-part of application No. 12/075,244, (Continued)

(51) Int. Cl.
*A61B 5/05* (2006.01)
*A61B 19/00* (2006.01)

(Continued)

(52) U.S. Cl.
CPC ............. *A61B 19/50* (2013.01); *A61B 5/0044* (2013.01); *A61B 6/12* (2013.01); *A61B 6/469* (2013.01); *A61B 6/481* (2013.01); *A61B 6/501* (2013.01); *A61B 6/504* (2013.01); *A61B 6/5217* (2013.01);

(Continued)

(58) Field of Classification Search
USPC ......... 600/407, 416, 423, 425, 433, 437, 443, 600/466, 467; 382/128, 278, 285, 294
See application file for complete search history.

(56) References Cited

U.S. PATENT DOCUMENTS

| 3,871,360 A | 3/1975 | Van Horn et al. |
| 3,954,098 A | 5/1976 | Dick et al. |

(Continued)

FOREIGN PATENT DOCUMENTS

| EP | 2 570 079 A1 | 3/2013 |
| WO | WO 94/10904 | 5/1994 |

(Continued)

OTHER PUBLICATIONS

International Search Report dated Mar. 2, 2012, issued in PCT/IL11/00612.

(Continued)

*Primary Examiner* — Unsu Jung
*Assistant Examiner* — Michael N Fisher
(74) *Attorney, Agent, or Firm* — Sughrue Mion, PLLC

(57) ABSTRACT

Apparatus and methods are described including acquiring a plurality of image frames of a portion of a subject's body. At least one of the image frames is designated as a baseline image frame, a shape of the portion in the first baseline image frame being designated as a baseline shape. A non-baseline-shape image frame is deformed, such that the shape of the portion becomes more similar to the baseline shape of the portion than when the portion in the non-baseline-shape image frame is not deformed. A composite image is formed that is of higher clarity with respect to anatomy of the portion, relative to each of the acquired image frames, by averaging at least the deformed non-baseline-shape image frame with the baseline image frame. The composite image is displayed on a display. Other applications are also described.

6 Claims, 31 Drawing Sheets

Related U.S. Application Data filed on Mar. 10, 2008, now abandoned, which is a continuation-in-part of application No. 12/075,214, filed on Mar. 10, 2008, now abandoned, and a continuation-in-part of application No. 12/075,252, filed on Mar. 10, 2008.

(60) Provisional application No. 61/193,329, filed on Nov. 18, 2008, provisional application No. 61/193,915, filed on Jan. 8, 2009, provisional application No. 61/202,181, filed on Feb. 4, 2009, provisional application No. 61/202,451, filed on Mar. 2, 2009, provisional application No. 61/213,216, filed on May 18, 2009, provisional application No. 61/213,534, filed on Jun. 17, 2009, provisional application No. 61/272,210, filed on Sep. 1, 2009, provisional application No. 61/272,356, filed on Sep. 16, 2009, provisional application No. 60/906,091, filed on Mar. 8, 2007, provisional application No. 60/924,609, filed on May 22, 2007, provisional application No. 60/929,165, filed on Jun. 15, 2007, provisional application No. 60/935,914, filed on Sep. 6, 2007, provisional application No. 60/996,746, filed on Dec. 4, 2007.

(51) Int. Cl.

| | |
|---|---|
| *A61B 6/12* | (2006.01) |
| *A61B 6/00* | (2006.01) |
| *G06K 9/00* | (2006.01) |
| *G06T 7/00* | (2006.01) |
| *A61B 17/12* | (2006.01) |
| *G06T 7/20* | (2006.01) |
| *G06T 7/60* | (2006.01) |
| *G06T 11/60* | (2006.01) |
| *G06T 5/00* | (2006.01) |
| *A61B 5/00* | (2006.01) |
| *A61B 8/08* | (2006.01) |
| *A61B 8/00* | (2006.01) |
| *A61B 17/00* | (2006.01) |
| *A61B 17/22* | (2006.01) |
| *A61F 2/958* | (2013.01) |
| *A61B 18/02* | (2006.01) |
| *A61B 18/14* | (2006.01) |
| *A61B 18/24* | (2006.01) |

(52) U.S. Cl.
CPC .............. *A61B 6/541* (2013.01); *A61B 17/1204* (2013.01); *A61B 17/12036* (2013.01); *A61B 17/12136* (2013.01); *A61B 19/5244* (2013.01); *G06K 9/00369* (2013.01); *G06T 5/001* (2013.01); *G06T 7/0012* (2013.01); *G06T 7/0014* (2013.01); *G06T 7/0022* (2013.01); *G06T 7/0079* (2013.01); *G06T 7/0085* (2013.01); *G06T 7/2033* (2013.01); *G06T 7/602* (2013.01); *G06T 11/60* (2013.01); *A61B 5/7285* (2013.01); *A61B 5/7289* (2013.01); *A61B 6/503* (2013.01); *A61B 6/5247* (2013.01); *A61B 8/0883* (2013.01); *A61B 8/0891* (2013.01); *A61B 8/543* (2013.01); *A61B 18/02* (2013.01); *A61B 18/1492* (2013.01); *A61B 18/24* (2013.01); *A61B 19/56* (2013.01); *A61B 2017/00252* (2013.01); *A61B 2017/00694* (2013.01); *A61B 2017/00703* (2013.01); *A61B 2017/1205* (2013.01); *A61B 2017/22044* (2013.01); *A61B 2017/22094* (2013.01); *A61B 2019/505* (2013.01); *A61B 2019/507* (2013.01); *A61B 2019/5291* (2013.01); *A61B 2019/564* (2013.01); *A61F 2/958* (2013.01); *G06K 2209/057* (2013.01); *G06T 2207/10121* (2013.01); *G06T 2207/30048* (2013.01); *G06T 2207/30101* (2013.01)

(56) References Cited

U.S. PATENT DOCUMENTS

| | | |
|---|---|---|
| 4,016,871 A | 4/1977 | Schiff |
| 4,031,884 A | 6/1977 | Henzel |
| 4,245,647 A | 1/1981 | Randall |
| 4,270,143 A | 5/1981 | Morris |
| 4,316,218 A | 2/1982 | Gay |
| 4,382,184 A | 5/1983 | Wernikoff |
| 4,545,390 A | 10/1985 | Leary |
| 4,709,385 A | 11/1987 | Pfeiler |
| 4,712,560 A | 12/1987 | Schaefer et al. |
| 4,723,938 A | 2/1988 | Goodin et al. |
| 4,741,328 A | 5/1988 | Gabbay |
| 4,758,223 A | 7/1988 | Rydell |
| 4,770,184 A | 9/1988 | Greene, Jr. et al. |
| 4,849,906 A | 7/1989 | Chodos et al. |
| 4,865,043 A | 9/1989 | Shimoni |
| 4,878,115 A | 10/1989 | Elion |
| 4,920,413 A | 4/1990 | Nakamura |
| 4,991,589 A | 2/1991 | Hongo et al. |
| 4,994,965 A | 2/1991 | Crawford et al. |
| 5,020,516 A | 6/1991 | Biondi |
| 5,054,045 A | 10/1991 | Whiting et al. |
| 5,054,492 A | 10/1991 | Scribner |
| 5,056,524 A | 10/1991 | Oe |
| 5,062,056 A | 10/1991 | Lo et al. |
| 5,150,292 A | 9/1992 | Hoffmann et al. |
| 5,176,619 A | 1/1993 | Segalowitz |
| 5,177,796 A * | 1/1993 | Feig et al. .................. 382/236 |
| 5,293,574 A | 3/1994 | Roehm et al. |
| 5,295,486 A | 3/1994 | Wollschlager et al. |
| 5,330,496 A | 7/1994 | Alferness |
| 5,357,550 A | 10/1994 | Asahina et al. |
| 5,429,144 A | 7/1995 | Wilk |
| 5,457,728 A | 10/1995 | Whiting et al. |
| 5,457,754 A | 10/1995 | Han et al. |
| 5,486,192 A | 1/1996 | Walinsky et al. |
| 5,537,490 A | 7/1996 | Yukawa |
| 5,538,494 A | 7/1996 | Matsuda |
| 5,577,502 A | 11/1996 | Darrow et al. |
| 5,586,201 A | 12/1996 | Whiting et al. |
| 5,596,990 A | 1/1997 | Yock |
| 5,613,492 A | 3/1997 | Feinberg |
| 5,619,995 A | 4/1997 | Lobodzinski |
| 5,630,414 A | 5/1997 | Horbaschek |
| 5,674,217 A | 10/1997 | Wahlstrom et al. |
| 5,724,977 A | 3/1998 | Yock |
| 5,764,723 A | 6/1998 | Weinberger |
| 5,766,208 A | 6/1998 | McEwan |
| 5,792,157 A | 8/1998 | Mische et al. |
| 5,807,327 A | 9/1998 | Green et al. |
| 5,809,105 A | 9/1998 | Roehm et al. |
| 5,822,391 A | 10/1998 | Whiting et al. |
| 5,830,222 A | 11/1998 | Makower |
| 5,879,305 A | 3/1999 | Yock |
| 5,885,218 A | 3/1999 | Teo |
| 5,885,244 A | 3/1999 | Leone et al. |
| 5,916,194 A | 6/1999 | Jacobsen et al. |
| 5,921,934 A | 7/1999 | Teo |
| 5,971,976 A | 10/1999 | Wang et al. |
| 6,088,488 A | 7/2000 | Hardy et al. |
| 6,095,976 A | 8/2000 | Nachtomy |
| 6,120,455 A | 9/2000 | Teo |
| 6,120,523 A | 9/2000 | Crocker et al. |
| 6,126,608 A | 10/2000 | Kemme et al. |
| 6,148,095 A | 11/2000 | Prause et al. |
| 6,152,878 A | 11/2000 | Nachtomy |
| 6,195,445 B1 | 2/2001 | Dubuisson-Jolly et al. |
| 6,233,478 B1 | 5/2001 | Liu |
| 6,246,898 B1 | 6/2001 | Vesely et al. |
| 6,254,541 B1 | 7/2001 | Teo |

(56) References Cited

U.S. PATENT DOCUMENTS

| | | | |
|---|---|---|---|
| 6,267,727 B1 | 7/2001 | Teo |
| 6,278,767 B1 | 8/2001 | Hsieh |
| 6,331,181 B1 | 12/2001 | Tierney et al. |
| 6,370,417 B1 | 4/2002 | Horbaschek et al. |
| 6,377,011 B1 | 4/2002 | Ben-Ur |
| 6,442,415 B1 | 8/2002 | Bis et al. |
| 6,454,715 B2 | 9/2002 | Teo |
| 6,454,776 B1 | 9/2002 | Tajima et al. |
| 6,473,635 B1 | 10/2002 | Rasche |
| 6,491,636 B2 | 12/2002 | Chenal |
| 6,493,575 B1 | 12/2002 | Kesten et al. |
| 6,496,716 B1 | 12/2002 | Langer et al. |
| 6,532,380 B1 | 3/2003 | Close et al. |
| 6,538,634 B1 | 3/2003 | Chui et al. |
| 6,546,271 B1 | 4/2003 | Reisfeld |
| 6,576,007 B2 | 6/2003 | Dehdashtian et al. |
| 6,589,176 B2 | 7/2003 | Jago |
| 6,616,596 B1 | 9/2003 | Milbocker |
| 6,643,533 B2 | 11/2003 | Knoplioch |
| 6,659,953 B1 * | 12/2003 | Sumanaweera et al. ........ 600/443 |
| 6,666,863 B2 | 12/2003 | Wentzel et al. |
| 6,704,593 B2 | 3/2004 | Stainsby |
| 6,708,052 B1 | 3/2004 | Mao et al. |
| 6,711,436 B1 | 3/2004 | Duhaylongsod |
| 6,718,055 B1 | 4/2004 | Suri |
| 6,726,675 B1 | 4/2004 | Beyar |
| 6,728,566 B1 | 4/2004 | Subramanyan |
| 6,731,973 B2 | 5/2004 | Voith |
| 6,786,896 B1 | 9/2004 | Madhani et al. |
| 6,788,827 B1 | 9/2004 | Makram-Ebeid |
| 6,796,972 B1 | 9/2004 | Sinofsky et al. |
| 6,835,177 B2 | 12/2004 | Fritz et al. |
| 6,858,003 B2 | 2/2005 | Evans et al. |
| 6,912,471 B2 | 6/2005 | Heigl |
| 6,937,696 B1 | 8/2005 | Mostafavi |
| 6,959,266 B1 | 10/2005 | Mostafavi |
| 6,973,202 B2 | 12/2005 | Mostafavi |
| 6,980,675 B2 | 12/2005 | Evron et al. |
| 6,996,430 B1 | 2/2006 | Gilboa et al. |
| 6,999,852 B2 | 2/2006 | Green |
| 7,031,504 B1 | 4/2006 | Argiro et al. |
| 7,070,555 B2 | 7/2006 | Siess |
| 7,085,342 B2 | 8/2006 | Younis et al. |
| 7,134,994 B2 | 11/2006 | Alpert |
| 7,155,046 B2 | 12/2006 | Aben et al. |
| 7,155,315 B2 | 12/2006 | Niemeyer et al. |
| 7,180,976 B2 | 2/2007 | Wink et al. |
| 7,191,100 B2 | 3/2007 | Mostafavi |
| 7,209,779 B2 | 4/2007 | Kaufman |
| 7,215,802 B2 | 5/2007 | Klingensmith |
| 7,221,973 B2 | 5/2007 | Nitz |
| 7,269,457 B2 | 9/2007 | Shafer |
| 7,289,652 B2 | 10/2007 | Florent et al. |
| 7,321,677 B2 | 1/2008 | Evron et al. |
| 7,339,585 B2 | 3/2008 | Verstraelen et al. |
| 7,343,032 B2 | 3/2008 | Oakley et al. |
| 7,343,195 B2 | 3/2008 | Strommer et al. |
| 7,359,554 B2 | 4/2008 | Klingensmith |
| 7,369,691 B2 | 5/2008 | Kondo et al. |
| 7,397,935 B2 | 7/2008 | Kimmel |
| 7,398,116 B2 | 7/2008 | Edwards |
| 7,517,318 B2 | 4/2009 | Altmann |
| 7,546,154 B2 | 6/2009 | Hornegger et al. |
| 7,587,074 B2 | 9/2009 | Zarkh et al. |
| 7,599,730 B2 | 10/2009 | Hunter |
| 7,604,601 B2 | 10/2009 | Altmann |
| 7,653,426 B2 | 1/2010 | Yatsuo et al. |
| 7,668,362 B2 | 2/2010 | Olson et al. |
| 7,693,349 B2 | 4/2010 | Gering |
| 7,697,974 B2 | 4/2010 | Jenkins |
| 7,713,210 B2 | 5/2010 | Byrd |
| 7,729,743 B2 * | 6/2010 | Sabczynski et al. ......... 600/424 |
| 7,729,746 B2 | 6/2010 | Redel et al. |
| 7,740,584 B2 | 6/2010 | Donaldson |
| 7,742,629 B2 | 6/2010 | Zarkh et al. |
| 7,773,787 B2 | 8/2010 | Tek et al. |
| 7,773,792 B2 | 8/2010 | Kimmel |
| 7,778,488 B2 | 8/2010 | Nord |
| 7,778,688 B2 | 8/2010 | Strommer |
| 7,822,291 B2 | 10/2010 | Guetter |
| 7,831,076 B2 | 11/2010 | Altmann |
| 7,844,126 B2 | 11/2010 | Mory et al. |
| 7,848,553 B2 | 12/2010 | Hertel |
| 7,877,132 B2 | 1/2011 | Rongen |
| 7,889,905 B2 | 2/2011 | Higgins et al. |
| 7,892,177 B2 | 2/2011 | Rold et al. |
| 7,914,442 B1 | 3/2011 | Gazdzinski |
| 7,916,912 B2 | 3/2011 | Abramov et al. |
| 7,925,064 B2 | 4/2011 | Cloutier et al. |
| 7,925,069 B2 | 4/2011 | Ortyn et al. |
| 7,925,327 B2 | 4/2011 | Weese |
| 7,927,275 B2 | 4/2011 | Kuban |
| 7,930,014 B2 | 4/2011 | Huennekens et al. |
| 7,935,055 B2 | 5/2011 | Burckhardt |
| 7,961,926 B2 | 6/2011 | Viswanathan |
| 7,965,905 B2 | 6/2011 | Allon et al. |
| 7,970,187 B2 | 6/2011 | Puts |
| 7,978,916 B2 | 7/2011 | Klingensmith |
| 7,992,100 B2 | 8/2011 | Lundstrom |
| 8,025,622 B2 | 9/2011 | Rold et al. |
| 8,029,447 B2 | 10/2011 | Kanz |
| 8,050,474 B2 | 11/2011 | Baumgart |
| 8,052,605 B2 | 11/2011 | Muller |
| 8,055,327 B2 | 11/2011 | Strommer et al. |
| 8,077,939 B2 | 12/2011 | Le Nezet et al. |
| 8,086,000 B2 | 12/2011 | Weijers |
| 8,126,241 B2 | 2/2012 | Zarkh et al. |
| 8,155,411 B2 | 4/2012 | Hof |
| 8,157,742 B2 | 4/2012 | Taylor |
| 8,165,361 B2 | 4/2012 | Li |
| 8,172,763 B2 | 5/2012 | Nelson |
| 8,189,886 B2 | 5/2012 | Huo et al. |
| 8,199,981 B2 | 6/2012 | Koptenko et al. |
| 8,200,040 B2 | 6/2012 | Pfister |
| 8,208,995 B2 | 6/2012 | Tearney et al. |
| 8,213,676 B2 | 7/2012 | Bendall |
| 8,233,718 B2 | 7/2012 | Klingensmith |
| 8,260,395 B2 | 9/2012 | Markowitz et al. |
| 8,271,068 B2 | 9/2012 | Khamene |
| 8,275,201 B2 | 9/2012 | Rangwala et al. |
| 8,289,284 B2 | 10/2012 | Glynn |
| 8,295,577 B2 | 10/2012 | Zarkh et al. |
| 8,298,147 B2 | 10/2012 | Huennekens |
| 8,303,503 B2 | 11/2012 | Nair |
| 8,364,242 B2 | 1/2013 | Li |
| 8,396,276 B2 | 3/2013 | Gatta |
| 8,396,533 B2 | 3/2013 | Barbu et al. |
| 8,409,098 B2 | 4/2013 | Olson |
| 8,411,927 B2 | 4/2013 | Chang et al. |
| 8,428,318 B2 | 4/2013 | Zhuo |
| 8,428,691 B2 | 4/2013 | Byrd |
| 8,433,115 B2 | 4/2013 | Chen |
| 8,457,374 B2 | 6/2013 | Lendl |
| 8,478,387 B2 | 7/2013 | Xu |
| 8,483,488 B2 | 7/2013 | Richter |
| 8,515,146 B2 | 8/2013 | Zhu et al. |
| 8,565,859 B2 | 10/2013 | Wang et al. |
| 8,605,976 B2 | 12/2013 | Diamant et al. |
| 8,625,865 B2 | 1/2014 | Zarkh et al. |
| 8,700,128 B2 | 4/2014 | Assis et al. |
| 8,731,642 B2 | 5/2014 | Zarkh et al. |
| 8,861,830 B2 | 10/2014 | Brada et al. |
| 2001/0031919 A1 | 10/2001 | Strommer et al. |
| 2001/0055418 A1 | 12/2001 | Nakamura |
| 2002/0049375 A1 * | 4/2002 | Strommer et al. ............. 600/407 |
| 2002/0058869 A1 * | 5/2002 | Axelsson et al. ............. 600/423 |
| 2002/0090119 A1 | 7/2002 | Saito et al. |
| 2002/0114497 A1 | 8/2002 | Wetzel et al. |
| 2002/0188307 A1 | 12/2002 | Pintor et al. |
| 2003/0014100 A1 | 1/2003 | Maria Meens et al. |
| 2003/0018251 A1 | 1/2003 | Solomon |
| 2003/0021381 A1 | 1/2003 | Koppe et al. |
| 2003/0023141 A1 | 1/2003 | Stelzer et al. |
| 2003/0069499 A1 | 4/2003 | Lienard et al. |

(56) References Cited

U.S. PATENT DOCUMENTS

| | | |
|---|---|---|
| 2003/0088179 A1 | 5/2003 | Seeley et al. |
| 2003/0095710 A1 | 5/2003 | Tessadro |
| 2003/0139772 A1 | 7/2003 | Fisher et al. |
| 2003/0157037 A1 | 8/2003 | Perrit et al. |
| 2003/0157073 A1 | 8/2003 | Peritt et al. |
| 2004/0034380 A1 | 2/2004 | Woolfson et al. |
| 2004/0077941 A1 | 4/2004 | Reddy et al. |
| 2004/0097805 A1 | 5/2004 | Verard et al. |
| 2004/0133129 A1 | 7/2004 | Harari et al. |
| 2004/0165756 A1 | 8/2004 | Mielekamp |
| 2004/0176681 A1 | 9/2004 | Mao et al. |
| 2004/0215235 A1 | 10/2004 | Jackson et al. |
| 2004/0249270 A1 | 12/2004 | Kondo et al. |
| 2004/0254570 A1 | 12/2004 | Hadjicostis et al. |
| 2004/0267113 A1 | 12/2004 | Thomson |
| 2005/0004503 A1 | 1/2005 | Samson et al. |
| 2005/0008210 A1 | 1/2005 | Evron et al. |
| 2005/0015009 A1 | 1/2005 | Mourad et al. |
| 2005/0031176 A1 | 2/2005 | Hertel |
| 2005/0033199 A1 | 2/2005 | van der Steen et al. |
| 2005/0043614 A1 | 2/2005 | Huizenga et al. |
| 2005/0054916 A1 | 3/2005 | Mostafavi |
| 2005/0067568 A1 | 3/2005 | Harding et al. |
| 2005/0080336 A1 | 4/2005 | Byrd et al. |
| 2005/0090737 A1 | 4/2005 | Burrel et al. |
| 2005/0096589 A1 | 5/2005 | Shachar |
| 2005/0107688 A1 | 5/2005 | Strommer |
| 2005/0107808 A1* | 5/2005 | Evans et al. .............. 606/139 |
| 2005/0111719 A1 | 5/2005 | Pescatore et al. |
| 2005/0113685 A1 | 5/2005 | Maschke et al. |
| 2005/0137661 A1 | 6/2005 | Sra |
| 2005/0141766 A1 | 6/2005 | Nagahashi et al. |
| 2005/0143777 A1 | 6/2005 | Sra |
| 2005/0154281 A1* | 7/2005 | Xue et al. .................. 600/407 |
| 2005/0182295 A1 | 8/2005 | Soper et al. |
| 2005/0197557 A1 | 9/2005 | Strommer et al. |
| 2005/0197559 A1 | 9/2005 | Boese et al. |
| 2005/0197566 A1 | 9/2005 | Strommer et al. |
| 2005/0201510 A1 | 9/2005 | Mostafavi |
| 2005/0228359 A1* | 10/2005 | Doyle .......................... 604/509 |
| 2005/0234331 A1 | 10/2005 | Sendai |
| 2005/0273050 A1 | 12/2005 | Yokoyama et al. |
| 2005/0288577 A1 | 12/2005 | Weese |
| 2006/0007188 A1 | 1/2006 | Reiner |
| 2006/0058647 A1* | 3/2006 | Strommer et al. .......... 600/434 |
| 2006/0074285 A1 | 4/2006 | Zarkh et al. |
| 2006/0106318 A1 | 5/2006 | Davidson |
| 2006/0120581 A1 | 6/2006 | Eck et al. |
| 2006/0129142 A1 | 6/2006 | Reynolds |
| 2006/0147897 A1 | 7/2006 | Grinvald |
| 2006/0149134 A1 | 7/2006 | Soper et al. |
| 2006/0155327 A1 | 7/2006 | Briganti et al. |
| 2006/0159318 A1 | 7/2006 | Alyassin et al. |
| 2006/0165270 A1 | 7/2006 | Borgert et al. |
| 2006/0173287 A1* | 8/2006 | Sabczynski et al. ........ 600/424 |
| 2006/0184016 A1 | 8/2006 | Glossop |
| 2006/0188135 A1 | 8/2006 | Zarkh et al. |
| 2006/0193505 A1 | 8/2006 | Glukhovsky et al. |
| 2006/0224188 A1 | 10/2006 | Libbus et al. |
| 2006/0224232 A1 | 10/2006 | Chobotov |
| 2006/0241369 A1 | 10/2006 | Lienard et al. |
| 2006/0241445 A1 | 10/2006 | Altmann |
| 2006/0241465 A1 | 10/2006 | Huennekens et al. |
| 2006/0241478 A1 | 10/2006 | Lewis |
| 2006/0253024 A1 | 11/2006 | Altmann |
| 2006/0253029 A1 | 11/2006 | Altmann |
| 2006/0253031 A1 | 11/2006 | Altmann |
| 2006/0257006 A1 | 11/2006 | Bredno et al. |
| 2006/0259137 A1 | 11/2006 | Artof et al. |
| 2006/0269108 A1 | 11/2006 | Viswanathan |
| 2006/0287595 A1 | 12/2006 | Maschke |
| 2007/0021816 A1 | 1/2007 | Rudin |
| 2007/0038061 A1 | 2/2007 | Huennekens et al. |
| 2007/0038081 A1 | 2/2007 | Eck et al. |
| 2007/0043292 A1 | 2/2007 | Camus |
| 2007/0053558 A1 | 3/2007 | Puts et al. |
| 2007/0055128 A1 | 3/2007 | Glossop |
| 2007/0060798 A1 | 3/2007 | Krupnik et al. |
| 2007/0088431 A1 | 4/2007 | Bourang et al. |
| 2007/0106146 A1 | 5/2007 | Altmann et al. |
| 2007/0116342 A1 | 5/2007 | Zarkh et al. |
| 2007/0123771 A1 | 5/2007 | Redel et al. |
| 2007/0142907 A1 | 6/2007 | Moaddeb et al. |
| 2007/0147706 A1 | 6/2007 | Sasaki et al. |
| 2007/0165916 A1 | 7/2007 | Cloutier et al. |
| 2007/0173861 A1 | 7/2007 | Strommer |
| 2007/0208388 A1 | 9/2007 | Jahns |
| 2007/0219630 A1 | 9/2007 | Chu |
| 2007/0232896 A1 | 10/2007 | Gilboa et al. |
| 2007/0248253 A1 | 10/2007 | Manzke et al. |
| 2007/0255139 A1 | 11/2007 | Deschinger |
| 2007/0269135 A1 | 11/2007 | Ono |
| 2007/0276216 A1 | 11/2007 | Beyar et al. |
| 2008/0008366 A1 | 1/2008 | Desh |
| 2008/0015677 A1 | 1/2008 | Glossop et al. |
| 2008/0021331 A1 | 1/2008 | Grinvald |
| 2008/0082049 A1 | 4/2008 | Evans et al. |
| 2008/0089566 A1 | 4/2008 | Node-Langlois |
| 2008/0114238 A1 | 5/2008 | Lloyd |
| 2008/0118117 A1 | 5/2008 | Gauldie et al. |
| 2008/0119922 A1 | 5/2008 | Alkhatib |
| 2008/0137923 A1 | 6/2008 | Spahn |
| 2008/0137935 A1 | 6/2008 | Spahn |
| 2008/0146923 A1 | 6/2008 | Mejia |
| 2008/0146942 A1 | 6/2008 | Dala-Krishna |
| 2008/0177183 A1 | 7/2008 | Courtney |
| 2008/0188739 A1 | 8/2008 | Rongen et al. |
| 2008/0221439 A1 | 9/2008 | Iddan et al. |
| 2008/0221440 A1 | 9/2008 | Iddan et al. |
| 2008/0221442 A1* | 9/2008 | Tolkowsky et al. ........... 600/425 |
| 2008/0247621 A1 | 10/2008 | Zarkh et al. |
| 2008/0253686 A1 | 10/2008 | Bayer |
| 2008/0262346 A1 | 10/2008 | Assis et al. |
| 2008/0267475 A1 | 10/2008 | Lendl |
| 2008/0283771 A1 | 11/2008 | Li |
| 2008/0300487 A1 | 12/2008 | Govari |
| 2009/0016587 A1 | 1/2009 | Strobel et al. |
| 2009/0074284 A1 | 3/2009 | Zeineh et al. |
| 2009/0093676 A1 | 4/2009 | Davidson |
| 2009/0103682 A1 | 4/2009 | Chen et al. |
| 2009/0105579 A1 | 4/2009 | Garibaldi |
| 2009/0116715 A1 | 5/2009 | Bredno et al. |
| 2009/0171201 A1 | 7/2009 | Olson |
| 2009/0177444 A1 | 7/2009 | Wiemker et al. |
| 2009/0216112 A1 | 8/2009 | Assis et al. |
| 2009/0245601 A1 | 10/2009 | Cohen et al. |
| 2009/0257631 A1 | 10/2009 | Baumgart |
| 2009/0264752 A1 | 10/2009 | Markowitz et al. |
| 2009/0264753 A1 | 10/2009 | Von Schulthes |
| 2009/0275831 A1 | 11/2009 | Hall |
| 2009/0281418 A1 | 11/2009 | Ruijters et al. |
| 2009/0299195 A1 | 12/2009 | Muller et al. |
| 2009/0304593 A1 | 12/2009 | Frinking et al. |
| 2009/0306547 A1 | 12/2009 | Iddan et al. |
| 2010/0041949 A1 | 2/2010 | Tolkowsky |
| 2010/0049034 A1 | 2/2010 | Eck et al. |
| 2010/0054573 A1 | 3/2010 | Shekhara |
| 2010/0067768 A1 | 3/2010 | Ionasec et al. |
| 2010/0094124 A1 | 4/2010 | Schoonenberg et al. |
| 2010/0094127 A1 | 4/2010 | Xu |
| 2010/0099979 A1 | 4/2010 | Schoonenberg et al. |
| 2010/0111396 A1 | 5/2010 | Boucheron |
| 2010/0114289 A1 | 5/2010 | Camus |
| 2010/0123715 A1 | 5/2010 | Hansegard |
| 2010/0134517 A1 | 6/2010 | Saikaly et al. |
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |

(56) References Cited

U.S. PATENT DOCUMENTS

| | | |
|---|---|---|
| 2010/0191102 A1 | 7/2010 | Steinberg et al. |
| 2010/0198063 A1 | 8/2010 | Huber |
| 2010/0220917 A1 | 9/2010 | Steinberg et al. |
| 2010/0228076 A1 | 9/2010 | Blank et al. |
| 2010/0246910 A1 | 9/2010 | Wiemker |
| 2010/0272340 A1 | 10/2010 | Bar-Aviv et al. |
| 2010/0290693 A1 | 11/2010 | Cohen et al. |
| 2010/0310140 A1 | 12/2010 | Schneider |
| 2010/0312100 A1 | 12/2010 | Zarkh et al. |
| 2010/0318115 A1 | 12/2010 | Chanduszko et al. |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmidtt et al. |
| 2011/0075912 A1 | 3/2011 | Rieber et al. |
| 2011/0087104 A1 | 4/2011 | Moore |
| 2011/0112398 A1 | 5/2011 | Zarkh et al. |
| 2011/0118825 A1 | 5/2011 | Hunter et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0235889 A1 | 9/2011 | Spahn |
| 2011/0286627 A1 | 11/2011 | Takacs et al. |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1 | 1/2012 | Tolkowsky et al. |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0069167 A1 | 3/2012 | Liu et al. |
| 2012/0072190 A1 | 3/2012 | Sharma et al. |
| 2012/0083696 A1 | 4/2012 | Kitamura |
| 2012/0093379 A1 | 4/2012 | Florent et al. |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0245460 A1 | 9/2012 | Slomka |
| 2012/0250974 A1 | 10/2012 | Miyamoto |
| 2012/0294498 A1 | 11/2012 | Popovic |
| 2012/0300981 A1 | 11/2012 | Yeh et al. |
| 2012/0310081 A1 | 12/2012 | Alder et al. |
| 2013/0004044 A1 | 1/2013 | Ross |
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0116739 A1 | 5/2013 | Brada et al. |
| 2013/0120296 A1 | 5/2013 | Merrit |
| 2013/0120297 A1 | 5/2013 | Merrit |
| 2013/0123616 A1 | 5/2013 | Merrit |
| 2013/0308844 A1 | 11/2013 | Florent et al. |
| 2013/0329030 A1 | 12/2013 | Tolkowsky et al. |
| 2013/0329977 A1 | 12/2013 | Tolkowsky et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Klaiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |
| 2015/0282737 A1 | 10/2015 | Tolkowsky et al. |
| 2015/0282889 A1 | 10/2015 | Cohen et al. |
| 2015/0282890 A1 | 10/2015 | Cohen et al. |
| 2015/0283319 A1 | 10/2015 | Tolkowsky et al. |

FOREIGN PATENT DOCUMENTS

| | | |
|---|---|---|
| WO | 99/07354 A2 | 2/1999 |
| WO | 00/33755 A1 | 6/2000 |
| WO | 01/10313 A1 | 2/2001 |
| WO | WO 01/43642 | 6/2001 |
| WO | 03/043516 A2 | 5/2003 |
| WO | WO 03/096894 | 11/2003 |
| WO | WO 2005/026891 | 3/2005 |
| WO | 2005051452 A2 | 6/2005 |
| WO | WO 2005/124689 | 12/2005 |
| WO | 2006/027781 A2 | 3/2006 |
| WO | WO 2006/066122 | 6/2006 |
| WO | WO 2006/066124 | 6/2006 |
| WO | 2006/076409 A2 | 7/2006 |
| WO | 2006/114721 A2 | 11/2006 |
| WO | WO 2006/121984 | 11/2006 |
| WO | 2007/002685 A2 | 1/2007 |
| WO | 2007/014028 A1 | 2/2007 |
| WO | 2007/015199 A2 | 2/2007 |
| WO | 2008/007350 A1 | 1/2008 |
| WO | WO 2008/007350 | 1/2008 |
| WO | 2008/062358 A1 | 5/2008 |
| WO | WO 2008/107905 | 9/2008 |
| WO | WO 2009/153794 | 12/2009 |
| WO | 2010/058398 A2 | 5/2010 |
| WO | WO 2010/058398 | 5/2010 |
| WO | 2011/046903 A2 | 4/2011 |
| WO | 2011/046904 A1 | 4/2011 |
| WO | 2011128797 A1 | 10/2011 |
| WO | 2011/145094 A2 | 11/2011 |
| WO | 2012/014212 A2 | 2/2012 |
| WO | 2012/028190 A1 | 3/2012 |
| WO | 2012095755 A1 | 7/2012 |
| WO | 2012107857 A1 | 8/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013061225 A1 | 5/2013 |
| WO | 2013/084345 A1 | 6/2013 |
| WO | 2013/128233 A1 | 9/2013 |
| WO | 2013/169814 A1 | 11/2013 |
| WO | 2013/175472 A2 | 11/2013 |
| WO | 2014/002095 A2 | 1/2014 |
| WO | 2015/155770 A1 | 10/2015 |

OTHER PUBLICATIONS

Office Action dated Mar. 14, 2012, issued in U.S. Appl. No. 12/075,214.

Office Action dated Mar. 15, 2012, issued in U.S. Appl. No. 12/649,944.

Office Action dated Mar. 15, 2012, issued in U.S. Appl. No. 12/650,152.

Office Action dated May 22, 2012, issued in U.S. Appl. No. 12/075,244.

Umeda, H. et al., "Promising efficacy of primary gradual and prolonged balloon angioplasty in small coronary arteries: A randomized comparison with cutting balloon angioplasty and conventional balloon angioplasty", American Heart Journal, vol. 147, No. 1 pp. 1-8, Jan. 2004.

Boyle et al., entitled "Assessment of a Novel Angiographic Image Stabilization System for Percutaneous Coronary Intervention" (Journal of Interventional Cardiology, vol. 20 No. 2, 2007.

(56) References Cited

OTHER PUBLICATIONS

Timinger et al., entitled "Motion compensated coronary interventional navigation by means of diaphragm tracking and elastic motion models" (Phys Med Biol. Feb. 7, 2005;50(3):491-503.
Timinger et al., entitled "Motion compensation for interventional navigation on 3D static roadmaps based on an affine model and gating" (Phys Med Biol. Mar. 7, 2004;49(5):719-32.
Turski et al., entitled "Digital Subtraction Angiography 'Road Map'" (American Journal of Roentgenology, 1982.
Iddan et al., entitled "3D imaging in the studio and elsewhere" (SPIE Proceedings vol. 4298, 2001.
"Catheter Insertion Simulation with Combined Visual and Haptic Feedback," by Zorcolo et al. (Center for Advanced Studies, Research and Development in Sardinia).
"4D-CT imaging of a volume influenced by respiratory motion on multi-slice CT Tinsu Pan," by Lee et al., (Medical Physics, Feb. 2004, vol. 31, Issue 2, pp. 333-340)—an abstract.
"New 4-D imaging for real-time intraoperative MRI: adaptive 4-D scan," by Tokuda et al. (Med Image Comput Assist Intery Int Conf. 2006;9(Pt 1):454-61) an abstract.
"Real-time interactive viewing of 4D kinematic MR joint studies," by Schulz et al. (Med Image Comput Assist Interv Int Conf. 2005;8(Pt 1):467-73.)—an abstract.
"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).
"Prospective motion correction of X-ray images for coronary interventions," by Shechter et al. (IEEE Trans Med Imaging. Apr. 2005;24(4):441-50).
"Cardiac Imaging: We Got the Beat!" by Elizabeth Morgan (Medical Imaging, Mar. 2005).
"Noninvasive Coronary Angiography by Retrospectively ECG-Gated Multislice Spiral CT," by Achenbach et al., (Circulation. Dec. 5, 2000;102(23):2823-8).
"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.
"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Softie Mansson, et al., "Dosimetric verification of breathing adapted radiotherapy using polymer gel", Journal of Physics: Conference series 56 (200) 300-303.
"From 2D to 4D" AXIOM Innovations—Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik 1, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.
Brochure: At the TCT conference held in San Francisco, USA in Sep. 2009, Paieon Inc. demonstrated the IC-PRO Comprehensive Imaging Workstation for providing assistance in cardiac catheterization procedures.

An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.
An International Search Report dated May 19, 2010 issued during the prosecution of Applicant's PCT Patent Application No. PCT/IL2009/001089.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).
"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave—Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
Official Action dated Aug. 27, 2012, which issued during the prosecution U.S. Appl. No. 12/075,214.
Official Action dated Oct. 31, 2012, which issued during the prosecution U.S. Appl. No. 12/075,244.
Official Action dated Sep. 20, 2012, which issued during the prosecution of U.S. Appl. No. 12/649,955.

(56) References Cited

OTHER PUBLICATIONS

International Search Report dated Oct. 10, 2012, which issued during the prosecution of PCT/IL2012/000246.
Communication dated Sep. 5, 2012 , which issued during the prosecution of EP Application 09 766 329.8-1526.
Communication dated Oct. 29, 2012 , which issued during the prosecution of EP Application 08 719941.0-1265/2129284.
Official Action dated Oct. 23, 2012, which issued during the prosecution of JP Application No. 2009-552328.
Computer translation of JP 2010-253017 to Takeshi.
W. Goodman et al., "Coronary-Artery Calcification in Young Adults With End-Stage Renal Disease Who Are Undergoing Dialysis," The New England Journal of Medicine, vol. 342 No. 20.
W. Santamore et al., "A microcomputer based automated quantative coronary angiographic analysis system," Annals of Biomedical Engineering, vol. 16, pp. 367-377, 1988.
I. Kompatsiaris et al., "Deformable Boundary Detection of Stents in Angiographic Images," IEEE Transactions on Medical Imaging, vol. 19, No. 6, Jun. 2000.
V. Duddalwar, "Multislice CT angiography: a practical guide to CT angiography in vascular imaging and intervention," The British Journal of Radiology, 77 (2004), S27-S38.
W. Leung et al., "Coronary Artery Quantitation and Data Management System for Paired Cineangiograms," Catheterization and Cardiovascular Diagnosis 24:121-134 (1991).
G. Mancini et al., "Automated quantitative coronary arteriography: morphologic and physiologic validation in vivo of a rapid digital angiographic method," Circulation 1987;75:452-460.
L. Yaneza et al., " Atherosclerotic Plaque Can Be Quantified Using Multifractal and Wavelet Decomposition Techniques," Abstracts—Angiography & Interventional Cardiology, JACC Mar. 3, 2004.
Official Action dated Nov. 23, 2012, which issued during the prosecution of U.S. Appl. No. 12/649,944.
U.S. Appl. No. 61/359,431.
A search report dated Nov. 23, 2012, which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Feb. 4, 2013, which issued during the prosecution of Applicant's U.S. Appl. No. 13/228,185.
An Official Action dated Sep. 6, 2013 , which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
Office Action dated Jul. 2, 2013 issued in corresponding U.S. Appl. No. 12/075,244.
Office Action dated Jun. 19, 2013 issued in corresponding U.S. Appl. No. 12/075,214.
Office Action dated May 31, 2013 issued in corresponding U.S. Appl. No. 12/075,252.
Office Action dated May 6, 2013 issued in corresponding U.S. Appl. No. 12/487,315.
Notice of Allowance dated Jun. 4, 2013 issued in corresponding U.S. Appl. No. 12/649,960.
A Notice of Allowance issued in Applicant's U.S. Appl. No. 13/965,893 Nov. 1, 2013.
An Official Action dated Nov. 13, 2013, which issued during the prosecution of Applicant's U.S. Appl. No. 12/666,879.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL2013/50549, Nov. 20, 2013.
Correspondence from the International Searching Authority in Applicant's PCT/IL2013/050438, Oct. 1, 2013.
Office Action dated Jan. 7, 2014, issued by the U.S. Patent and Trademark Office in corresponding U.S. Appl. No. 12/075,244.
Office Action dated Dec. 31, 2013, issued by the U.S. Patent and Trademark Office in corresponding U.S. Appl. No. 12/075,252.
Office Action dated Feb. 12, 2014, issued by the U.S. Patent and Trademark Office in corresponding U.S. Appl. No. 12/781,260.
Notice of Allowance dated Jan. 3, 2014, issued by the U.S. Patent and Trademark Office in corresponding U.S. Appl. No. 13/965,872.
International Search Report (PCT/ISA/220, PCT/ISA/210, & PCT/ISA/237) dated Dec. 2, 2013, issued by the International Searching Authority in corresponding Application No. PCT/IL2013/050438.
International Search Report (PCT/ISA/220, PCT/ISA/210, & PCT/ISA/237) dated Jan. 22, 2014, issued by the International Searching Authority in corresponding Application No. PCT/IL13/50549.
An Official Action dated Jun. 18, 2014, which issued during the prosecution of Applicant's U.S. Appl. No. 12/075,244.
An Official Action dated Jul. 30, 2014, which issued during the prosecution of Applicant's U.S. Appl. No. 12/075,214.
An Official Action dated Jul. 3, 2014, which issued during the prosecution of Applicant's U.S. Appl. No. 12/648,913.
An Official Action dated May 21, 2014, which issued during the prosecution of Applicant's U.S. Appl. No. 12/650,156.
An Official Action dated Jul. 31, 2014, which issued during the prosecution of Applicant's U.S. Appl. No. 12/649,944.
An Official Action dated Jun. 3, 2014, which issued during the prosecution of Applicant's U.S. Appl. No. 12/781,260.
An Official Action dated May 30, 2014, which issued during the prosecution of Applicant's U.S. Appl. No. 13/228,335.
An Official Action dated May 29, 2014, which issued during the prosecution of Applicant's U.S. Appl. No. 14/097,922.
A Notice of Allowance dated Jun. 24, 2014, issued in Applicant's U.S. Appl. No. 14/097,603.
Office Action dated Feb. 20, 2014, issued in U.S. Appl. No. 12/075,214.
Office Action dated May 6, 2014, issued in U.S. Appl. No. 12/075,252.
Notice of Allowance issued in U.S. Appl. No. 12/666,879.
Office Action dated Mar. 21, 2014, issued in U.S. Appl. No. 12/648,913.
Office Action dated Apr. 3, 2014, issued U.S. Appl. No. 12/649,955.
Office Action dated Mar. 14, 2014, issued in U.S. Appl. No. 12/650,605.
Office Action dated Apr. 25, 2014, issued in U.S. Appl. No. 12/650,121.
Office Action dated Apr. 17, 2014, issued in U.S. Appl. No. 13/228,211.
Office Action dated Apr. 28, 2014, issued in U.S. Appl. No. 13/228,185.
Office Action dated May 5, 2014 issued in U.S. Appl. No. 14/096,968.
Office Action dated Feb. 14, 2014 issued in U.S. Appl. No. 14/098,140.
Tu et al: "Fusion of 3D QCA and IVUS/OCT", Int J Cardiovasc Imaging (2011) 27:197-207, DOI 10.1007/s10554-011-9809-2.
Tu et al.: "In vivo comparison of arterial lumen dimensions assessed by co-registered 3D quantitative coronary angiography intravascular ultrasound and optical coherence tomography", Int J Cardiovasc Imaging (2012) 28:1315-1327, DOI 10.1007/s10554-012-0016-6.
Pyxaras et al.: "Quantitative angiography optical coherence tomography for the functional assessment of nonobstructive coronary stenoses", Am Heart J. 2013;16696):1010-1018.

(56) References Cited

OTHER PUBLICATIONS

Communication dated Aug. 29, 2014 from the USPTO in U.S. Appl. No. 14/098,140.
Communication dated Nov. 7, 2014 from the USPTO in U.S. Appl. No. 14/096,968.
Communication dated Oct. 14, 2014 from the USPTO in U.S. Appl. No. 12/075,252.
Communication dated Oct. 24, 2014 from the USPTO in U.S. Appl. No. 12/650,121.
Communication dated Oct. 8, 2014 from the USPTO in U.S. Appl. No. 14/098,093.
Communication dated Sep. 11, 2014 from the USPTO in U.S. Appl. No. 12/650,152.
Communication dated Sep. 5, 2014 from the USPTO in U.S. Appl. No. 14/143,289.
Communication dated Sep. 5, 2014 from the USPTO in U.S. Appl. No. 14/143,430.
An Official Action dated Mar. 25, 2015, which issued during the prosecution of Applicant's U.S. Appl. No. 12/075,252.
An Official Action dated Apr. 10, 2015 which issued during the prosecution of Applicant's U.S. Appl. No. 12/648,913.
An Official Action dated Apr. 10, 2015 which issued during the prosecution of Applicant's U.S. Appl. No. 12/650,152.
An Official Action dated Apr. 13, 2015 which issued during the prosecution of Applicant's U.S. Appl. No. 12/649,944.
An Official Action dated Mar. 16, 2015 which issued during the prosecution of Applicant's U.S. Appl. No. 13/228,211.
An Official Action dated Mar. 16, 2015 which issued during the prosecution of Applicant's U.S. Appl. No. 13/228,185.
An Official Action dated Mar. 23, 2015 which issued during the prosecution of Applicant's U.S. Appl. No. 14/097,922.
An Official Action dated Apr. 22, 2015 which issued during the prosecution of Applicant's U.S. Appl. No. 14/142,082.
An Official Action dated Feb. 23, 2015 which issued during the prosecution of Applicant's U.S. Appl. No. 14/143,184.
An Official Action dated May 6, 2015 which issued during the prosecution of Applicant's U.S. Appl. No. 12/781,260.
An Official Action dated May 11, 2015 which issued during the prosecution of Applicant's U.S. Appl. No. 12/650,605.
An English translation of an Official Action dated May 12, 2015 which issued during the prosecution of Applicant's Japanese Patent Application No. 521284/2013.
An Official Action dated Dec. 11, 2014, which issued during the prosecution of Applicant's U.S. Appl. No. 12/648,913.
An Official Action dated Feb. 4, 2015 , which issued during the prosecution of Applicant's U.S. Appl. No. 12/649,955.
An Official Action dated Nov. 24, 2014 which issued during the prosecution of Applicant's U.S. Appl. No. 12/781,260.
An Official Action dated Jan. 6, 2015, which issued during the prosecution of Applicant's U.S. Appl. No. 12/650,605.
An Official Action dated Feb. 6, 2015, which issued during the prosecution of Applicant's U.S. Appl. No. 12/650,121.
An Official Action dated Nov. 24, 2014, which issued during the prosecution of Applicant's U.S. Appl. No. 12/649,944.
An Official Action dated Jan. 16, 2015, which issued during the prosecution of Applicant's U.S. Appl. No. 13/228,229.
An Official Action dated Jan. 6, 2015, which issued during the prosecution of Applicant's U.S. Appl. No. 13/228,335.
An Official Action dated Nov. 28, 2014, which issued during the prosecution of Applicant's U.S. Appl. No. 14/097,922.
An Official Action dated Dec. 4, 2014, which issued during the prosecution of Applicant's U.S. Appl. No. 14/098,114.
A Notice of Allowance issued in Applicant's U.S. Appl. No. 12/650,156, Dated Nov. 24, 2014.
A Notice of Allowance issued in Applicant's U.S. Appl. No. 14/143,430, Dated Dec. 19, 2014.
A Notice of Allowance issued in Applicant's U.S. Appl. No. 14/143,289, Dated Jan. 12, 2015.
Communication dated Jan. 23, 2015 which issued during the prosecution of Applicant's EP Application No. 12802046.8.
"Geometrically Correct 3-D Reconstruction of Intravascular Ultrasound Images by Fusion with Biplane Angiography—Methods and Validation," Andreas Wahle, et al., IEEE Transactions on Medical Imaging, Final Manuscript #187/98, Jun. 30, 1999.
International Search Report dated Jan. 6, 2012, issued in PCT Application No. PCT/IL11/00391.
Office Action dated Dec. 8, 2011 issued during the prosecution of U.S. Appl. No. 12/075,244.
Office Action dated Nov. 28, 2011 issued during the prosecution of U.S. Appl. No. 12/075,252.
U.S. Appl. No. 60/845,347 to Strommer et al. filed Sep. 18, 2006.
Communication dated May 21, 2015 from the United States Patent and Trademark Office in counterpart U.S. Appl. No. 14/098,140.
Communication dated Jul. 6, 2015 from the United States Patent and Trademark Office in counterpart U.S. Appl. No. 12/649,955.
Communication dated May 21, 2015 from the Canadian Intellectual Property Office in counterpart application No. 2,874,415.
Communication dated Jun. 30, 2015 from the Japanese Patent Office in counterpart application No. 2014-164417.
Communication dated May 19, 2015 from the United States Patent and Trademark Office in counterpart U.S. Appl. No. 13/228,229.
Communication dated Aug. 4, 2015 from the United States Patent and Trademark Office in counterpart U.S. Appl. No. 14/128,243.
Communication dated Jul. 28, 2015 from the United States Patent and Trademark Office in counterpart U.S. Appl. No. 12/075,252.
Communication dated Jul. 2, 2015 from the Canadian Intellectual Property Office in counterpart application No. 2,875,346.
An Official Action dated Aug. 17, 2015, which issued during the prosecution of Applicant's U.S. Appl. No. 12/648,913.
An Official Action dated Aug. 27, 2015, which issued during the prosecution of Applicant's U.S. Appl. No. 12/650,121.
An Official Action dated Oct. 22, 2015, which issued during the prosecution of Applicant's U.S. Appl. No. 12/649,944.
An Official Action dated Sep. 11, 2015, which issued during the prosecution of Applicant's U.S. Appl. No. 12/781,260.
An Official Action dated Sep. 21, 2015, which issued during the prosecution of Applicant's U.S. Appl. No. 13/228,229.
An Official Action dated Sep. 3, 2015, which issued during the prosecution of Applicant's U.S. Appl. No. 13/228,211.
An Official Action dated Oct. 7, 2015, which issued during the prosecution of Applicant's U.S. Appl. No. 13/228,185.
An Official Action dated Aug. 11, 2015, which issued during the prosecution of Applicant's U.S. Appl. No. 13/228,335.
An Official Action dated Aug. 12, 2015, which issued during the prosecution of Applicant's U.S. Appl. No. 14/097,922.
An Official Action dated Oct. 7, 2015, which issued during the prosecution of Applicant's U.S. Appl. No. 14/142,082.
An Official Action dated Aug. 25, 2015, which issued during the prosecution of Applicant's U.S. Appl. No. 14/143,184.
An Official Action dated Sep. 23, 2015, which issued during the prosecution of Applicant's U.S. Appl. No. 14/742,996.
A European Patent report dated Sep. 8, 2015, which issued during the prosecution of Applicant's European Patent Application No. 08719941.0.
An Official Action dated Sep. 4, 2015, which issued during the prosecution of Applicant's Canadian Application No. 2,874,415.
An International Search Report and Written Opinion dated Aug. 25, 2015, which issued during prosecution of Applicant's PCT/IL2015/050372.

* cited by examiner

34

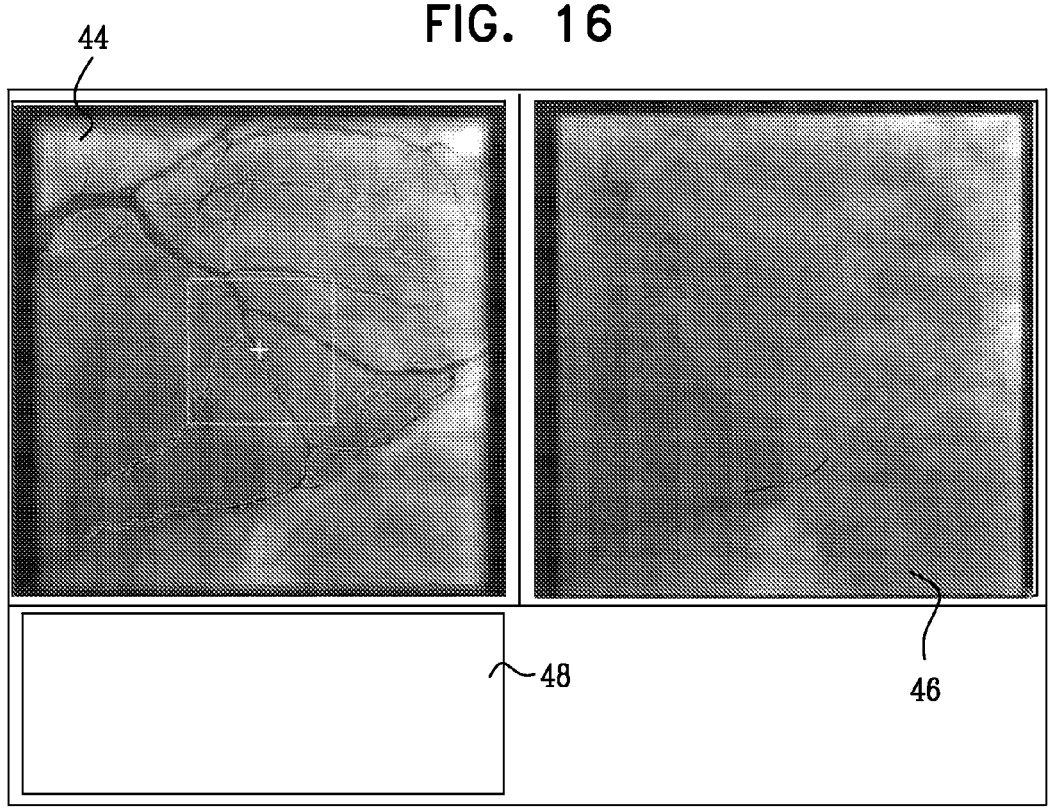

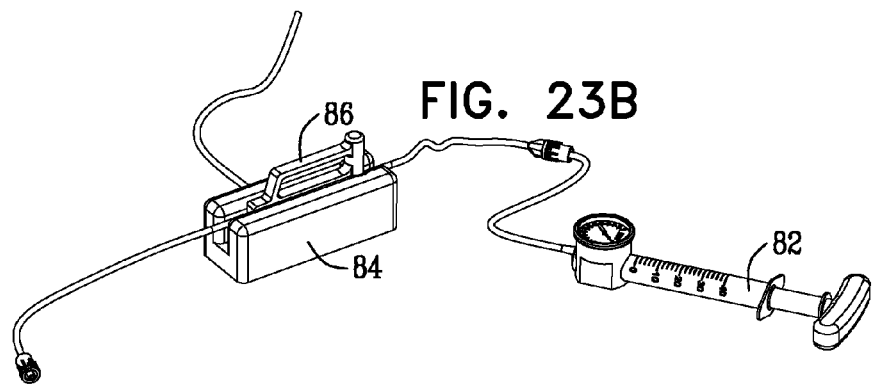
FIG. 23B
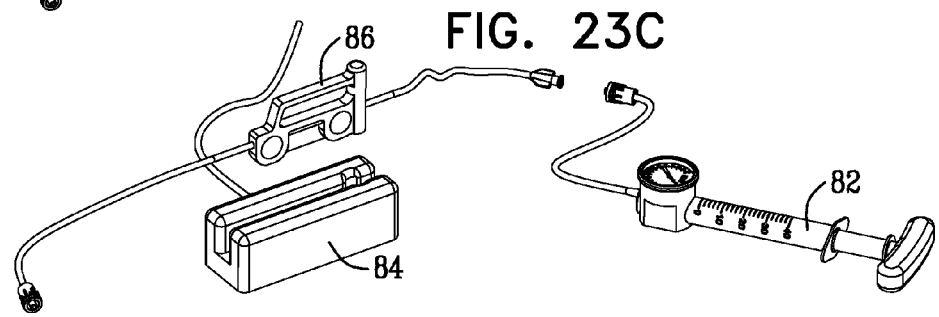
FIG. 23C
FIG. 24
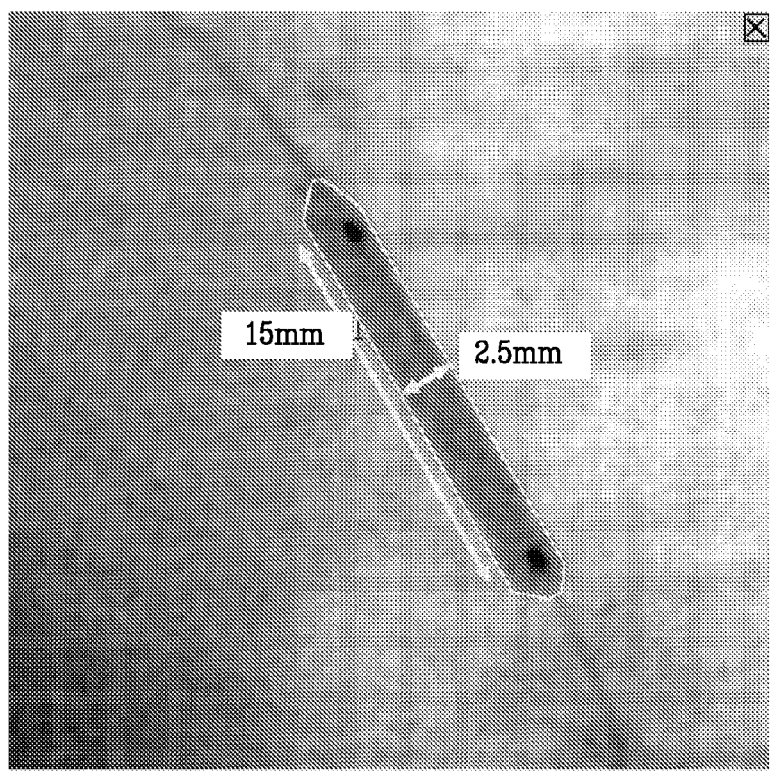

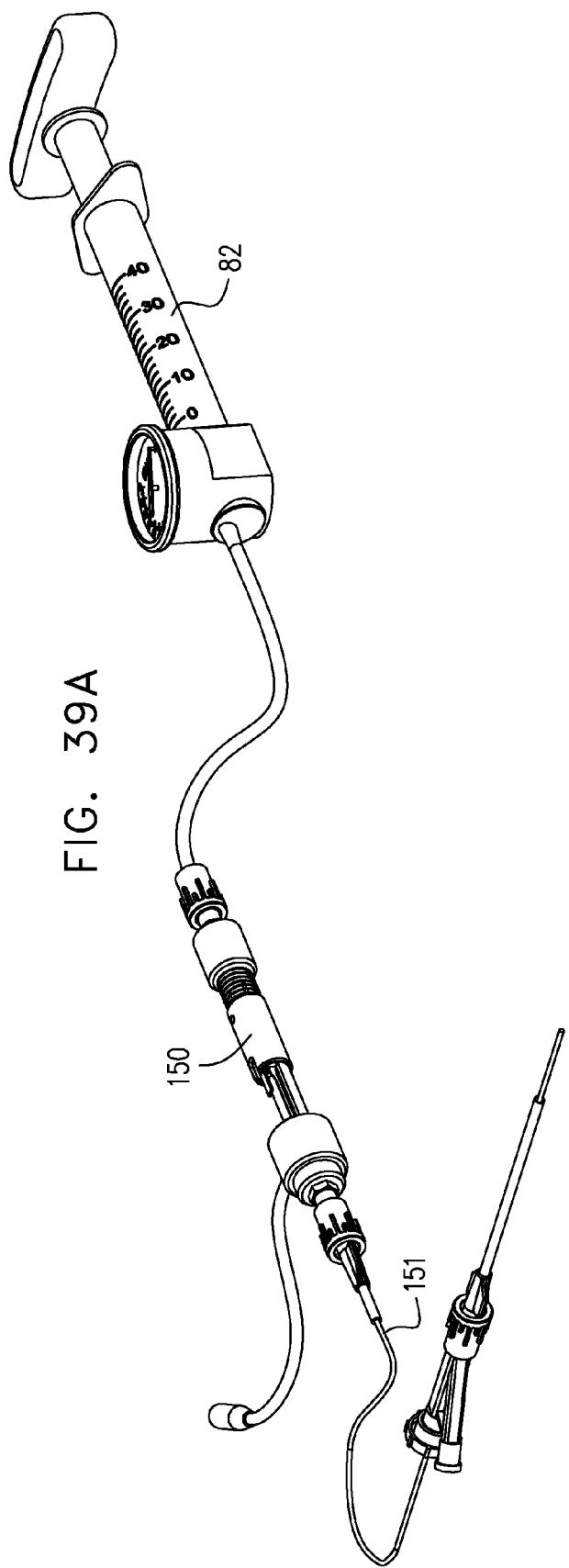

FORMING AND DISPLAYING A COMPOSITE IMAGE

CROSS REFERENCES TO RELATED APPLICATIONS

The present application is:

(a) a continuation-in-part of U.S. application Ser. No. 12/666,879 to Steinberg (issued as U.S. Pat. No. 8,781,193), which is the U.S. national phase of PCT Application no. PCT/IL2009/001089 to Cohen (published as WO 12/058398), filed Nov. 18, 2009, which claims priority from the following patent applications:

U.S. Provisional Patent Application 61/193,329, entitled "Apparatuses and methods for the automatic generation of a road map from angiographic images of a cyclically-moving organ," to Steinberg, filed Nov. 18, 2008

U.S. Provisional Patent Application 61/193,915, entitled "Image processing and tool actuation for medical procedures," to Steinberg, filed Jan. 8, 2009

U.S. Provisional Patent Application 61/202,181, entitled "Image processing and tool actuation for medical procedures," to Steinberg, filed Feb. 4, 2009

U.S. Provisional Patent Application 61/202,451, entitled "Image processing and tool actuation for medical procedures," to Steinberg, filed Mar. 2, 2009

U.S. Provisional Patent Application 61/213,216, entitled "Image processing and tool actuation for medical procedures," to Steinberg, filed May 18, 2009

U.S. Provisional Patent Application 61/213,534, entitled "Image Processing and Tool Actuation for Medical Procedures," to Steinberg, filed Jun. 17, 2009

U.S. Provisional Patent Application 61/272,210, entitled "Image processing and tool actuation for medical procedures," to Steinberg, filed Sep. 1, 2009 and U.S. Provisional Patent Application 61/272,356, entitled "Image Processing and Tool Actuation for Medical Procedures" to Steinberg, filed Sep. 16, 2009; and (b) a continuation-in-part of (i) U.S. patent application Ser. No. 12/075,244 to Tolkowsky (now abandoned), filed Mar. 10, 2008, entitled "Imaging for use with moving organs,"

(ii) U.S. patent application Ser. No. 12/075,214 to Iddan (published as US 2008/0221439, now abandoned), filed Mar. 10, 2008, entitled "Tools for use with moving organs," and (iii) U.S. patent application Ser. No. 12/075,252 to Iddan (published as US 2008/0221440), filed Mar. 10, 2008, entitled "Imaging and tools for use with moving organs,"

all of which applications claim the benefit of U.S. Provisional patent application Nos.:
60/906,091 filed on Mar. 8, 2007,
60/924,609 filed on May 22, 2007,
60/929,165 filed on Jun. 15, 2007,
60/935,914 filed on Sep. 6, 2007, and
60/996,746 filed on Dec. 4, 2007,
all entitled "Apparatuses and methods for performing medical procedures on cyclically-moving body organs."

The present application is related to the following patent applications:

PCT Application PCT/IL2009/00610 to Iddan (published as WO 09/153794), filed on Jun. 18, 2009, entitled "Stepwise advancement of a medical tool" and U.S. patent application Ser. No. 12/487,315 to Iddan (issued as U.S. Pat. No. 8,700,130), filed Jun. 18, 2009, entitled "Stepwise advancement of a medical tool,"

both of which claim the benefit of U.S. Provisional Patent Application No. 61/129,331 to Iddan, filed on Jun. 19, 2008, entitled "Stepwise advancement of a medical tool."

The present application is related to:

PCT Application PCT/IL2008/000316 to Iddan (published as WO 08/107905), filed on Mar. 9, 2009, entitled "Imaging and tools for use with moving organs."

All of the above-mentioned applications are incorporated herein by reference.

FIELD OF EMBODIMENTS OF THE INVENTION

Applications of the present invention generally relate to medical imaging. Specifically, applications of the present invention relate to image processing and tool actuation during medical procedures.

BACKGROUND

In the process of angiography, a contrast agent is typically administered to designated vasculature, and is then imaged by means of a medical imaging modality (such as fluoroscopy). The resulting angiographic images are also known as angiograms. Such angiograms may then be used for constructing a road map of the vasculature, and/or for performing measurements.

WO 08/107,905 to Iddan describes apparatus for use with a portion of a subject's body that moves as a result of cyclic activity of a body system. An imaging device acquires a plurality of image frames of the portion. A sensor senses a phase of the cyclic activity. A medical tool performs a function with respect to the portion. A control unit generates a stabilized set of image frames of the medical tool disposed within the portion, actuates the tool to perform the function or move, in response to the sensor sensing that the cyclic activity is at a given phase thereof, and inhibits the tool from performing the action or moving in response to the sensor sensing that the cyclic activity is not at the given phase. A display facilitates use of the tool by displaying the stabilized set of image frames.

An article by Turski, entitled "Digital Subtraction Angiography 'Road Map'" (American Journal of Roentgenology, 1982) describes a technique called roadmapping.

U.S. Pat. No. 4,878,115 to Elion describes a method in which a dynamic coronary roadmap of the coronary artery system is produced by recording and storing a visual image of the heart creating a mask sequence, recording and storing another dynamic visual image of the heart after injection of a contrast medium thereby creating a contrast sequence, matching the different durations of two sequences and subtracting the contrast sequence from the mask sequence producing a roadmap sequence. The roadmap sequence is then replayed and added to live fluoroscopic images of the beating heart. Replay of the roadmap sequence is triggered by receipt of an ECG R-wave. The result is described as a dynamically moving coronary roadmap image which moves in precise synchronization with the live incoming fluoroscopic image of the beating heart.

U.S. Pat. No. 4,709,385 to Pfeiler describes an x-ray diagnostics installation for subtraction angiography, which has an image memory connected to an output of an x-ray image intensifier video chain which has a number of addresses for storing individual x-ray video signals obtained during a dynamic body cycle of a patient under observation. A differencing unit receives stored signals from the image memory as well as current video signals and subtracts those signals to form a superimposed image. Entry and readout of signals to and from the image memory is under the command of a control unit which is connected to the patient through, for example, an EKG circuit for identifying selected occurrences in the body cycle under observation. Entry and readout of data from the image memory is described as thereby being controlled in synchronization with the selected occurrences in the cycle.

U.S. Pat. Nos. 5,054,045, 5,457,728, 5,586,201 and 5,822,391 to Whiting generally describe a method of displaying details of a coronary artery lesion in a cineangiogram, by digitally adjusting each frame of the cineangiogram so that the lesion is continually displayed at a fixed location on a display screen. The remaining cardiac anatomy is described as appearing to move, in background, past a stationary arterial segment, thus making the displayed arterial segment easier to identify and to examine by medical personnel. Cineangiographic image frames are digitized and processed by an image processor and the image frames are digitally shifted to place the arterial segment in substantially the same viewing location in each frame. Sequential image frames may be presented to the viewer as a stereoscopic pair, to produce pseudostereopsis. The arterial segment is described as appearing to the viewer in foreground, as if it was floating in front of the remaining cardiac anatomy. Image frames may be further processed to aid examination by medical personnel. Frames are described as being averaged to reduce quantum noise and to blur any structure noise. Frame averaging is described as being used to make numerical measurements of arterial cross-section.

U.S. Pat. No. 5,293,574 to Roehm describes an x-ray fluorographic system which produces a cineangiogram and enables a feature in the image to be identified with a cursor and automatically tracked in subsequent images. The identified feature, such as a suspected lesion in a coronary artery, is located in each x-ray frame of the cineangiogram and the data is described as being displayed such that the feature remains motionless in the center of each successive image.

U.S. Pat. No. 5,809,105 to Roehm describes an x-ray fluorographic system which produces frame images at a low dose rate for both on-line and off-line use. Background noise is filtered by first producing a mask which defines the boundaries of the structural features of interest. The mask is used to select the background pixels for filtering, while enabling the structural pixels to pass unfiltered to the display.

U.S. Pat. No. 6,088,488 to Hardy describes a reference image R that is selected and a region of interest (ROI) that is interactively selected encompassing a desired structure from a sequence of images of a moving structure. This ROI is cross-correlated with other real-time images by multiplication in the Fourier frequency domain, to determine if the desired structure is present in the image. If the structure is present, this image may be averaged with other images in which the structure is present to produce higher resolution adaptively averaged images. The technique is described as being particularly useful in imaging coronary vessels. An alternative embodiment is described according to which the offset of the desired structure is calculated in a series of images. The images are then described as being sorted by this offset, and played back in that order to provide a "movie-like" display of the desired structure moving with the periodic motion.

U.S. Pat. No. 6,195,445 to Dubuisson-Jolly describes a technique of displaying a segment of a coronary artery in a stabilized cineangiogram. A computer system receives a sequence of images of a conventional cineangiogram. A user displays a first image on a monitor and selects a point on an arterial segment. The computer system invokes an image tracking procedure that employs active optimal polyline contours to locate the arterial segment and a fixed point in each of the image frames of the conventional cineangiogram. The computer system produces a stabilized cineangiogram by translating the images to place the arterial segment in substantially the same viewing location in each one of the image frames.

U.S. Pat. No. 6,788,827 to Makram-Ebeid describes an image processing method for processing the images of an image sequence comprising steps of determining image data related to first points of an Object of Interest observed in a first image, said Object of Interest having possible movements, and image data related to correlated points found in a second image of the sequence, and based on said image data, of estimating parameters of sets of transformation functions, which transformation functions transform said first points into said correlated points and, from said parameters, of determining one Warping Law that automatically transforms said given Object of Interest of the first image into the same object in the second image of the sequence for following and locating said Object of Interest in said second image of the sequence. The method is described as being applicable to medical imaging, and X-ray examination apparatus.

U.S. Pat. No. 7,289,652 to Florent describes a medical viewing system for displaying a sequence of images of a medical intervention that comprises moving and/or positioning a tool in a body organ, which tool is carried by a support to which at least one marker is attached at a predetermined location with respect to the tool, comprising means for acquiring the sequence of images, and for processing said images during the medical intervention, wherein: extracting means for automatically extracting at least one marker that is attached to the tool support and that neither belongs to the tool nor to the body organ, and yielding the marker location information; computing means for automatically deriving the tool location information from the marker location information, and enhancing means for improving the visibility of the tool and/or the body organ in order to check whether the medical intervention stages are successfully carried out.

An article by Frangi, entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137) describes the examination of a multiscale second order local structure of an image (Hessian), with the purpose of developing a vessel enhancement filter. A vesselness measure is obtained on the basis of all eigenvalues of the Hessian. This measure is tested on two dimensional DSA and three dimensional aortoiliac and cerebral MRA data. Its clinical utility is shown by the simultaneous noise and background suppression and vessel enhancement in maximum intensity projections and volumetric displays.

An article by Dijkstra, entitled "A Note on Two Problems in Connexion with Graphs" (Numerische Mathematik 1, 269-271, 1959), describes the consideration of n points (nodes), some or all pairs of which are connected by a branch, wherein the length of each branch is given. The discussion is restricted to the case where at least one path exists between any two nodes. A first problem considered is the construction of a tree of minimum total length between the n nodes. A second problem considered is finding the path of minimum total length between two given nodes.

An article by Timinger, entitled "Motion compensated coronary interventional navigation by means of diaphragm tracking and elastic motion models" (Phys Med Biol. 2005 Feb. 7; 50(3):491-503) presents a method for compensating the location of an interventional device measured by a magnetic tracking system for organ motion and thus registering it dynamically to a 3D virtual roadmap. The motion compensation is accomplished by using an elastic motion model which is driven by the ECG signal and a respiratory sensor signal derived from ultrasonic diaphragm tracking.

An article by Timinger, entitled "Motion compensation for interventional navigation on 3D static roadmaps based on an affine model and gating" (Phys Med Biol. 2004 Mar. 7; 49(5): 719-32), describes a method for enabling cardiac interventional navigation on motion-compensated 3D static roadmaps.

An article by Zarkh, entitled "Guide wire navigation and therapeutic device localization for catheterization procedure" (International Congress Series 1281 (2005) 311-316), describes research into the development of a system for precise real-time localization of a guide wire tip and therapeutic device, in order to provide assistance in guide wire navigation and accurate device deployment within the coronary arteries with minimal contrast material injection. The goal is described as being achieved by real time monitoring of the guide wire tip and therapeutic device in a sequence of fluoroscopic images, and automatic registration to the 3D model of the artery.

WO 08/007,350 to Sazbon describes a tool for real-time registration between a tubular organ and a device, and a method that utilizes the proposed tool for presenting the device within a reference model of the tubular organ. The proposed tool or markers attached thereto, and the device are shown by one imaging modality and the tubular organ is shown by a different imaging modality, but no imaging modality shows both. Due to the usage of the proposed tool, the registration between the device and the tubular organ is significantly simplified and is described as thus, increasing both speed and accuracy.

At the Transvascular Cardiovascular Therapeutics (TCT) conference held in Washington D.C., USA in October 2008, Paieon Inc. demonstrated the CardiOp-THV system for real-time navigation and positioning of a trans-catheter heart valve.

At the TCT conference held in San Francisco, USA in September 2009, Paieon Inc. demonstrated the IC-PRO Comprehensive Imaging Workstation for providing assistance in cardiac catheterization procedures. The Workstation was described as providing the following functionalities: 3D reconstruction and analysis and left ventricle analysis; Virtual planning of single-stent, multiple-stent, or bifurcation procedures; Device visualization during positioning of single or multiple stenting and post-deployment inflation; Device enhancement, post-deployment analysis and fusion of stent- and vessel images; and PACS/CVIS connectivity.

Direct Flow Medical Inc. (Santa Rosa, Calif., USA) manufactures the Direct Flow valve.

The following references may be of interest:

U.S. Pat. No. 3,871,360 to Van Horn, U.S. Pat. No. 3,954,098 to Dick, U.S. Pat. No. 4,016,871 to Schiff, U.S. Pat. No. 4,031,884 to Henzel, U.S. Pat. No. 4,245,647 to Randall, U.S. Pat. No. 4,270,143 to Morris, U.S. Pat. No. 4,316,218 to Gay, U.S. Pat. No. 4,382,184 to Wernikoff, U.S. Pat. No. 4,545,390 to Leary, U.S. Pat. No. 4,723,938 to Goodin, U.S. Pat. No. 4,758,223 to Rydell, U.S. Pat. No. 4,849,906 to Chodos, U.S. Pat. No. 4,865,043 to Shimoni, U.S. Pat. No. 4,920,413 to Nakamura, U.S. Pat. No. 4,991,589 to Hongo, U.S. Pat. No. 4,994,965 to Crawford, U.S. Pat. No. 5,020,516 to Biondi, U.S. Pat. No. 5,062,056 to Lo, U.S. Pat. No. 5,176,619 to Segalowitz, U.S. Pat. No. 5,295,486 to Wollschlager, U.S. Pat. No. 5,486,192 to Walinsky, U.S. Pat. No. 5,538,494 to Matsuda, U.S. Pat. No. 5,619,995 to Lobodzinski, U.S. Pat. No. 5,630,414 to Horbaschek, U.S. Pat. No. 5,764,723 to Weinberger, U.S. Pat. No. 5,766,208 to McEwan, U.S. Pat. No. 5,830,222 to Makower, U.S. Pat. No. 5,971,976 to Wang, U.S. Pat. No. 6,126,608 to Kemme, U.S. Pat. No. 6,233,478 to Liu, U.S. Pat. No. 6,246,898 to Vesely, U.S. Pat. No. 6,331,181 to Tierney, U.S. Pat. No. 6,377,011 to Ben-Ur, U.S. Pat. No. 6,442,415 to Bis, U.S. Pat. No. 6,473,635 to Rasche, U.S. Pat. No. 6,496,716 to Langer, U.S. Pat. No. 6,532,380 to Close, U.S. Pat. No. 6,666,863 to Wentzel, U.S. Pat. No. 6,704,593 to Stainsby, U.S. Pat. No. 6,708,052 to Mao, U.S. Pat. No. 6,711,436 to Duhaylongsod, U.S. Pat. No. 6,728,566 to Subramanyan, U.S. Pat. No. 6,731,973 to Voith, U.S. Pat. No. 6,786,896 to Madhani, U.S. Pat. No. 6,858,003 to Evans, U.S. Pat. No. 6,937,696 to Mostafavi, U.S. Pat. No. 6,959,266 to Mostafavi, U.S. Pat. No. 6,973,202 to Mostafavi, U.S. Pat. No. 6,980,675 to Evron, U.S. Pat. No. 6,999,852 to Green, U.S. Pat. No. 7,085,342 to Younis, U.S. Pat. No. 7,155,046 to Aben, U.S. Pat. No. 7,155,315 to Niemeyer, U.S. Pat. No. 7,180,976 to Wink, U.S. Pat. No. 7,191,100 to Mostafavi, U.S. Pat. No. 7,209,779 to Kaufman, U.S. Pat. No. 7,269,457 to Shafer, U.S. Pat. No. 7,321,677 to Evron, U.S. Pat. No. 7,339,585 to Verstraelen, U.S. Pat. No. 7,587,074 to Zarkh;

US 2002/0049375 to Strommer, US 2002/0188307 to Pintor, US 2003/0018251 to Solomon, US 2003/0023141 to Stelzer, US 2003/0157073 to Peritt, US 2004/0077941 to Reddy, US 2004/0097805 to Verard, US 2004/0176681 to Mao, US 2005/0008210 to Evron, US 2005/0054916 to Mostafavi, US 2005/0090737 to Burrel, US 2005/0107688 to Strommer, US 2005/0137661 to Sra, US 2005/0143777 to Sra, US 2006/0074285 to Zarkh, US 2006/0287595 to Maschke, US 2006/0058647 to Strommer, US 2007/0038061 to Huennekens, US 2007/0053558 to Puts, US 2007/0106146 to Altmann, US 2007/0142907 to Moaddeb, US 2007/0173861 to Strommer, US 2007/0208388 to Jahns, US 2007/0219630 to Chu; US 2008/0221442 to Tolkowsky; US 2010/0041949 to Tolkowsky WO 94/010904 to Nardella, WO 01/43642 to Heuscher, WO 03/096894 to Ho, WO 05/026891 to Mostafavi, WO 05/124689 to Manzke, WO 06/066122 to Sra, WO 06/066124 to Sra;

"3D imaging in the studio and elsewhere," by Iddan (SPIE Proceedings Vol. 4298, 2001);

"4D smoothing of gated SPECT images using a left-ventricle shape model and a deformable mesh," by Brankov (Nuclear Science Symposium Conference Record, 2004 IEEE, October 2004, Volume: 5, 2845-2848);

"4D-CT imaging of a volume influenced by respiratory motion on multi-slice CT Tinsu Pan," by Lee (Medical Physics, February 2004, Volume 31, Issue 2, pp. 333-340);

"Advanced and Challenges in Super-Resolution," by Farsiu (International Journal of Imaging Systems and Technology, Vol. 14, No. 2, pp. 47-57, Special issue on high-resolution image reconstruction, August 2004)

"A new point matching algorithm for non-rigid registration," by Chui (Computer Vision and Image Understanding 89 (2003) 114-141)

"Assessment of a Novel Angiographic Image Stabilization System for Percutaneous Coronary Intervention" by Boyle (Journal of Interventional Cardiology," Vol. 20 No. 2, 2007);

"Cardiac Imaging: We Got the Beat!" by Elizabeth Morgan (Medical Imaging, March 2005);

"Catheter Insertion Simulation with Combined Visual and Haptic Feedback," by Zorcolo (Center for Advanced Studies, Research and Development in Sardinia);

"Full-scale clinical implementation of a video based respiratory gating system," by Ramsey (Engineering in Medicine and Biology Society, 2000. Proceedings of the 22nd Annual International Conference of the IEEE, 2000, Volume: 3, 2141-2144);

"Image inpainting," by Bertalmio (ACM Siggraph 2000, New Orleans, La., USA, July 2000)

"Image Registration by Minimization of Residual Complexity," by Myronenko (CVPR 2009)

"New 4-D imaging for real-time intraoperative MRI: adaptive 4-D scan," by Tokuda (Med Image Comput Assist Intery Int Conf. 2006; 9(Pt 1):454-61);

"Noninvasive Coronary Angiography by Retrospectively ECG-Gated Multislice Spiral CT," by Achenbach (Circulation. 2000 Dec. 5; 102(23):2823-8);

"Nonrigid registration using free-form deformations: application to breast MR images," by Rueckert, (IEEE Trans. Med. 1 mg, Vol. 18, No. 8, 1999)

"Prospective motion correction of X-ray images for coronary interventions," by Shechter (IEEE Trans Med Imaging. 2005 April; 24(4):441-50);

"Real-time interactive viewing of 4D kinematic MR joint studies," by Schulz (Med Image Comput Assist Intery Int Conf. 2005; 8(Pt 1):467-73.);

"Spatially-adaptive temporal smoothing for reconstruction of dynamic and gated image sequences," by Brankov (Nuclear Science Symposium Conference Record, 2000 IEEE, 2000, Volume: 2, 15/146-15/150);

"Three-Dimensional Respiratory-Gated MR Angiography of the Coronary Arteries: Comparison with Conventional Coronary Angiography," by Post (AJR, 1996; 166: 1399-1404);

"Unwarping of unidirectionally distorted EPI images," by Kybic (IEEE Trans. Med. Img., Vol. 19, No. 2, 2000).

SUMMARY OF EMBODIMENTS

For some applications of the present invention, apparatus and methods are provided for use in image processing and tool actuation in the course of a coronary angioplasty procedure. For example, apparatus and methods are provided for: automated generation of a road-map, the generation of automated measurements, automatic image stabilization, automatic image enhancement, tool positioning and tool deployment.

For some applications, a road map is displayed together with a stabilized image stream.

Typically, image processing as described in the present application is performed on-line. However, the scope of the present application includes performing the techniques described herein off line.

Although many of the applications of the present invention are described with reference to the diagnosis and treatment of the coronary arteries in the context of coronary angiography and/or angioplasty, the scope of the present invention includes applying the apparatus and methods described herein to other medical procedures. The scope of the present invention includes applying the techniques described herein to any bodily lumen or cavity on which diagnosis and/or treatment may be performed, including but not limited to the vascular system, chambers of the heart, the bronchial tract, the gastro-intestinal tract, or any combination thereof, and using any form of imaging and any applicable medical tool. For example, the scope of the present invention includes applying the apparatus and methods described herein to valve replacement or repair, closure of septal defects, ablation of cardiac tissue, or other medical interventions, as described in further detail hereinbelow.

For some applications, one or more of the procedures described herein is performed under guidance of an image stream that has been image tracked with respect to a portion of a tool that is used for the procedure. Typically, performing the procedure using such image guidance facilitates the performance of the procedure by a healthcare professional.

For some applications, a medical tool is actuated in synchronization with the cyclical motion of the organ being imaged. For some applications, in addition to the medical tool being actuated in synchronization with the cyclical motion of an organ, a stabilized image stream of the organ is displayed.

For some applications, the techniques described herein are performed in combination with techniques described in PCT Application PCT/IL2008/00316 to Iddan (published as WO 08/107905), filed on Mar. 9, 2008, entitled "Imaging and tools for use with moving organs," which is incorporated herein by reference.

For some applications, the techniques described herein are performed in combination with techniques described in PCT Application PCT/IL2009/00610 to Iddan(published as WO 09/153794), filed on Jun. 18, 2009, entitled "Stepwise advancement of a medical tool," which is incorporated herein by reference.

There is therefore provided, in accordance with some applications of the present invention, a method, including:

receiving into at least one processor a set of images of blood vessels of a subject;

generating a road map of the subject's blood vessels, by automatically:

deriving at least one image from the set of images of the blood vessels, based upon visibility of at least a portion of the blood vessels in the set of images; and in the derived image, determining a location of edge lines of at least some of the portion of the blood vessels in the image; and generating an output by the processor, based on the road map.

For some applications, generating the output includes overlaying the edge lines on an image stream that is based upon the set of images.

For some applications, generating the output includes overlaying the edge lines on a single image that is derived from the set of images.

For some applications, generating the road map includes generating a road map that corresponds to a given phase of a motion cycle of the blood vessels, and generating the output includes overlaying the road map on an image stream of the blood vessels that is gated to the given phase.

For some applications, generating the road map includes generating the road map in real time.

For some applications, generating the road map includes generating the road map in near real time.

For some applications, the method further includes generating distance indicators along the edge lines.

For some applications, generating the road map further includes automatically enhancing the at least some of the portion of the blood vessels in the derived image.

For some applications, determining the location of the edge lines includes determining a location of discontinuous edge lines using image processing, and filling gaps in the discontinuous edge lines using a gap-filling algorithm.

For some applications, deriving the at least one image from the set of images includes selecting a single image from the set of images, based upon visibility of at least a portion of the blood vessels in the set of images.

For some applications, deriving the at least one image from the set of images includes selecting two or more images from the set of images, based upon visibility of at least a portion of the blood vessels in the set of images, and generating an image, based upon the two or more images.

For some applications, generating the image based upon the two or more images includes aggregating the two or more images.

For some applications, generating the road map includes, using image processing, automatically deriving lines that correspond to paths of the at least some of the portion of the blood vessels in the derived image, and determining the location of the edge lines includes determining the location of the edge lines based upon the lines that correspond to the paths.

For some applications, the lines that correspond to the paths are discontinuous and have end points at discontinuities in the lines, and the method further includes automatically generating continuous lines that correspond to the paths, by bridging the discontinuities in the discontinuous lines.

For some applications, determining the location of the edge lines includes using a penalty function that is based upon the lines that correspond to the paths.

There is further provided, in accordance with some applications of the present invention, apparatus, including:
an image-acquisition device configured to acquire a set of images of blood vessels of a subject;
a display; and
at least one processor, including:
image-receiving functionality configured to receive the set of images into the processor;
image-derivation functionality configured to automatically derive at least one image from the set of images of the blood vessels, based upon visibility of at least a portion of the blood vessels in the set of images; and
edge-line-determination functionality configured to automatically generate a road map by determining a location of edge lines of at least some of the portion of the blood vessels in the derived image; and
display-driving functionality configured to drive the display to display an output to a user based upon the road map.

For some applications, the processor further includes distance-indicating functionality configured to generate distance indicators along the edge lines, and the display-driving functionality is configured to drive the display to display the distance indicators along the edge lines.

For some applications, the processor further includes image-enhancement functionality configured to automatically enhance the at least some of the portion of the blood vessels in the derived image.

For some applications, the processor further includes line-derivation functionality configured, using image processing, to automatically derive lines that correspond to paths of at least the some of the portion of the blood vessels in the image, and the edge-line-determination functionality is configured to determine the location of the edge lines based upon the lines that correspond to the paths.

For some applications, the lines that correspond to the paths are discontinuous and have end points at discontinuities in the lines, and the processor further includes line-bridging functionality configured to, automatically, generate continuous lines that correspond to the paths of the portion of the blood vessels in the image, by bridging the discontinuities in the discontinuous lines.

There is additionally provided, in accordance with some applications of the present invention, a method, including:
receiving into at least one processor at least one image of blood vessels of a subject;

using image processing, automatically deriving discontinuous lines that correspond to paths of at least a portion of the blood vessels in the image, the lines having end points at discontinuities in the lines;
automatically generating continuous lines that correspond to the paths of the portion of the blood vessels in the image by bridging the discontinuities in the discontinuous lines; and
generating an output by the processor, based on the continuous lines.

For some applications, receiving the at least one image includes receiving into the processor a plurality of images of the blood vessels, and generating the output includes overlaying the lines on an image stream that is based upon the plurality of images.

For some applications, generating the output includes overlaying the lines on the image of the blood vessels.

For some applications, generating the output includes overlaying the lines on a current real time image stream of the blood vessels.

For some applications, generating the lines includes generating lines corresponding to the paths of the blood vessels during a given phase of a motion cycle of the blood vessels, and generating the output includes overlaying the lines on an image stream of the blood vessels that is gated to the given phase.

For some applications, generating the continuous lines includes generating the continuous lines in real time.

For some applications, generating the continuous lines includes generating the continuous lines in near real time.

For some applications, the method further includes automatically determining a location of edge lines of the portion of the blood vessels, based upon the lines that correspond to the paths.

For some applications, deriving the discontinuous lines includes deriving discontinuous lines that correspond to center lines of the portion of the blood vessels.

For some applications, deriving the discontinuous lines includes deriving lines corresponding to paths of the blood vessels, based upon the lines having greater visibility than other lines corresponding to paths of the blood vessels in the at least one image.

For some applications, adjacent to at least one first end point of the end points, there are a plurality of second end points of the end points, and bridging the discontinuities includes determining to which of the second end points to bridge from the first end point.

For some applications, receiving the image includes receiving an image that was acquired in a presence of a contrast agent.

For some applications, bridging the discontinuities includes bridging the discontinuities based upon a shortest-path algorithm.

For some applications, bridging the discontinuities includes bridging the discontinuities based upon a known structure of the portion of the blood vessels.

There is further provided, in accordance with some applications of the present invention, apparatus, including:
an image-acquisition device configured to acquire at least one image of blood vessels of a subject;
a display; and
at least one processor, including:
image-receiving functionality configured to receive the at least one image into the processor;
line-derivation functionality configured, using image processing, to automatically derive discontinuous lines that correspond to paths of at least a portion of the blood vessels in the image, the lines having end points at discontinuities in the lines;

line-bridging functionality configured to, automatically, generate continuous lines that correspond to the paths of the portion of the blood vessels in the image, by bridging the discontinuities in the discontinuous lines; and display-driving functionality configured to drive the display to display an output to a user based on the continuous lines.

For some applications, the processor further includes edge-line-determination functionality configured to determine a location of edge lines of the portion of the blood vessels, based upon the lines that correspond to the paths.

There is additionally provided, in accordance with some applications of the present invention, a method for use with blood vessels of a subject that move cyclically, in accordance with a motion cycle, including:

receiving into at least one processor a set of images of the blood vessels;

automatically, deriving at least one image from the set of images of the blood vessels, based upon:

(a) timing of acquisition of images from the set of images with respect to the motion cycle, and (b) visibility of at least a portion of the blood vessels in the set of images; generating a road map based upon the derived image; and generating an output based upon the road map.

For some applications, receiving the set of images includes receiving a set of angiographic images.

For some applications, deriving the at least one image from the set of images includes selecting a single image from the set of images, based upon the (a) timing of acquisition of images from the set of images with respect to the motion cycle, and (b) visibility of at least a portion of the blood vessels in the set of images.

For some applications, deriving the at least one image from the set of images includes:

selecting two or more images from the set of images, based upon the (a) timing of acquisition of images from the set of images with respect to the motion cycle, and (b) visibility of at least a portion of the blood vessels in the set of images; and generating an image, based upon the two or more images.

For some applications, generating the image based upon the two or more images includes aggregating the two or more images.

There is further provided, in accordance with some applications of the present invention, apparatus for use with blood vessels of a subject that move cyclically, in accordance with a motion cycle, including:

an image-acquisition device configured to acquire a set of images of the blood vessels;

a display; and at least one processor, including:

image-receiving functionality configured to receive the set of images into the processor;

image-derivation functionality configured to automatically derive at least one image from the set of images of the blood vessels, based upon:

(a) timing of acquisition of images from the set of images with respect to the motion cycle, and (b) visibility of at least a portion of the blood vessels in the set of images;

road-map-generation functionality configured to generate a road map based upon the derived image; and display-driving functionality configured to drive the display to display an output to a user based upon the road map.

There is further provided, in accordance with some applications of the present invention, a method, including:

generating a road map of a blood vessel;

subsequently, inserting a tool into the blood vessel;

while the tool is inside the blood vessel, determining a position of the tool; and modifying the road map to account for the determined position of the tool.

For some applications, the tool includes a wire, and inserting the tool into the blood vessel includes inserting the wire into the blood vessel.

For some applications, the tool includes a catheter, and inserting the tool into the blood vessel includes inserting the catheter into the blood vessel.

There is additionally provided, in accordance with some applications of the present invention, apparatus, including:

an image-acquisition device configured to acquire a set of images of blood vessels of a subject;

a tool configured to be placed inside one of the blood vessels;

a display; and at least one processor, including:

image-receiving functionality configured to receive the set of images into the processor;

road-map-generation functionality configured to generate a road map of the blood vessels, based upon the set of images;

tool-location functionality configured to determine a location of the tool subsequent to the generation of the road map; and road-map-modification functionality configured to modify the road map to account for the determined position of the tool; and display-driving functionality configured to drive the display to display an output to a user based on the modified road map.

There is further provided, in accordance with some applications of the present invention, a method for use with an image of blood vessels of a subject, including:

in response to a user designating a single point on the image:

automatically identifying a target portion of a blood vessel in a vicinity of the designated point;

performing quantitative vessel analysis on the target portion of the blood vessel; and generating an output based upon the quantitative vessel analysis.

For some applications, the blood vessel includes a coronary artery, and performing the quantitative vessel analysis with respect to the blood vessel includes performing quantitative coronary angiography.

For some applications, identifying the target portion includes designating a longitudinal portion of the blood vessel having a proximal end that is at a first distance from the point in a proximal direction, and having a distal end that is at a second distance from the point in a distal direction.

For some applications, performing quantitative vessel analysis with respect to the longitudinal portion includes determining a minimum diameter of the blood vessel within the longitudinal portion.

For some applications, designating the longitudinal portion includes designating a longitudinal portion, the first and second distances of which are equal to each other.

For some applications, designating the longitudinal portion includes designating a longitudinal portion, the first and second distances of which are different from each other.

For some applications, designating the longitudinal portion includes designating a longitudinal portion, a sum of the first and second distances of which corresponds to a length of a given tool.

For some applications, identifying the target portion includes identifying a portion of the blood vessel that corresponds to a lesion.

For some applications, performing quantitative vessel analysis includes determining a minimum diameter of the lesion.

For some applications, performing quantitative vessel analysis includes determining a maximum diameter of the lesion.

For some applications, performing quantitative vessel analysis includes determining a length of the lesion.

For some applications, identifying the portion of the blood vessel that corresponds to the lesion includes identifying edge lines of the blood vessel.

For some applications, identifying the portion of the blood vessel that corresponds to the lesion includes identifying proximal and distal longitudinal locations of the blood vessel at which the lesion ends.

There is further provided, in accordance with some applications of the present invention, apparatus, including:
a display configured to display an image of blood vessels of a subject;
an input device; and
at least one processor, including:
target-identification functionality configured, in response to a user designating a single point on the image, using the input device, to automatically identify a target portion of a blood vessel in a vicinity of the designated point;
quantitative-vessel-analysis functionality configured to perform quantitative vessel analysis on the target portion of the blood vessel; and
display-driving functionality configured to drive the display to display an output in response to the quantitative vessel analysis.

There is additionally provided, in accordance with some applications of the present invention, a method for use with an image of blood vessels of a subject, including:
in response to a user designating a single point on the image:
automatically identifying a portion of a blood vessel in a vicinity of the designated point that corresponds to a lesion, by:
automatically determining a location of edge lines of the blood vessel, and
automatically determining longitudinal locations along the blood vessel that correspond to ends of the lesion; and
generating an output in response to the identification of the portion that corresponds to the lesion.

For some applications, the method further includes performing quantitative vessel analysis with respect to the portion.

There is further provided, in accordance with some applications of the present invention, apparatus, including:
a display configured to display an image of blood vessels of a subject;
an input device; and
at least one processor, including:
lesion-identification functionality configured, in response to a user designating a single point on the image, using the input device, to identify a portion of a blood vessel in a vicinity of the designated point that corresponds to a lesion, by:
automatically determining a location of edge lines of the blood vessel, and
automatically determining longitudinal locations along the blood vessel that correspond to ends of the lesion; and
display-driving functionality configured to drive the display to display an output in response to the identification of the portion that corresponds to the lesion.

For some applications, the processor further includes quantitative-vessel-analysis functionality configured to perform quantitative vessel analysis on the identified portion.

There is additionally provided, in accordance with some applications of the present invention, a method for use with an image of blood vessels of a subject, including:
in response to a user designating a first longitudinal location of a blood vessel, and subsequently designating a plurality of additional longitudinal locations of the blood vessel,
automatically determining a parameter of the blood vessel at each of the additional locations selected from the group consisting of:
a diameter of the blood vessel associated with the additional location,
a level of occlusion of the blood vessel associated with the additional location, and
a longitudinal distance along the blood vessel associated with the additional location; and
generating an output in response to the determined parameter at each of the locations.

For some applications, determining the selected parameter includes determining an average diameter of the blood vessel between the first longitudinal location and the additional location.

For some applications, determining the selected parameter includes determining a minimum diameter of the blood vessel between the first longitudinal location and the additional location.

For some applications, determining the selected parameter includes determining a diameter of the blood vessel at the additional location.

For some applications, determining the selected parameter includes determining a longitudinal distance from the first longitudinal location to the additional location.

For some applications, determining the selected parameter includes determining a longitudinal distance from an end of a lesion of the blood vessel to the additional location.

For some applications, determining the parameter includes determining a minimum lumen diameter associated with the additional location.

There is further provided, in accordance with some applications of the present invention, apparatus, including:
a display configured to display an image of blood vessels of a subject;
an input device; and
at least one processor, including:
parameter-determination functionality configured, in response to a user designating a first longitudinal location of a blood vessel, and subsequently designating a plurality of additional longitudinal locations of the blood vessel, to automatically determine a parameter of the blood vessel at each of the additional locations, the parameter selected from the group consisting of:
a diameter of the blood vessel associated with the additional location, a level of occlusion of the blood vessel associated with the additional location, and a longitudinal distance along the blood vessel associated with the additional location; and display-driving functionality configured to drive the display to display an output in response to the determined parameter.

There is additionally provided, in accordance with some applications of the present invention, a method for use with an image of blood vessels of a subject, including:

displaying a cursor in a vicinity of one of the blood vessels on the image; and in response to receiving an input from a user indicating that the cursor should be moved, only allowing movement of the cursor along a direction of paths of the blood vessels.

For some applications, only allowing movement of the cursor along the direction of the paths includes allowing movement of the cursor within the blood vessels along the direction of the paths.

For some applications, only allowing movement of the cursor along the direction of the paths includes allowing movement of the cursor alongside the blood vessels, along the direction of the paths.

There is further provided, in accordance with some applications of the present invention, apparatus, including:

a display;

an input device; and at least one processor, including:

display-driving functionality configured to drive the display to display a cursor in an image of blood vessels of a subject, in a vicinity of one of the blood vessels on the image; and cursor-control functionality configured (a) in response to receiving an input from a user, via the input device, indicating that the cursor should be moved, (b) only to allow movement of the cursor along a direction of paths of the blood vessels.

There is additionally provided, in accordance with some applications of the present invention, a method, including:

generating a sequence of endoluminal cross-sectional images of respective sections of a blood vessel of a subject;

generating an extraluminal image of the blood vessel;

determining that respective regions of the extraluminal image of the blood vessel correspond to the sections;

determining dimensions of at least some of the regions of the extraluminal image by performing quantitative vessel analysis with respect to the at least some of the regions of the extraluminal image; and displaying at least some of the endoluminal images of respective sections of the blood vessel together with the dimensions of the corresponding region.

For some applications, determining that respective regions of the extraluminal image of the blood vessel correspond to the sections includes registering the extraluminal image with the endoluminal images.

There is further provided, in accordance with some applications of the present invention, apparatus, including:

an endoluminal imaging device configured to acquire a sequence of endoluminal cross-sectional images of respective sections of a blood vessel of a subject;

an extraluminal imaging device configured to acquire at least one extraluminal image of the blood vessel;

a display; and at least one processor, including:

image-receiving functionality configured to receive the endoluminal and extraluminal images;

image-assigning functionality configured to determine that respective regions of the extraluminal image of the blood vessel correspond to the sections; and dimension-determining functionality configured to determine dimensions of at least some of the regions of the extraluminal image by performing quantitative vessel analysis with respect to the at least some of the regions of the extraluminal image; and display-driving functionality configured to drive the display to display at least some of the endoluminal images of respective sections of the blood vessel together with the dimensions of the corresponding region.

There is additionally provided, in accordance with some applications of the present invention, a method, including:

inserting a tool into a blood vessel;

while the tool is within the blood vessel, acquiring an extraluminal image of the blood vessel;

in the extraluminal image of the blood vessel, automatically detecting a location of a portion of the tool with respect to the blood vessel;

in response to detecting the location of the portion of the tool, automatically designating a target portion of the blood vessel that is in a vicinity of the portion of the tool; and using the extraluminal image, performing quantitative vessel analysis on the target portion of the blood vessel.

For some applications, the tool includes a balloon, and inserting the tool includes inserting the balloon.

For some applications, the tool includes a replacement valve, and inserting the tool includes inserting the replacement valve.

For some applications, the tool includes a stent, and inserting the tool includes inserting the stent.

For some applications, the tool includes a graft, and inserting the tool includes inserting the graft.

There is further provided, in accordance with some applications of the present invention, apparatus, including:

a tool configured to be placed inside a blood vessel of a subject;

an extraluminal image-acquisition device configured to acquire an image of the blood vessel, while the tool is inside the blood vessel;

a display; and at least one processor, including:

image-receiving functionality configured to receive the image into the processor;

tool-detection functionality configured to automatically detect a location of a portion of the tool, with respect to the blood vessel, in the image;

target-designation functionality configured, in response to detecting the location of the portion of the tool, to automatically designate a target portion of the blood vessel that is in a vicinity of the portion of the tool;

quantitative-vessel-analysis functionality configured to perform quantitative vessel analysis on the target portion of the blood vessel, using the image; and display-driving functionality configured to drive the display to display an output in response to the quantitative vessel analysis.

There is additionally provided, in accordance with some applications of the present invention, a method for imaging a tool inside a portion of a subject's body that undergoes motion, the method including:

acquiring a plurality of image frames of the portion of the subject's body;

image tracking the image frames by:

automatically identifying at least a feature of the tool in at least a portion of the image frames, and aligning the tool in image frames of the portion of the image frames, based on the automatic identifying; and displaying, as an image stream, the image-tracked image frames of the portion of the subject's body.

For some applications, aligning the tool includes translating at least one of the image frames.

For some applications, aligning the tool includes rotating at least one of the image frames.

For some applications, aligning the tool includes scaling at least one of the image frames.

For some applications, the tool includes a balloon, and automatically identifying at least the feature of the tool includes automatically identifying at least a feature of the balloon.

For some applications, the tool includes a stent, and automatically identifying at least the feature of the tool includes automatically identifying at least a feature of the stent.

For some applications, the tool includes a graft, and automatically identifying at least the feature of the tool includes automatically identifying at least a feature of the graft.

For some applications, the tool includes a replacement valve, and automatically identifying at least the feature of the tool includes automatically identifying at least a feature of the replacement valve.

For some applications, the tool includes a hole-closing tool for closing a hole in a septal wall, and automatically identifying at least the feature of the tool includes automatically identifying at least a feature of the hole-closing tool.

For some applications, the tool includes a valve-placement tool for facilitating placement of a replacement valve, and automatically identifying at least the feature of the tool includes automatically identifying at least a feature of the valve-placement tool.

For some applications, the tool includes a tool selected from the group consisting of: a catheter, an energy-application tool, a percutaneous-myocardial-revascularization tool, a substance-delivery tool, a tissue-repair tool, a trans-thoracic-needle, and a trans-bronchial needle, and automatically identifying at least the feature of the tool includes automatically identifying at least a feature of the selected tool.

For some applications, the tool includes a valve-repair tool, and automatically identifying at least the feature of the tool includes automatically identifying at least a feature of the valve-repair tool.

For some applications, the tool includes a valve-suturing tool for suturing a valve, and automatically identifying at least the feature of the tool includes automatically identifying at least a feature of the valve-suturing tool.

For some applications, the tool includes a valve-leaflet-clipping tool for clipping a valve, and automatically identifying at least the feature of the tool includes automatically identifying at least a feature of the valve-leaflet-clipping tool.

For some applications, displaying the image-tracked image frames includes displaying an image stream in which motion of the tool relative to the portion of the subject's body is visible, but motion of the tool that is the same as motion of the portion of the subject's body is not visible.

For some applications, displaying the image-tracked image frames includes displaying an image stream in which motion of the tool relative to the portion of the subject's body over a cycle of cyclical motion of the portion of the subject's body is shown.

For some applications, the method further includes designating at least one image frame as not providing sufficient visibility of the feature of the tool, and, in response to designating the image frame, not displaying the designated image frame in the image stream.

For some applications, the method further includes blending into each other a frame that was acquired immediately before acquisition of the designated image frame, and a frame that was acquired immediately after the acquisition of the designated image frame.

For some applications, identifying the feature of the tool includes deriving a feature of the tool from at least one portion of the tool that is generally visible in the image frames.

For some applications, deriving the feature includes deriving a virtual line that connects radiopaque portions of the tool.

For some applications, deriving the feature includes deriving an average location of radiopaque portions of the tool.

For some applications, identifying the feature of the tool includes identifying at least one radiopaque marker of the tool.

For some applications, identifying the marker includes distinguishing between the marker and contrast agent.

For some applications, identifying the marker includes distinguishing between the marker and overlap of a set of two portions of an image frame of the portion of the image frames, the set being selected from the group consisting of two blood vessels, two tool portions, a blood vessel and a tool portion, a blood vessel and a rib, and a tool portion and a rib.

For some applications, identifying the marker includes identifying the marker by accounting for blurring of the marker in a dynamic image stream that is based on the plurality of image frames.

There is further provided, in accordance with some applications of the present invention, apparatus for use with a portion of a subject's body that undergoes motion, the apparatus including:

a tool configured to be placed inside the portion;

an image-acquisition device configured to acquire a plurality of image frames of the portion of the subject's body;

a display; and at least one processor configured to image track the image frames, the processor including:

image-receiving functionality configured to receive the image frames into the processor;

tool-identifying functionality configured to automatically identify at least a feature of the tool in at least a portion of the image frames; and frame-aligning functionality configured to align the tool in image frames of the portion of the image frames, based on the automatic identifying; and display-driving functionality configured to drive the display to display, as an image stream, the image-tracked image frames of the portion of the subject's body.

There is further provided, in accordance with some applications of the present invention, apparatus including:

a sensor for sensing a phase of the cyclic activity;

a tool configured to be deployed within a blood vessel of a subject;

a balloon having a central portion disposed inside the tool and overhanging portions that are disposed outside the tool, the balloon configured to couple the tool to the blood vessel, by the balloon being inflated inside the tool while the balloon and the tool are inside the blood vessel; and a control unit configured, while the balloon and the tool are inside the blood vessel, to inflate the balloon such that at least one of the overhanging portions of the balloon becomes appositioned to an inner surface of the blood vessel, in response to the sensor sensing that the cyclic activity is at a given phase thereof.

For some applications, the control unit is configured to inflate the balloon continuously during at least one period selected from the group consisting of: a period before the balloon becomes appositioned to the surface, and a period after the balloon becomes appositioned to the surface.

For some applications, the tool includes a tool selected from the group consisting of a stent, a replacement valve, and a graft.

There is additionally provided, in accordance with some applications of the present invention, a method for imaging a portion of a body of a subject that undergoes motion, the method including:

acquiring a plurality of image frames of the portion of the subject's body; and generating a stream of image frames in which a vicinity of a given feature of the image frames is enhanced, by:
automatically identifying the given feature in each of the image frames,
aligning the given feature in two or more image frames of the plurality of image frames,
averaging sets of two or more of the aligned frames to generate a plurality of averaged image frames, and
displaying as a stream of image frames the plurality of averaged image frames.

For some applications,
acquiring the plurality of image frames includes acquiring, sequentially, first and second image frames of the portion of the subject's body, and
generating the stream of image frames in which the vicinity of the given feature of the image frames is enhanced includes:
generating a first moving average image frame using frames of the portion of the subject's body acquired prior to the acquisition of the first and second image frames;
aligning the given feature in the first image frame with the given feature in the first moving-average image frame;
when the given feature is aligned in the first image frame and the first moving-average image frame, averaging the first image frame and the first moving-average image frame to generate a second moving-average image frame;
aligning the given feature in the second moving-average image frame and the second image frame;
when the given feature is aligned in the second moving-average image frame and the second image frame, averaging the second image frame with the second moving-average image frame to generate a third moving-average image frame; and
displaying, in an image stream, the first, second, and third moving-average image frames.

There is further provided, in accordance with some applications of the present invention, apparatus for use with a portion of a body of a subject that undergoes motion, the apparatus including:

an image-acquisition device configured to acquire a plurality of image frames of the portion of the subject's body;
a display; and
at least one processor configured to generate a stream of image frames in which a vicinity of a given feature of the image frames is enhanced, the processor including:
image-receiving functionality configured to receive the plurality of image frames into the processor,
feature-identifying functionality configured to automatically identify the given feature in each of the image frames,
image-alignment functionality configured to align the given feature in two or more image frames of the plurality of image frames, and
image-averaging functionality configured to average sets of two or more of the aligned frames to generate a plurality of averaged image frames; and
display-driving functionality configured to drive the display to display, as a stream of image frames, the plurality of averaged image frames.

There is further provided, in accordance with some applications of the present invention, a method for actuating a tool to perform a function on a body of a subject at a given phase of a motion cycle of the subject's body, the method including:
determining a duration of the motion cycle;
in a first motion cycle of the subject, detecting the given phase of the subject's motion cycle; and
actuating the tool to perform the function at a given time after detecting the given phase of the first motion cycle, the given time being determined by subtracting a correction factor from the duration of the motion cycle.

For some applications, determining the duration of the cycle includes determining an average duration of a plurality of motion cycles of the subject.

For some applications, determining the duration of the cycle includes determining a duration of a single previous motion cycle of the subject.

For some applications, the tool includes a valve-placement tool for facilitating placement of a replacement valve, and actuating the tool to perform the function includes actuating the tool to facilitate placement of the valve.

For some applications, the tool includes a valve-repair tool for repairing a valve, and actuating the tool to perform the function includes actuating the tool to repair the valve.

For some applications, the tool includes a balloon, and actuating the tool to perform the function includes actuating the balloon to become inflated.

For some applications, the tool includes a stent, and actuating the tool to perform the function includes actuating the stent to become deployed.

For some applications, the tool includes a graft, and actuating the tool to perform the function includes actuating the graft to become deployed.

For some applications, the correction factor includes a detection-delay correction factor that is associated with a delay between an occurrence of the given phase and detection of the given phase, and actuating the tool to perform the function includes actuating the tool to perform the function at a given time after detecting the given phase of the first motion cycle, the given time being determined by subtracting the detection-delay correction factor from the duration of the motion cycle.

For some applications, the correction factor includes a mechanical-delay correction factor that is associated with a delay between generating a signal to actuate the tool to perform the function and performance of the function by the tool, and actuating the tool to perform the function includes actuating the tool to perform the function at a given time after detecting the given phase of the first motion cycle, the given time being determined by subtracting the mechanical-delay correction factor from the duration of the motion cycle.

There is further provided, in accordance with some applications of the present invention, apparatus for use with a portion of a subject's body that undergoes a motion cycle, including:
a tool configured to perform a function on the portion of the subject's body; and at least one processor, including:

cycle-measuring functionality configured to determine a duration of the motion cycle;

phase-detection functionality configured, in a first motion cycle of the subject, to detect the given phase of the subject's motion cycle; and tool-actuation functionality configured to actuate the tool to perform the function at a given time after the detection of the given phase of the first motion cycle, the given time being determined by subtracting a correction factor from the duration of the motion cycle.

There is additionally provided, in accordance with some applications of the present invention, a method for imaging a portion of a body of a subject that undergoes a motion cycle, the method including:

acquiring a plurality of image frames of the portion of the subject's body; and enhancing the image frames with respect to a first given feature of the image frames, by:

image tracking the image frames with respect to the first given feature;

identifying a second given feature in each of the image frames;

in response to the identifying, reducing visibility of the second given feature in the image frames; and displaying, as a stream of image frames, the image frames that (a) have been image tracked with respect to the first given feature, and (b) have had reduced therein the visibility of the second given feature.

For some applications, reducing the visibility of the second feature includes reducing the visibility by a reduction factor that is a function of a distance of the second feature from the first feature.

For some applications, reducing visibility of the second given feature includes eliminating visibility of the second given feature.

For some applications, as a result of the motion cycle of the portion of the subject's body, the first given feature moves by an amount that is different from an amount of movement of the second given feature as a result of the motion cycle of the portion of the subject's body, and identifying the second feature includes identifying the second feature using a filter selected from the group consisting of a spatial filter and a temporal filter.

There is further provided, in accordance with some applications of the present invention, apparatus for use with a portion of a body of a subject that undergoes a motion cycle, the apparatus including:

an image-acquisition device configured to acquire a plurality of image frames of the portion of the subject's body;

a display; and at least one processor configured to enhance the image frames with respect to a first given feature of the image frames, the processor including:

image-tracking functionality configured to image track the image frames with respect to the first given feature;

feature-identifying functionality configured to identify a second given feature in each of the image frames;

image-processing functionality configured, in response to the identifying, to reduce visibility of the second given feature in the image frames; and display-driving functionality configured to drive the display to display, as a stream of image frames, the image frames that (a) have been image tracked with respect to the first given feature, and (b) have had reduced therein the visibility of the second given feature.

There is additionally provided, in accordance with some applications of the present invention, a method for imaging a portion of a body of a subject that undergoes a motion cycle, the method including:

acquiring a plurality of image frames of the portion of the subject's body;

reducing visibility of a given feature within the image frames by masking the given feature in each of the image frames; and displaying, as a stream of image frames, the image frames in which the given feature has reduced visibility.

For some applications:

masking the given feature in each of the image frames includes generating a plurality of masks, respective masks corresponding to given phases of the motion cycle, and applying the mask to the image frames includes applying to frames of the image stream that were acquired during respective phases of the motion cycle, a corresponding mask.

For some applications:

acquiring the plurality of image frames includes gating the image frames with respect to a given phase of the motion cycle, masking the given feature in each of the image frames includes generating a mask based on an image frame that is gated with respect to the given phase of the motion cycle, and applying the mask to the gated image frames, and displaying the image frames includes displaying the gated, masked image frames.

For some applications, reducing the visibility of the given feature includes reducing the visibility in each of the image frames by a reduction factor that is a function of a distance of the given feature from a given portion of the image frame.

There is further provided, in accordance with some applications of the present invention, apparatus for use with a portion of a body of a subject that undergoes a motion cycle, the apparatus including:

an image acquisition device configured to acquire a plurality of image frames of the portion of the subject's body;

a display; and at least one processor including:

image-receiving functionality configured to receive the image frames into the processor, and masking functionality that is configured to reduce visibility of a given feature within the image frames by masking the given feature in each of the image frames; and display-driving functionality configured to drive the display to display, as a stream of image frames, the image frames in which the given feature has reduced visibility.

For some applications:

the processor includes gating functionality configured to gate the image frames with respect to a given phase of the motion cycle, the masking functionality is configured to generate a mask based on an image frame that is gated with respect to the given phase of the motion cycle, and to apply the mask to the gated image frames, and the display-driving functionality is configured to drive the display to display the gated, masked image frames.

There is additionally provided, in accordance with some applications of the present invention, a method, including:

generating a road map of a blood vessel in a portion of a body of a subject;

identifying, in the road map, a given feature that is within the portion of the subject's body, the given feature being visible even in images of the portion the generation of which does not include use of a contrast agent;

inserting a tool into the blood vessel;

determining a current location of at least a portion of the tool with respect to the given feature, by imaging the tool and the feature;

in response to the determined current location, determining a current position of the tool within the road map; and in response to determining the current position of the tool within the road map, displaying the current position of the tool with respect to the road map.

For some applications, the tool includes a balloon, and inserting the tool includes inserting the balloon.

For some applications, the tool includes a replacement valve, and inserting the tool includes inserting the replacement valve.

For some applications, the tool includes a stent, and inserting the tool includes inserting the stent.

For some applications, the tool includes a wire, and inserting the tool includes inserting the wire.

For some applications, the tool includes a catheter, and inserting the tool includes inserting the catheter.

For some applications, generating the road map includes generating a road map based upon a given phase of a motion cycle of the blood vessel, and determining the current location of the portion of the tool includes determining the current location of the portion of the tool during the given phase.

There is further provided, in accordance with some applications of the present invention, apparatus, including:
a tool configured to be inserted into a blood vessel of a portion of a body of a subject;
a display; and
at least one processor, including:
road-map-generation functionality configured to generate a road map of the blood vessel in the portion of the subject's body;
feature-identifying functionality configured to identify, in the road map, a given feature that is within the portion of the subject's body, the given feature being visible even in images of the portion the generation of which does not include use of a contrast agent;
tool-location functionality configured to determine a current location of at least a portion of the tool with respect to the given feature, based on a current image of the tool and the feature;
tool-positioning functionality configured, in response to the determined current location of the tool, to determine a current position of the tool within the road map; and
display-driving functionality configured, in response to determining the current position of the tool within the road map, to drive the display to display the current position of the tool with respect to the road map.

There is additionally provided, in accordance with some applications of the present invention, a method, including:
generating a road map of a blood vessel in a portion of a body of a subject;
identifying, in the road map, a given feature that is within the portion of the subject's body, the given feature being visible even in images of the portion the generation of which does not include use of a contrast agent;
generating an image stream of the blood vessel;
identifying the given feature in the image stream;
registering the road map to the image stream using the identified feature; and
in response to the registration of the road map to the image stream, overlaying the road map on the image stream.

There is further provided, in accordance with some applications of the present invention, apparatus, including:
a tool configured to be inserted into a blood vessel of a portion of a body of a subject;

an image-acquisition device configured to acquire an image stream of the blood vessel;
a display; and
at least one processor, including:
image-receiving functionality configured to receive the image stream into the processor;
road-map-generation functionality configured to generate a road map of the blood vessel in the portion of the subject's body;
road-map-feature-identifying functionality configured to identify, in the road map, a given feature that is within the portion of the subject's body, the given feature being visible even in images of the portion the generation of which does not include use of a contrast agent;
image-stream-feature-identifying functionality configured to identify the feature in the image stream;
registration-functionality configured to register the road map to the image stream using the identified feature; and
display-driving functionality configured, in response to the registration of the road map to the image stream, to drive the display to overlay the road map on the image stream.

There is additionally provided, in accordance with some applications of the present invention, a method for use with a portion of a subject's body that assumes a plurality of different shapes, during respective phases of a motion cycle of the portion, the method including:
acquiring a plurality of image frames of the portion of the subject's body during the respective phases of the motion cycle of the portion;
designating at least one of the image frames as a baseline image frame, a shape of the portion in the baseline image frame being designated as a baseline shape of the portion;
identifying a non-baseline image frame of the plurality of image frames, by identifying an image frame in which the portion is not shaped in the baseline shape; and
deforming the shape of the portion in the non-baseline image frame, such that the shape of the portion becomes more similar to the baseline shape of the portion than when the portion in the non-baseline image frame is not deformed; and
subsequently to deforming the shape of the portion in the non-baseline image frame, displaying the baseline image frame and the non-baseline image frame in an image stream.

There is further provided, in accordance with some applications of the present invention, apparatus for use with a portion of a subject's body that assumes a plurality of different shapes, during respective phases of a motion cycle of the portion, the apparatus including:
an image-acquisition device configured to acquire a plurality of image frames of the portion of the subject's body during the respective phases of the motion cycle of the portion;
a display; and
at least one processor, including:
image-receiving functionality configured to receive the image frames into the processor,
baseline-designation functionality configured to designate at least one of the image frames as a baseline image frame, a shape of the portion in the baseline image frame being designated as a baseline shape of the portion;
non-baseline identification functionality configured to identify a non-baseline image frame of the plurality of image frames, by identifying an image frame in which the portion is not shaped in the baseline shape; and
shape-deformation functionality configured to deform the shape of the portion in the non-baseline image frame, such that the shape of the portion becomes more similar to the baseline shape of the portion than when the portion in the non-baseline image frame is not deformed; and display-driving functionality configured, subsequently to the deforming of the shape of the portion in the non-baseline image frame, to drive the display to display the baseline image frame and the non-baseline image frame in an image stream.

There is additionally provided, in accordance with some applications of the present invention, a method for deploying an implantable tool at an implantation location of a blood vessel of a subject, including:

placing the tool at the implantation location, while the tool is in a non-deployed configuration;

while the tool in the non-deployed configuration is disposed at the implantation location, acquiring a plurality of image frames of the tool, during respective phases of a motion cycle of the blood vessel;

generating a stabilized image stream of the tool in the non-deployed configuration, by stabilizing the plurality of image frames;

determining from the stabilized image stream that, during the motion cycle of the blood vessel, the tool moves from the implantation location by a given distance in a first direction; and accounting for the movement of the tool by the given distance, by deploying the tool at a deployment location that is distant from the implantation location in a second direction, the second direction being an opposite direction to the first direction.

For some applications, accounting for the movement of the tool by the given distance includes deploying the tool at a deployment location that is at the given distance from the implantation location in the second direction.

For some applications, accounting for the movement of the tool by the given distance includes deploying the tool at a deployment location that is at a distance from the implantation location in the second direction that is greater than the given distance.

For some applications, accounting for the movement of the tool by the given distance includes deploying the tool at a deployment location that is at a distance from the implantation location in the second direction that is less than the given distance.

For some applications, the tool includes a tool selected from the group consisting of a stent, a replacement valve, and a graft, and placing the tool at the implantation location includes placing the selected tool at the implantation location.

There is further provided, in accordance with some applications of the present invention, apparatus for deploying, including:

an implantable tool configured to be placed at an implantation location of a blood vessel of a subject, while the tool is in a non-deployed configuration;

an image acquisition device configured, while the tool is disposed at the implantation location in a non-deployed configuration, to acquire a plurality of image frames of the tool, during respective phases of a motion cycle of the blood vessel;

a display; and at least one processor, including:
image-stabilization functionality configured to generate a stabilized image stream of the tool in the non-deployed configuration, by stabilizing the plurality of image frames;
motion-determination functionality configured to determine based on the stabilized image stream that, during the motion cycle of the blood vessel, the tool moves from the implantation location by a given distance in a first direction; and
deployment-location functionality configured to determine a deployment location for the tool that is distant from the implantation location in a second direction, by accounting for the movement of the tool by the given distance, the second direction being an opposite direction to the first direction; and
display-driving functionality configured to drive the display to display an output indicating the deployment location.

There is further provided, in accordance with some applications of the present invention, apparatus for use with a portion of a body of a subject that undergoes cyclic motion, the apparatus including:

a sensor for sensing a phase of the cyclic motion;

a tool at least a portion of which is configured to be moved with respect to the portion of the subject's body; and a tool modulator configured:
during a first phase of a first cycle of the cyclic motion, not to facilitate movement of the portion of the tool,
subsequent to the first phase of the first cycle, in response to the sensor sensing that the first cycle of the cyclic motion is at a second phase thereof, to facilitate movement of the portion of the tool, and
in a cycle subsequent to the first cycle, to facilitate movement of the portion of the tool, during the entire subsequent cycle;

an accumulation-facilitator configured, during the first phase of the first cycle, to facilitate an accumulation of energy in the accumulation facilitator; and an accumulation-inhibitor configured to inhibit accumulation of energy in the accumulation-facilitator during the subsequent cycle, by actively inhibiting movement of at least a portion of the accumulation-facilitator.

For some applications, the tool includes a balloon, at least a portion of which is configured to be inflated in response to the sensor sensing that the first cycle of the cyclic motion is at the second phase thereof.

For some applications, the apparatus further includes inflation fluid, the balloon being configured to be inflated with the inflation fluid, the accumulation-facilitator includes a surface configured to facilitate an accumulation of energy by moving in response to pressure from the inflation fluid, and the accumulation-inhibitor is configured to inhibit the movement of the surface during the subsequent cycle.

For some applications, the surface is configured to facilitate the accumulation of energy by becoming elastically deformed.

For some applications, the apparatus further includes a spring, and the surface is configured to facilitate an accumulation of energy by facilitating an accumulation of energy in the spring.

For some applications, in response to the sensor sensing that the first cycle of the cyclic motion is at the second phase thereof,
the surface is configured to automatically release at least some of the accumulated energy by applying pressure to the inflation fluid, and
the accumulation-inhibitor is configured to move automatically such that the accumulation inhibitor inhibits movement of the surface.

For some applications, the accumulation inhibitor is configured to assist in the release of energy from the surface by moving automatically.

There is additionally provided, in accordance with some applications of the present invention, apparatus for use with a portion of a body of a subject that undergoes cyclic motion, the apparatus including:

a sensor for sensing a phase of the cyclic motion;

a tool at least a portion of which is configured to be moved with respect to the portion of the subject's body; and a tool modulator configured:

during a first phase of a first cycle of the cyclic motion, not to facilitate movement of the portion of the tool, subsequent to the first phase of the first cycle, in response to the sensor sensing that the first cycle of the cyclic motion is at a second phase thereof, to facilitate movement of the portion of the tool, and in a cycle subsequent to the first cycle, to facilitate movement of the portion of the tool, during the entire subsequent cycle;

an accumulation facilitator configured, during the first phase of the first cycle, to facilitate an accumulation of energy in the accumulation facilitator; and an accumulation-bypass mechanism configured to cause the accumulation facilitator to be bypassed during the subsequent cycle.

For some applications, the tool includes a balloon, at least a portion of which is configured to be inflated in response to the sensor sensing that the first cycle of the cyclic motion is at the second phase thereof.

For some applications, the apparatus further includes inflation fluid, the balloon being configured to be inflated with the inflation fluid, the accumulation-facilitator includes a surface configured to facilitate an accumulation of energy by moving in response to pressure from the inflation fluid, and the accumulation-bypass mechanism is configured to cause the inflation fluid not to flow past the surface during the subsequent cycle.

For some applications, the surface is configured to facilitate the accumulation of energy by becoming elastically deformed.

For some applications, the apparatus further includes a spring, and the surface is configured to facilitate an accumulation of energy by facilitating an accumulation of energy in the spring.

There is further provided, in accordance with some applications of the present invention, a method for actuating a balloon to become inflated inside a blood vessel of a subject, at least a portion of the inflation being at a given phase of a motion cycle of the subject's body, the method including:

placing the balloon at a location inside the blood vessel, a distal portion of a catheter being coupled to the balloon, the catheter being configured to provide fluid communication between the balloon and an inflation device;

detecting a physiological signal of the subject that is associated with a change in the pressure at the location of the balloon inside the blood vessel;

detecting the change in pressure at a proximal portion of the catheter;

determining a pressure-propagation-delay correction factor associated with the catheter by determining a time difference between the detection of the physiological signal and the detection of the change in pressure at the proximal portion of the catheter; and determining a duration of the motion cycle; and, subsequently, in a first motion cycle of the subject, detecting the given phase of the subject's motion cycle; and actuating the balloon to become inflated at a given time after detecting the given phase of the first motion cycle, the given time being determined in response to the pressure-propagation-delay correction factor and the duration of the motion cycle.

There is further provided, in accordance with some applications of the present invention, apparatus including:

a sensor for sensing a phase of the cyclic activity;

a tool configured to be deployed within a blood vessel of a subject;

a balloon having a central portion disposed inside the tool and overhanging portions that are disposed outside the tool, the balloon configured to couple the tool to the blood vessel, by the balloon being inflated inside the tool while the balloon and the tool are inside the blood vessel; and a control unit configured, while the balloon and the tool are inside the blood vessel, to inflate the balloon such that at least one of the overhanging portions of the balloon becomes appositioned to an inner surface of the blood vessel, in response to the sensor sensing that the cyclic activity is at a given phase thereof.

For some applications, the control unit is configured to inflate the balloon continuously during at least one period selected from the group consisting of: a period before the balloon becomes appositioned to the surface, and a period after the balloon becomes appositioned to the surface.

For some applications, the tool includes a tool selected from the group consisting of a stent, a replacement valve, and a graft.

There is further provided, in accordance with some applications of the present invention, a method for use with a portion of a body of a subject that undergoes cyclic motion, the method including:

sensing a phase of the cyclic motion;

during a first phase of a first cycle of the cyclic motion, (a) not facilitating movement of a portion of a tool with respect to the portion, and (b) facilitating an accumulation of energy in an accumulation-facilitator, subsequent to the first phase of the first cycle, in response to sensing that the first cycle of the cyclic motion is at a second phase thereof, facilitating movement of the portion of the tool, and in a cycle subsequent to the first cycle, (a) facilitating movement of the portion of the tool, during the entire subsequent cycle, and (b) inhibiting accumulation of energy in the accumulation-facilitator, by actively inhibiting movement of at least a portion of the accumulation-facilitator.

There is additionally provided, in accordance with some applications of the present invention a method for use with a portion of a body of a subject that undergoes cyclic motion, the method including:

sensing a phase of the cyclic motion;

during a first phase of a first cycle of the cyclic motion, (a) not facilitating movement of a portion of a tool with respect to the portion, and (b) facilitating an accumulation of energy in an accumulation-facilitator, subsequent to the first phase of the first cycle, in response to sensing that the first cycle of the cyclic motion is at a second phase thereof, facilitating movement of the portion of the tool, and in a cycle subsequent to the first cycle, (a) facilitating movement of the portion of the tool, during the entire subsequent cycle, and (b) inhibiting accumulation of energy in the accumulation-facilitator, by causing the accumulation facilitator to be bypassed.

There is further provided, in accordance with some applications of the present invention, apparatus for use with (a) a balloon configured to become inflated inside a blood vessel of a subject, at least a portion of the inflation being at a given phase of a motion cycle of the subject, (b) an inflation device configured to inflate the balloon, and (c) a catheter a distal portion of which is coupled to the balloon, the catheter providing fluid communication between the balloon and the inflation device, the apparatus including:

at least one physiological sensor configured to detect (a) a physiological signal of the subject that is associated with a change in the pressure at the location of the balloon inside the blood vessel, (b) a duration of the motion cycle, and (c) the given phase of the subject's motion cycle;

a pressure sensor configured to be placed at a proximal portion of the catheter, and to detect the change in pressure at the proximal portion of the catheter; and at least one processor, configured:
in response to the detection of the physiological signal and the change in pressure, to:
determine a pressure-propagation-delay correction factor associated with the catheter by determining a time difference between the detection of the physiological signal and the detection of the change in pressure at the proximal portion of the catheter; and,
subsequently, in a first motion cycle of the subject, in response to the physiological sensor detecting the given phase of the subject's motion cycle, to
actuate the balloon to become inflated at a given time after detecting the given phase of the first motion cycle, the given time being determined in response to the pressure-propagation-delay correction factor and the detected duration of the motion cycle.

There is further provided, in accordance with some applications of the present invention, a method for use with a tool configured to be deployed within a blood vessel of a subject, and a balloon having a central portion disposed inside the tool and overhanging portions that are disposed outside the tool, the balloon being configured to couple the tool to the blood vessel, by the balloon being inflated inside the tool while the balloon and the tool are inside the blood vessel, the method including:

sensing a phase of the cyclic activity; and
while the balloon and the tool are inside the blood vessel, inflating the balloon such that at least one of the overhanging portions of the balloon becomes appositioned to an inner surface of the blood vessel, in response to the sensing that the cyclic activity is at a given phase thereof.

There is additionally provided, in accordance with some applications of the present invention, apparatus for use with a portion of a body of a subject that undergoes cyclic motion, the apparatus including:

a sensor for sensing a phase of the cyclic motion;
a tool at least a portion of which is configured to be moved with respect to the portion of the subject's body;
a tool-actuation element configured to actuate the tool to move; and
a tool modulator configured:
during a first phase of a first cycle of the cyclic motion, not to facilitate movement of the portion of the tool,
subsequent to the first phase of the first cycle, in response to the sensor sensing that the first cycle of the cyclic motion is at a second phase thereof, to facilitate movement of the portion of the tool, and
in a cycle subsequent to the first cycle, to facilitate movement of the portion of the tool, during the entire subsequent cycle;
an accumulation-facilitator configured, during the first phase of the first cycle, to facilitate an accumulation of the tool-actuation element in the accumulation facilitator; and
an accumulation-inhibitor configured to inhibit accumulation of the tool-actuation element in the accumulation-facilitator during the subsequent cycle, by actively inhibiting movement of at least a portion of the accumulation-facilitator.

For some applications, the tool includes a balloon, at least a portion of which is configured to be inflated in response to the sensor sensing that the first cycle of the cyclic motion is at the second phase thereof, and the tool-actuation element includes inflation fluid, the balloon being configured to be inflated with the inflation fluid.

For some applications,
the accumulation-facilitator includes a chamber, a surface of which chamber is configured to facilitate an accumulation of the inflation fluid in the chamber by the surface being disposed in a first position with respect to the chamber,
the surface is configured to release at least a portion of the accumulated inflation fluid by moving to a second position with respect to the chamber, and
the accumulation-inhibitor is configured to inhibit the accumulation of the inflation fluid in the chamber, by inhibiting movement of the surface from the second position with respect to the chamber, during the subsequent cycle.

There is further provided, in accordance with some applications of the present invention, a method for use with a portion of a body of a subject that undergoes cyclic motion, the method including:

sensing a phase of the cyclic motion;
during a first phase of a first cycle of the cyclic motion, (a) not facilitating movement of a portion of a tool with respect to the portion, and (b) facilitating an accumulation of a tool-actuation element in an accumulation-facilitator,
subsequent to the first phase of the first cycle, in response to sensing that the first cycle of the cyclic motion is at a second phase thereof, facilitating movement of the portion of the tool, by releasing at least a portion of the accumulated tool-actuation element, and
in a cycle subsequent to the first cycle, (a) facilitating movement of the portion of the tool, during the entire subsequent cycle, and (b) inhibiting accumulation of the tool-actuation element in the accumulation-facilitator, by actively inhibiting movement of at least a portion of the accumulation-facilitator.

There is additionally provided, in accordance with some applications of the present invention, apparatus, including:

a display configured to display an image of one or more lumens of a subject;
an input device; and
at least one processor, including:
lumen-identification functionality configured to automatically identify one or more lumens in the image;
envelope-designation functionality configured to designate as lumen envelopes, portions of the image in vicinities of respective lumens;
feature-generation functionality configured,
in response to the user designating a location inside a lumen envelope of a given lumen, via the input device, the location corresponding to a given longitudinal location within the given lumen,
to generate a feature on the image that corresponds to the given longitudinal location; and
display-driving functionality configured to drive the display to display an output in response to the generated feature.

For some applications, the one or more lumens include one or more blood vessels, and the feature-generation functionality is configured to generate a feature that corresponds to a longitudinal location of a given blood vessel.

For some applications, the feature-generation functionality is configured to generate the feature in response to the user designating the location by moving a cursor to the location, via the input device.

For some applications, the feature-generation functionality is configured to generate the feature adjacent to the lumen at the longitudinal location.

For some applications, the feature-generation functionality is configured to generate, as the feature, an indication of an extent of a narrowing of the lumen at the longitudinal location.

For some applications, the feature-generation functionality is configured to generate, as the feature, an alphanumeric indication of the extent of the narrowing of the lumen at the longitudinal location.

For some applications, the feature-generation functionality is configured to generate, as the feature, an indication of a diameter of the lumen at the longitudinal location.

For some applications, the feature-generation functionality is configured to generate, as the feature, an alphanumeric indication of the diameter of the lumen at the longitudinal location.

For some applications, the feature-generation functionality is configured to generate the feature inside the vessel at the longitudinal location.

For some applications, the feature-generation functionality is configured to generate, as the feature, a line, a length of which indicates a diameter of the lumen at the longitudinal location.

For some applications, the processor further includes segment-identification functionality configured, in response to the user designating the location inside the lumen envelope of the given lumen, via the input device, to automatically identify a segment of the given lumen that corresponds to the location.

For some applications, the feature-generation functionality is configured to generate, as the feature, an indication of a minimum lumen diameter of the segment.

For some applications, the feature-generation functionality is configured to generate, as the feature, an indication of reference diameters of the segment.

There is further provided, in accordance with some applications of the present invention, apparatus, including:
a display configured to display an image of lumens of a subject's body;
an input device; and
at least one processor, including:
lumen-identification functionality configured to automatically identify a plurality of lumens in the image;
envelope-designation functionality configured to designate as lumen envelopes, portions of the image in the vicinity of respective lumens;
segment-identification functionality configured,
in response to the user designating a location inside a lumen envelope of a given lumen, via the input device, to automatically identify a segment of the given lumen that corresponds to the location; and
display-driving functionality configured to drive the display to display an output in response to the identified segment.

For some applications, the segment-identification functionality is configured to identify the segment in response to the user designating the location by moving a cursor to the location, via the input device.

For some applications, the segment-identification functionality is configured to identify the segment by automatically determining locations of a center line and edge lines of the segment.

For some applications, the segment-identification functionality is configured to identify the segment by automatically determining locations of reference diameters of the segment.

For some applications, the lumens include blood vessels, and the segment-identification functionality is configured to identify a segment of a blood vessel.

For some applications, the blood vessels include a main vessel and a plurality of side-branches, and the segment-identification functionality is configured to identify a segment that includes a portion of one of the side branches and a portion of the main vessel.

There is further provided, in accordance with some applications of the present invention, apparatus, including:
a display configured to display an image of lumens of a subject's body;
an input device; and
at least one processor, including:
display-driving functionality configured to drive the display to display a feature in the image, in a vicinity of one of the lumens on the image; and
feature-control functionality configured (a) in response to receiving an input from a user, via the input device, indicating that the feature should be moved, (b) only to allow movement of the feature along directions of paths of the lumens.

For some applications, the lumens include blood vessels, and the feature-control functionality is configured to only allow movement of the feature along directions of paths of the blood vessels.

For some applications, the feature-control functionality is configured to only allow movement of the feature within the lumens along the directions of the paths.

For some applications, the feature-control functionality is configured to only allow movement of the feature alongside the lumens, along the directions of the paths.

For some applications, the feature includes a cursor, and the feature-control functionality includes cursor-control functionality configured to only allow movement of the cursor along the directions of the paths of lumens.

For some applications, the processor further includes derived-feature-generation functionality configured, in response to the user designating a location in a vicinity of a given lumen, via the input device, the location corresponding to a given longitudinal location within the given lumen, to generate a derived-feature on the image at a location that corresponds to the given longitudinal location, and the feature-control functionality is configured only to allow movement of the derived-feature along the directions of the paths of the lumens.

There is additionally provided, in accordance with some applications of the present invention, apparatus, including:
a display configured to display an image of lumens of a subject's body;
an input device; and
at least one processor, including:
lumen-identification functionality configured, in response to a user moving a cursor to a given location on the image via the input device, to automatically identify a lumen in the image by interpreting the movement of the cursor to the location as indicating that there is a greater probability that there is a lumen in the vicinity of the location of the cursor than in another portion of the image; and display-driving functionality configured to drive the display to display an output in response to the identified lumen.

For some applications, the lumen-identification functionality is configured to:
assign vesselness values to respective regions of the image, the vesselness values indicating probabilities that respective regions correspond to a lumen, and
assign different weightings to vesselness values of regions in the vicinity of the location of the cursor from weightings assigned to vesselness values of regions in the other portion of the image.

There is further provided, in accordance with some applications of the present invention, a method, including:
displaying an image of one or more lumens of a subject;
automatically identifying one or more lumens in the image;
designating as lumen envelopes, portions of the image in vicinities of respective lumens; and
in response to a user designating a location inside a lumen envelope of a given lumen, via an input device, the location corresponding to a given longitudinal location within the given lumen,
generating a feature on the image that corresponds to the given longitudinal location; and
displaying an output in response to the generated feature.

There is additionally provided, in accordance with some applications of the present invention, a method, including:
displaying an image of lumens of a subject's body;
automatically identifying a plurality of lumens in the image;
designating as lumen envelopes, portions of the image in the vicinity of respective lumens; and
in response to the user designating a location inside a lumen envelope of a given lumen, via the input device,
automatically identifying a segment of the given lumen that corresponds to the location; and
displaying an output in response to the identified segment.

There is further provided, in accordance with some applications of the present invention, a method, including:
displaying an image of lumens of a subject's body;
displaying a feature in the image, in a vicinity of one of the lumens on the image;
receiving an input from a user, via an input device, indicating that the feature should be moved; and
in response to receiving the input, only allowing movement of the feature along directions of paths of the lumens.

There is additionally provided, in accordance with some applications of the present invention, a method, including:
displaying an image of lumens of a subject's body;
in response to a user moving a cursor to a given location on the image via an input device, automatically identifying a lumen in the image, by interpreting the movement of the cursor to the location as indicating that there is a greater probability that there is a lumen in the vicinity of the location of the cursor than in another portion of the image; and
displaying an output in response to the identified lumen.

There is further provided, in accordance with some applications of the present invention, a method for use with a tool that is inserted into a portion of a body of a subject that undergoes cyclic motion, the method including:
acquiring a plurality of native images of the tool inside the portion of the body, at respective phases of the cyclic motion;
stabilizing the native images with respect to a feature of the portion of the body; and
in response to stabilizing the native images, generating an output that is indicative of an extent of movement of the tool with respect to the portion of the body.

For some applications, generating the output includes generating an alphanumeric output.

For some applications, generating the output includes demonstrating movement of the tool with respect to the portion of the body by displaying at least one stabilized image that is based upon the stabilized raw images, an indication of the movement being displayed on the at least one stabilized image For some applications, stabilizing the images includes tracking the images with respect to the feature, and combining the images into a single image, and demonstrating the movement of the tool with respect to the portion includes demonstrating the movement of the tool by virtue of displaying the single image.

For some applications, stabilizing the images includes tracking the images with respect to the feature, and generating a tracked image stream, and demonstrating the movement of the tool with respect to the portion includes demonstrating the movement of the tool by virtue of displaying the image stream.

For some applications, the method further includes enhancing the images, and displaying the stabilized image includes displaying at least one stabilized and enhanced image.

For some applications, the method further includes determining movement of the tool with respect to the portion of the body, by determining motion of images belonging to the plurality of images with respect to each other, and demonstrating movement of the tool with respect to the portion includes overlaying an indication of the movement of the tool onto the stabilized image.

There is further provided, in accordance with some applications of the present invention, apparatus for use with a portion of a subject's body that assumes a plurality of different shapes, during respective phases of a motion cycle of the portion, the apparatus including:
an image-acquisition device configured to acquire a plurality of image frames of the portion of the subject's body during the respective phases of the motion cycle of the portion;
a display; and
at least one processor, including:
image-receiving functionality configured to receive the image frames into the processor,
baseline-designation functionality configured to designate at least one of the image frames as a first baseline image frame, a shape of the portion in the baseline image frame being designated as a first baseline shape of the portion;
non-baseline-shape identification functionality configured to identify a first non-baseline-shape image frame of the plurality of image frames, by identifying an image frame in which the portion is not shaped in the first baseline shape; and
shape-deformation functionality configured to deform the shape of the portion in the non-baseline-shape image frame, such that the shape of the portion becomes more similar to the first baseline shape of the portion than when the portion in the non-baseline-shape image frame is not deformed; and
display-driving functionality configured, in response to the deforming of the shape of the portion in the non-baseline-shape image frame, to drive the display to display an output.

For some applications, the processor further includes image-combination functionality configured to form at least a first composite image by combining the deformed non-baseline image frame with the baseline image frame, and the display-driving functionality is configured to drive the display to display the first composite image.

For some applications:
the baseline-designation functionality is configured to designate at least one of the image frames as a second baseline image frame, a shape of the portion in the second baseline image frame being designated as a second baseline shape of the portion;
the non-baseline identification functionality is configured to identify a second non-baseline image frame of the plurality of image frames, by identifying an image frame in which the portion is not shaped in the second baseline shape;
the shape-deformation functionality is configured to deform the shape of the portion in the second non-baseline image frame, such that the shape of the portion becomes more similar to the second baseline shape of the portion than when the portion in the second non-baseline image frame is not deformed;
the image-combination functionality is configured to form a second composite image by combining the deformed second non-baseline image frame with the second baseline image frame; and
the display-driving functionality is configured to drive the display to display the first and second composite images as an image stream.

There is further provided, in accordance with some applications of the present invention, apparatus for use with a tool that is inserted into a portion of a body of a subject that undergoes cyclic motion, the apparatus including:
a display configured to display at least one image of the portion of the subject's body;
an imaging device configured to acquire a plurality of native images of the tool inside the portion of the body, at respective phases of the cyclic motion; and
at least one processor, including:
image-receiving functionality configured to receive the image frames into the processor,
image-stabilization functionality configured to stabilize the native images with respect to a feature of the portion of the body; and
display-driving functionality configured, in response to the image-stabilization of the native images, to drive the display to display an output that is indicative of an extent of movement of the tool with respect to the portion of the body.

For some applications, the processor further includes image-enhancement functionality configured to enhance the images, and the display-driving functionality is configured to drive the display to display at least one stabilized and enhanced image.

There is further provided, in accordance with some applications of the present invention, a method for use with a portion of a subject's body that assumes a plurality of different shapes, during respective phases of a motion cycle of the portion, the method including:
acquiring a plurality of image frames of the portion of the subject's body during the respective phases of the motion cycle of the portion;
designating at least one of the image frames as a first baseline image frame, a shape of the portion in the baseline image frame being designated as a first baseline shape of the portion;
identifying a first non-baseline-shape image frame of the plurality of image frames, by identifying an image frame in which the portion is not shaped in the first baseline shape;
deforming the shape of the portion in the non-baseline-shape image frame, such that the shape of the portion becomes more similar to the first baseline shape of the portion than when the portion in the non-baseline-shape image frame is not deformed; and
in response to the deforming of the shape of the portion in the non-baseline-shape image frame, displaying an output.

The present invention will be more fully understood from the following detailed description of embodiments thereof, taken together with the drawings, in which:

BRIEF DESCRIPTION OF THE DRAWINGS

FIG. 16 is a schematic illustration of a screen on which quantitative vessel analysis (QVA) is displayed with respect to a segment of a vessel that is part of a road map, in accordance with some applications of the present invention;

FIGS. 23B-C show apparatus for facilitating synchronized inflation of a balloon, in accordance with some applications of the present invention;

FIG. 24 shows an image of an inflated coronary balloon that is enhanced, in accordance with some applications of the present invention;

FIGS. 39A, 39B, 39C and 39D are schematic illustrations of an accumulator-modulator for facilitating the synchronized inflation of a balloon, in accordance with some applications of the present invention.

DETAILED DESCRIPTION OF EMBODIMENTS

Terminology

Figure 1:
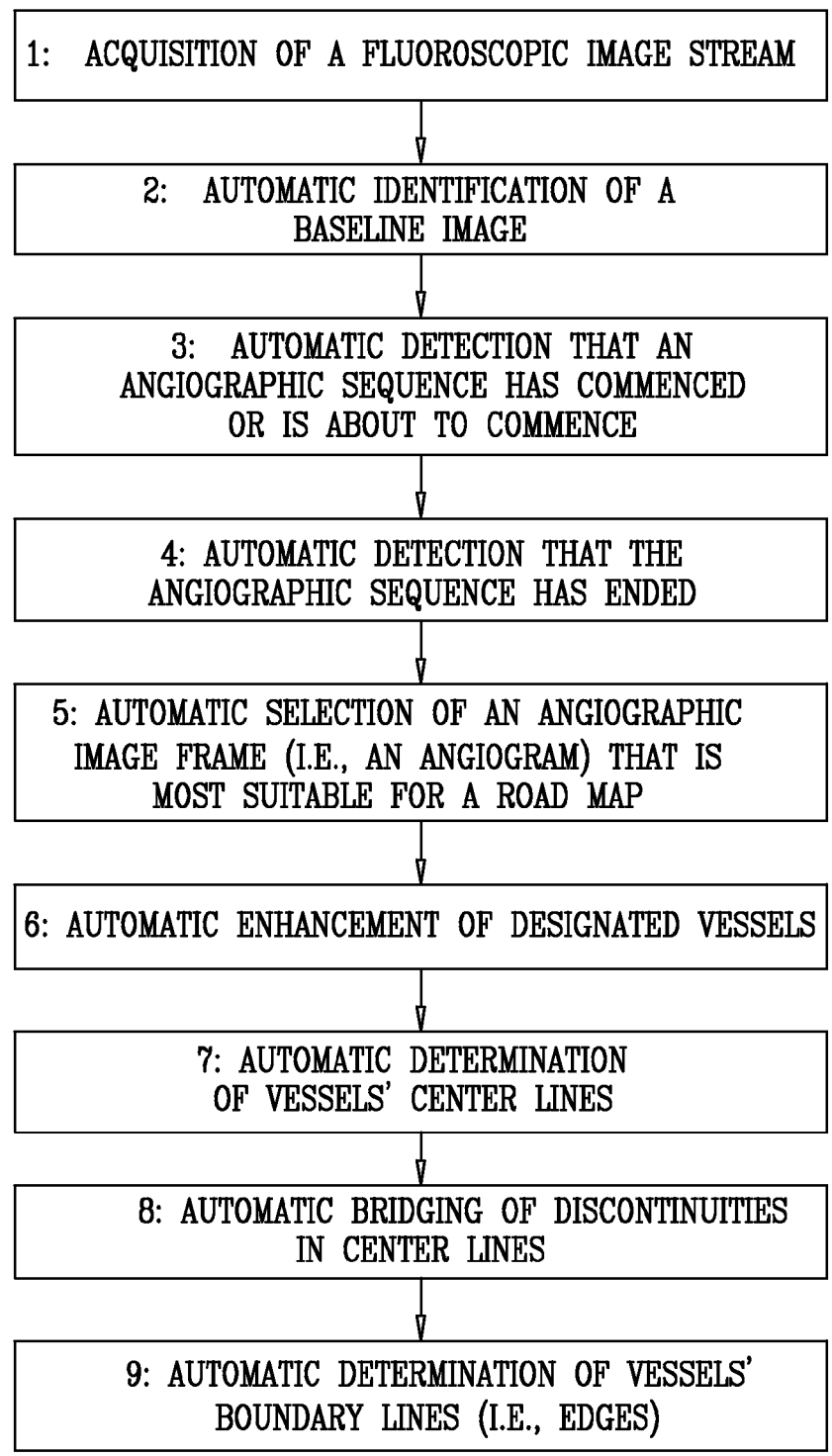
FIG. 1 is a flow chart, at least some of the steps of which are used to automatically generate a road map, in accordance with some applications of the present invention.

As used herein:

The term "physiological signal or process" refers to any physiological signal or process of the subject's body including, but not limited to, ECG (also known as EKG), blood pressure (e.g., systolic and diastolic), Peripheral Arterial Tone (PAT), EEG, respiration, the shifting/expansion/contraction/displacement of an organ, acquired images in which any of the above signals or processes may be observed, or any combination, derivation, extrapolation or manipulation thereof.

(Typically, a Physiological Signal or Process as Described Herein is Cyclical.)

The terms "medical tool," "tool", "device," and "probe" refer to any type of a diagnostic or therapeutic or other functional tool including, but not limited to, a cardiovascular catheter, a stent delivery and/or placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, or any combination thereof.

The terms "image" and "imaging" refer to any type of medical imaging, typically presented as a sequence of images and including, but not limited to, imaging using ionizing radiation, imaging using non-ionizing radiation, video, fluoroscopy, angiography, ultrasound, CT, MRI, PET, PET-CT, CT angiography, SPECT, Gamma camera imaging, Optical Coherence Tomography (OCT), Near-Infra-Red Spectroscopy (NIRS), Vibration Response Imaging (VRI), Optical Imaging, infrared imaging, electrical mapping imaging, other forms of Functional Imaging, or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof.

The terms "synchronization" and "gating," and derivations thereof, when used in reference to an image stream, describe the identification and selection of individual image frames from such image stream, wherein such frames are acquired at a same selected phase in a plurality of occurrences of a cyclical physiological signal or process.

The terms "gating" and "synchronization," and derivations thereof, when used in the context of synchronizing between an image display and one or more physiological signals or processes, or between the activation of a medical tool and one or more physiological signals or processes, are interchangeable. (The term "coherence" and derivations thereof are also used in the art to describe such techniques.)

The terms "gating" and "synchronization," and derivations thereof, when used in reference to a medical tool, describes the movement and/or application of the tool at a given phase of a cyclical physiological signal or process.

The terms "image tracking" or "tracking," and derivations thereof, are used to describe a process by which images (including images acquired at different phases in the motion of an organ) are at least partially aligned with one another by means of aligning among such images one or more features that are observable in most or all of the images. Such features may be anatomical features, such as a segment of a vessel. Such features may also be physical features, such as a tool or a segment of a tool. For some applications, the alignment of the image frames is achieved by aligning a virtual feature or region that is derived from a manipulation (such as an average, a weighted average, a translation, a rotation, and/or a scaling) of the locations of one or more observable features or regions of the image frames. The term should be construed to be synonymous with the terms "video tracking," "frame tracking," and "object tracking" Tracking may be applied for the purpose of image stabilization, image enhancement, or a combination thereof.

The term "automatic," when used for describing the generation and utilization of the road map, means "without necessitating user intervention or interaction."
(Such interaction or intervention may still however be optional in some cases.)

The term "real time" means without a noticeable delay.

The term "near real time" means with a short noticeable delay (such as approximately one or two motion cycles of the applicable organ, and, in the case of procedures relating to organs or vessels the motion of which are primarily as a result of the cardiac cycle, less than two seconds).

The term "on-line," when used in reference to image processing, or to measurements being made on images, means that the image processing is performed, and/or the measurements are made, intra-procedurally, in real time or near real time.

The term "stepwise," when used in reference to the actuation of a tool, should be interpreted as "in two or more steps which are separated in time."

The term "image stream" should be interpreted to mean the display of at least five image frames at a frame rate such that the image frames in effect show a movie of a portion of a subject's body undergoing at least one entire motion cycle. An image stream of a portion of a subject's body undergoing a motion cycle typically has a frame rate of at least 1 frame per motion cycle. In the case of a cardiac motion cycle, therefore, the image stream typically has a frame rate of at least 0.5 Hz (for a slow heart rate). In the case of cardiac and non-cardiac motion cycles, the frame rate is typically 1-10 frames per motion cycle, or higher.

Identification of Vessel Boundaries and the Generation of a Road Map

Reference is now made to FIG. 1, which is a flow chart, at least some of the steps of which are used to automatically generate a road map, in accordance with some applications of the present invention. The automatic generation of a road map is described with reference to coronary angiography, by way of example. The scope of the present invention includes the automatic generation of a road map using a different imaging modality.

In Phase 1 of the automatic road map generation, a fluoroscopic image stream of the coronary arteries is acquired. Typically, during the acquisition of the image stream, a contrast agent is administered to the subject. Optionally, the image stream is gated, tracked, and/or stabilized by other means. For example, selected image frames corresponding to a given phase in the motion cycle of the heart may be identified by means of a physiological signal. For some applications, the physiological signal applied is the subject's ECG and the image frames are selected by means of gating to the ECG and/or by other means of gating as described in WO 08/107,905 to Iddan, which is incorporated herein by reference. It is noted that stabilization of the image stream is optional and, for some applications, a road map is automatically generated on a native (non-stabilized) fluoroscopic image stream.

For some applications, the ECG signal is received from an ECG monitor. Alternatively or additionally, the ECG signal is received from a Cardiac Rhythm Management (CRM) device such as a pacer, or a defibrillator. For some applications, a processor that performs the automatic generation of the road map, or a dedicated processor, identifies the selected phase of the ECG signal. (In general, in the present application, when references are made to the functionalities of a processor, the functionalities may be performed by a single processor, or by several processors, which act, effectively, like a single processor with several functionalities. Furthermore, in the present application, the terms "system" and "processor" are used interchangeably.) Alternatively, the selected phase (e.g., the R wave of the ECG signal) is identified by the ECG monitor. Further alternatively, the selected phase (e.g., the R wave of the ECG signal) is identified by the CRM device.

For some applications, image tracking is applied to the native image stream, with respect to a guiding catheter or with respect to a segment of the guiding catheter, as described in further detail hereinbelow. For example, the native image stream may be image tracked with respect to the distal tip of the guiding catheter, e.g., a curved portion of the guiding catheter. Alternatively or additional, image tracking is performed with respect to one or more radiopaque (or otherwise visible) markers or segments of a tool. For some applications, image tracking, or alternative techniques for stabilizing the image stream, is performed with respect to a virtual feature or region of image frames of the native image stream. Such virtual features are typically derived from a manipulation (such as an average, a weighted average, a translation, a rotation, and/or a scaling) of the location of one or more observable features of the image. For example, the virtual feature may be the average location of two radiopaque markers of a balloon.

In Phase 2 of the automatic road map generation, a baseline fluoroscopic image frame is identified, typically automatically, the baseline image frame having been acquired prior to the contrast agent having been administered to the subject. (For some applications, the baseline frame is selected manually by the user.) For some applications, the baseline image frame is gated to a given phase of the subject's cardiac cycle (i.e., it selected based on its having been acquired at the given phase of the subject's cardiac cycle). Typically, the baseline image is an image frame that is generated immediately before the contrast agent was (or is about to be) administered to the subject (as described in further detail hereinbelow).

For some applications, the baseline image frame is used a reference image frame, to which to compare subsequent image frames, in order to determine when an angiographic sequence has commenced, as described hereinbelow. Alternatively or additionally, techniques such as the techniques described hereinbelow are used for determining the commencement or the end of an angiographic sequence, not by comparing image frames to the baseline image frame, but by detecting rapid changes in parameters of image frames of the image stream. For example, in order to determine when an angiographic sequence has commenced, a vesselness descriptor may be calculated for each image in the image stream. The vesselness descriptor is typically calculated in accordance with the techniques described hereinbelow. For example, the vesselness descriptor may be calculated by counting a number of possible centerline points of a vessel in each of the images that are located near to possible edge lines of the vessel. Commencement of an angiographic sequence is determined by detecting a rapid increase in the vesselness descriptor. The end of an angiographic sequence is determined by detecting a rapid decrease in the vesselness descriptor.

For some applications, the baseline image frame is analyzed such that the degree of "vesselness" (i.e., the extent to which a given pixel is likely to be an element of an image of a vessel) in applicable areas of the image frame is determined. For example, vesselness may be determined by means of a filter, such as the filter described in the article by Frangi (a "Frangi filter"), cited hereinabove, which is incorporated herein by reference, and/or by means of a filter that performs enhancement and/or detection and/or segmentation of curvilinear structures. For some applications, a filter is used that is similar to a Frangi filter, but that differs from a Frangi filter ("a Frangi-like filter") (a) in that vesselness is a homogeneous function, and/or (b) in the multipliers employed for the normalization of scales.

Figure 2:
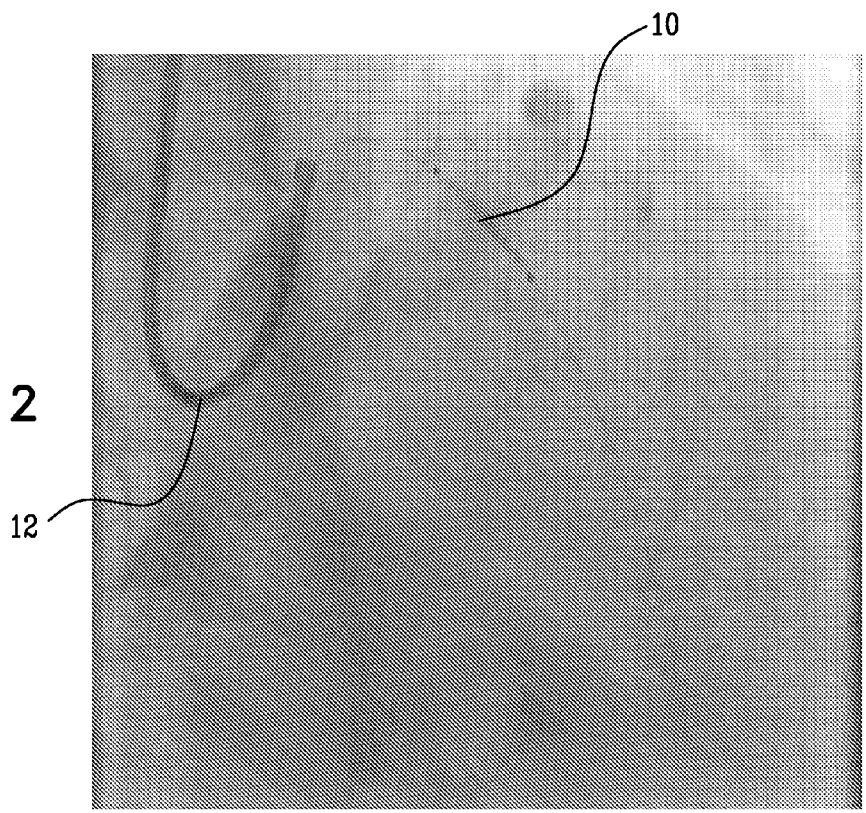
FIG. 2 shows a baseline image that was used in the automatic generation of a road map, in accordance with some applications of the present invention.

Reference is now made to FIG. 2, which shows a baseline image that was used in the automatic generation of a road map, in accordance with some applications of the present invention. A guiding catheter 12, through which a catheter of a non-inflated balloon 10 is inserted, may be observed.

In Phase 3 of the automatic road map generation, an identification or detection is typically provided that angiography has commenced or is about to commence. For example, commencement of the angiography may be detected by detecting the injection of contrast agent, and/or by detecting the activation of a special imaging mode such as cine. For some applications, several angiographic sequences are acquired and the commencement of each of the angiographic sequences is detected, in order to separate the angiographic sequences from one another. Typically, the angiographic sequences are separated from each other such that the most suitable image frame for generating a new road map is selected only from among the frames belonging to the most recent angiographic sequence.

For some applications, the identification that angiography has commenced, or is about to commence, is provided automatically by the apparatus for injecting the contrast agent. Alternatively or additionally, the identification that angiography has commenced, or is about to commence, is provided manually by the operator of the apparatus injecting the contrast agent. Further alternatively or additionally, the identification that angiography has commenced is provided automatically by identifying that in the acquired image frames there is an increased portion or count of vessel-like pixels. For example, such automatic identification may be provided by means of a filter that performs enhancement and/or detection and/or segmentation of curvilinear structures, a Frangi filter, and/or a Frangi-like filter. For some applications, the commencement of an angiographic sequence is detected by detecting the appearance of temporarily-appearing vessel-like features. Typically, the detection of temporarily-appearing vessel-like features indicates a new angiographic sequence.

For some applications, the identification that angiography has commenced is provided automatically by means of image processing, as described in WO 08/107,905 to Iddan, which is incorporated herein by reference. Suitable image processing techniques include the analysis of changes in the current image, and/or, specifically, changes in the image region at the distal end of the catheter from which the contrast agent enters the subject's vasculature (such as a guiding catheter in the case of coronary road mapping). For example, changes in the image may include a relatively abrupt change in the color and/or grayscale level (i.e., darkness) of a relatively large number and/or portion of image pixels, or the appearance of vessel-like features in the image, or any combination thereof. It is noted that by assessing a change in the darkness level to identify the time of injection of the contrast agent, the automatic road map generation processor may identify a darker area of the image or a lighter area of the image, depending on whether the contrast agent is represented as dark or light.

For some applications, the identification that angiography has commenced is performed by comparing a current image frame to the baseline image frame. Alternatively, the identification that angiography has commenced is performed not by comparing image frames to the baseline image frame, but by detecting rapid changes in parameters of image frames of the image stream.

For some applications, the identification that angiography has commenced is accelerated by reducing the resolution of the image frames, and applying image processing techniques to the reduced-resolution image frames.

It is noted that whereas specifically assessing the region at the distal end of the catheter typically enhances signal to noise (because this region is most likely to show an abrupt change), the scope of the present invention includes assessing most or all of the acquired image data to identify the injection of the contrast agent.

Figure 3:
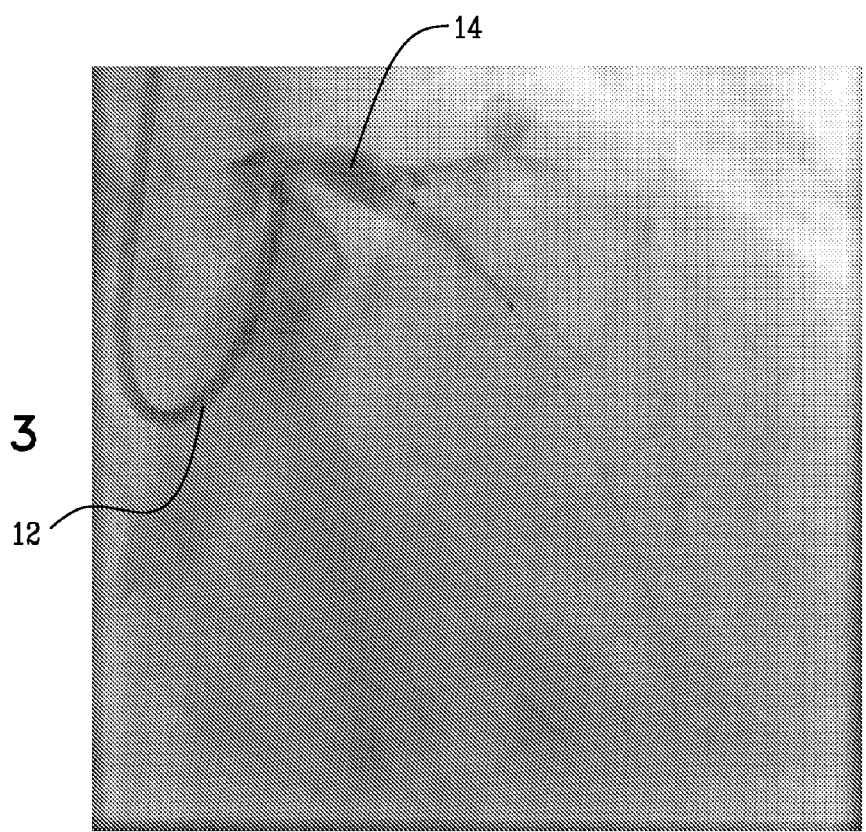
FIG. 3 shows an image frame during the commencement of an angiographic sequence that was used in the automatic generation of a road map, in accordance with some applications of the present invention.

Reference is now made to FIG. 3, which shows an image frame during the commencement of an angiographic sequence that was used in the automatic generation of a road map, in accordance with some applications of the present invention. A cloud 14 of contrast agent may be observed in the vicinity of the distal tip of guiding catheter 12.

In Phase 4 of the automatic road map generation, an identification or detection is typically provided that the acquisition of image frames in the presence of contrast agent has ended or subsided. That is to say, the contrast agent injected into the coronary arteries has dissipated (or mostly dissipated) such that it is generally no longer visible in the fluoroscopic images. For some applications, such identification is provided automatically by apparatus that injects the contrast agent, and/or is provided manually by the operator of the apparatus injecting the contrast agent. For some applications, such identification or detection is provided by identifying decreased vesselness, for example, by means of a filter that performs enhancement and/or detection and/or segmentation of curvilinear structures, a Frangi filter, and/or a Frangi-like filter. Alternatively or additionally, such identification or detection is provided automatically by image processing techniques similar to those described with reference to Phase 3 above.

For some applications, and as an alternative to Phase 4, the end of a sequence of angiographic images is assumed after a certain period of time has elapsed since the commencement of the angiographic sequence. The period of time typically corresponds to the typical duration of an angiographic sequence.

In Phase 5 of the automatic generation of the road map, the angiographic image frames (also known as angiograms) corresponding to a given angiographic sequence are automatically analyzed, such that an angiogram is derived (e.g., selected) from the set of angiograms, based upon visibility of at least a portion of the blood vessels in the angiograms. For some applications, the angiogram with the greatest visibility of coronary arteries is selected, with such selection typically being automatic. The greatest visibility is typically determined based upon the greatest total number of arteries observed, the greatest number of image pixels attributed to an artery, and/or the greatest image contrast in the appearance of specific arteries. Such an angiogram with the greatest visibility of coronary arteries is typically the most suitable for serving as the basis for the most informative road map in situations wherein the greatest amount of vasculature should be observed.

For some applications, an aggregated image of two or more angiograms is derived from the sequence of angiograms. For example, two or more angiograms that provide the greatest visibility of the coronary arteries are added to each other. Alternatively, a portion of a first angiogram that provides good visibility of a first portion of the coronary arteries is aggregated with a portion of a second angiogram that provides good visibility of a second portion of the coronary arteries.

For some applications, an angiogram having the greatest visibility of the coronary arteries is identified by means of vesselness of image pixels. Alternatively or additionally, such vesselness is determined by means of a filter, such as a filter that performs enhancement and/or detection and/or segmentation of curvilinear structures, a Frangi filter, and/or a Frangi-like filter. For some applications, the determination of vesselness of image pixels is made with reference to known anatomical structures, and/or with reference to known anatomy of the specific subject. For some applications, the determination of vesselness of image pixels is made while accounting for the specific viewing angle at which the images are generated.

For some applications, only angiograms belonging to the angiographic sequence that are gated to a given phase of the cardiac cycle are analyzed. An angiographic image frame is derived (e.g., selected) from the gated angiograms, based upon visibility of at least a portion of the blood vessels in the angiograms. For example, the gated angiogram with the greatest visibility of coronary arteries may be selected. For some applications, the given cardiac phase is an end-diastolic phase, at which certain coronary vessels are typically the most spread apart.

For some applications, the end-diastolic phase is identified by means of image processing (and not, or not exclusively, by means of gating to the ECG signal). For example, an image in which distances between coronary vessels are largest may be identified, and/or a degree of vesselness within a region of interest may be analyzed. For some applications, an image frame in which motion of coronary blood vessels is at a minimum, as would typically be expected during end-diastole, is identified.

For some applications, limiting the derivation of the angiogram to only among angiograms gated to a specific cardiac phase is suitable when the operator's interest is focused on the specific phase. Typically, for such applications, the operator will designate the phase with respect to which the angiograms are gated via an input device. For some applications, only angiograms sampled at a defined time interval (e.g., every 100 ms, or between the 700th ms and 1000th ms of every second), and/or at a defined sequential interval (e.g., every fifth frame, or between the 10th and 15th of every 15 frames), are analyzed. For some applications, frames sampled within the time interval are gated, and/or frame(s) with the highest vesselness are identified from among frames sampled within the time interval.

Figure 4:
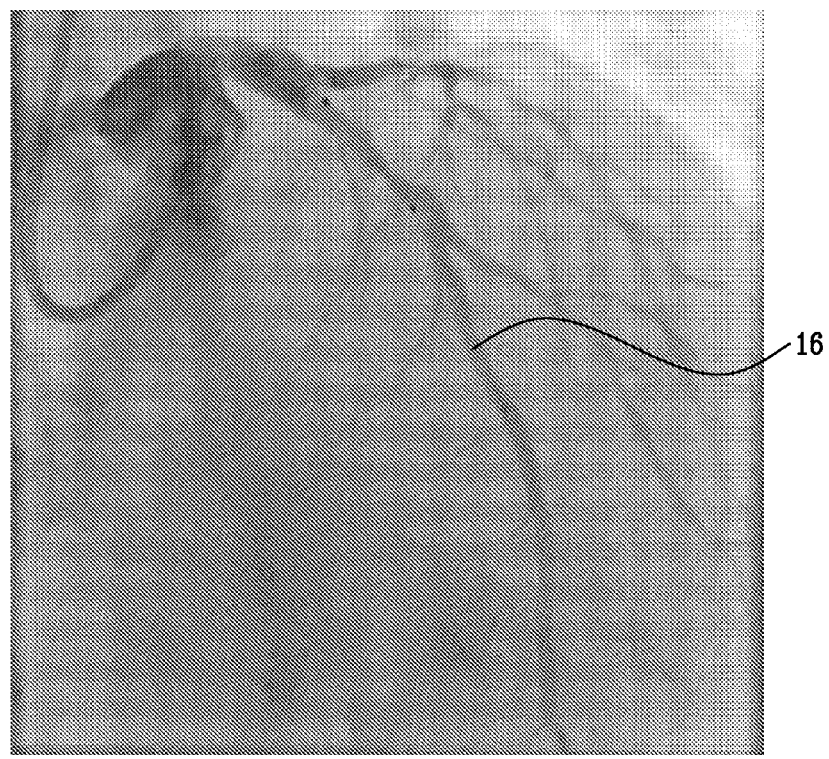
FIG. 4 shows an angiographic image (i.e., an angiogram) that was derived from a set of angiograms, some blood vessels appearing highlighted in the image, in accordance with some applications of the present invention.

Reference is now made to FIG. 4, which shows an angiographic image (i.e., an angiogram) that was derived from a set of angiograms, some blood vessels 16 appearing highlighted (i.e., demonstrated) in the image, in accordance with some applications of the present invention.

In Phase 6 of the automatic road map generation, designated vessels in the selected angiogram(s) are enhanced, typically automatically. For some applications, low-contrast vessels that are typically less observable in the non-enhanced image, and/or narrow vessels that are typically less observable in the non-enhanced image, are detected and enhanced. For some applications, non-vascular structures whose spatial and/or temporal characteristics differ from those of vascular structures are identified, and the visibility of such structures is reduced. For example, such spatial characteristics may include dimensions, relative location, gray level, texture, edge smoothness, or any combination thereof, and such temporal characteristics may include relative motion, absolute motion, and/or a change over time of any of any of the aforementioned spatial characteristics. For some applications, the enhancement is performed by means of a filter that detects and/or segments curvilinear structures. Alternatively or additionally, the enhancement is performed by means of a Frangi-filter, such that vessels and their local orientation are automatically detected by analyzing eigenvalues and eigenvectors of the Hessian matrix of a smoothed image.

In Phase 7 of the automatic road map generation, the darkest lines, or the center lines, or any other characterizing or representative lines corresponding to paths of one or more designated blood vessels are determined, typically automatically. For some applications, the points comprising such lines are determined by means of their relatively high value of vesselness. Alternatively or additionally, the points comprising such lines are determined by the extent to which their gradient is orthogonal to the eigenvector of the Hessian matrix corresponding to the highest eigenvalue. For some applications, such determination is assisted by a voting function applied to points that are adjacent to those points that are eventually determined to constitute the center line itself.

For some applications, thresholding is applied to image pixels by means of hysteresis. For example, pixels the vesselness value of which falls below the high threshold of the hysteresis, but yet above the low threshold of the hysteresis, are incorporated into a line if they are contiguous with pixels that fall at or above the high threshold of the hysteresis.

For some applications, the points which form the aforementioned lines are determined by means of morphological operations. For example, such morphological operations may include the skeletonization of a thresholded vesselness image. For some applications, the threshold applied is adaptive according to the specific region in the image.

Figure 5:
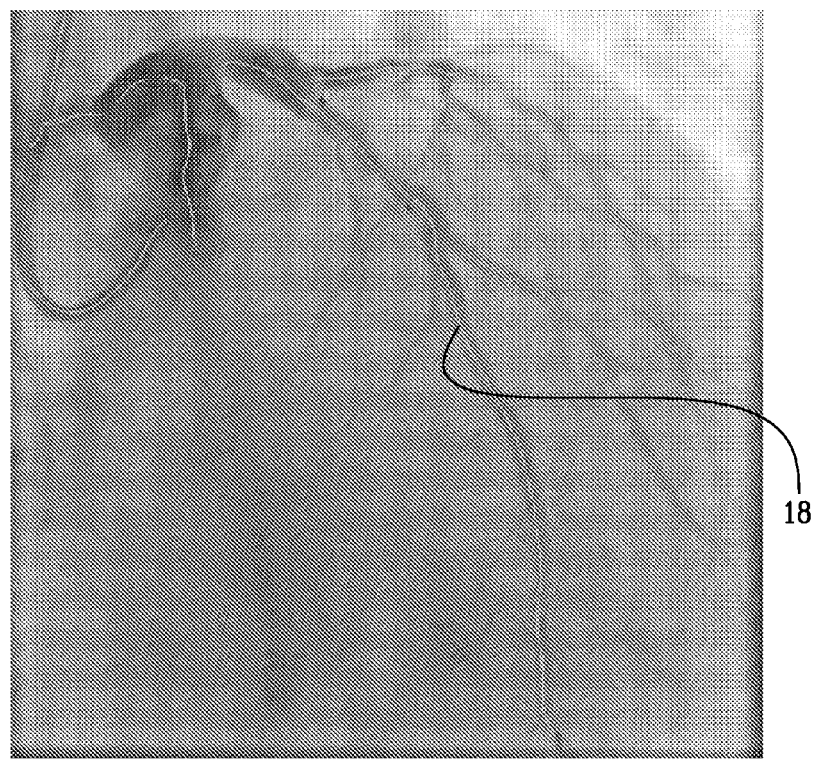
FIG. 5 shows center lines constructed automatically along a portion of the blood vessels, in accordance with some applications of the present invention.

Reference is now made to FIG. 5, which shows center lines 18 constructed automatically along a portion of the blood vessels, in accordance with some applications of the present invention. The center lines are shown overlaid upon the angiogram from which they were constructed.

Figure 6:
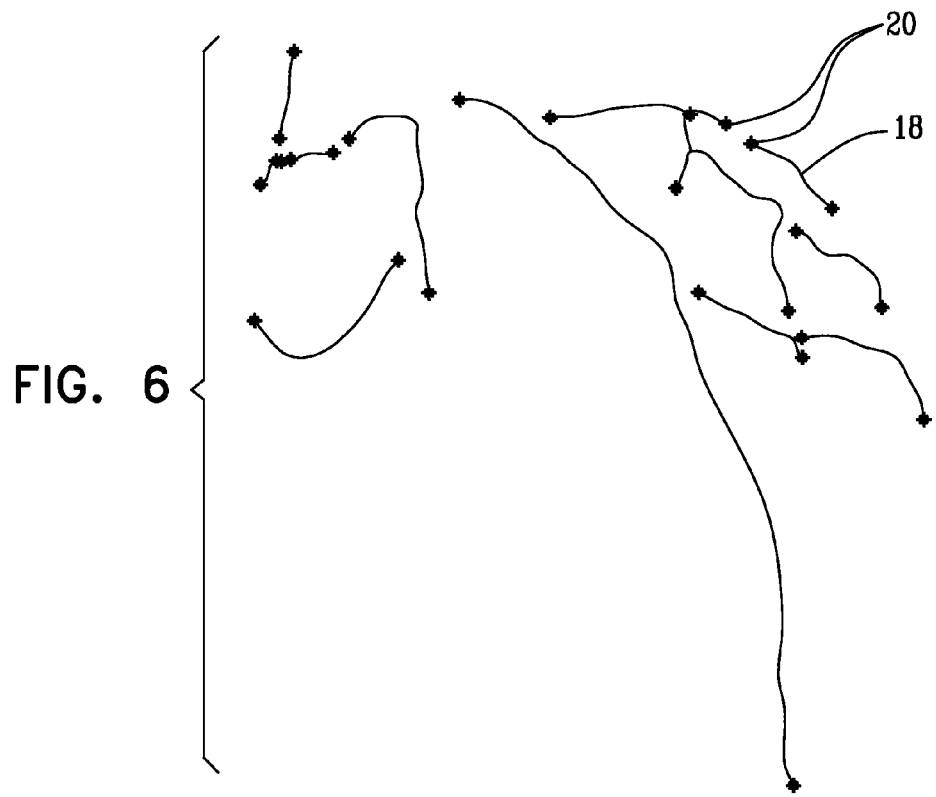
FIG. 6 shows end points at discontinuities in the center lines that were identified automatically, in accordance with some applications of the present invention.

Reference is now made to FIG. 6, which shows end points 20 (shown as stars) at discontinuities in center lines 18 that were identified automatically, in accordance with some applications of the present invention. In Phase 8 of the automatic road map generation, which is applicable in cases in which there are discontinuities within a center line (or any other characterizing or representative line) of a designated vessel, such discontinuities are bridged, typically automatically. For some applications, end points are identified automatically at both sides of a discontinuity. For some applications, bridging is performed across gaps between end points by means of a shortest-path algorithm, for example the shortest-path algorithm described in the article by Dijkstra, which is cited hereinabove, and which is incorporated herein by reference. For some applications, bridging is performed subsequent to the detection of edges (i.e., boundaries), corresponding to each already-determined segment of the center lines, i.e., subsequent to Phase 9 of the automatic road map generation, described hereinbelow.

For some applications, bridging is performed across gaps between end points by means of an algorithm that takes into account the directional vectors of the lines at both sides of the discontinuity. Alternatively or additionally, the bridging is performed with reference to known typical structures of the coronary tree. For example, bridging may be performed based upon what is typical at the corresponding section of a coronary tree.

For some applications, the bridging of gaps is performed with reference to known structures of the coronary tree of the particular subject who is being imaged. Typically, in such cases, gaps are bridged based upon what has been previously observed, by means of imaging a corresponding section of the subject's coronary tree. In accordance with respective applications, the imaging modality used to image the corresponding section of the subject's coronary tree is the same as the modality that is used to generate the angiograms, or is a different imaging modality (for example, pre-operative CT) from the imaging modality used to generate the angiograms (for example, fluoroscopy).

For some applications, the bridging of gaps is made while accounting for the specific viewing angle at which the images are generated.

Figure 7:
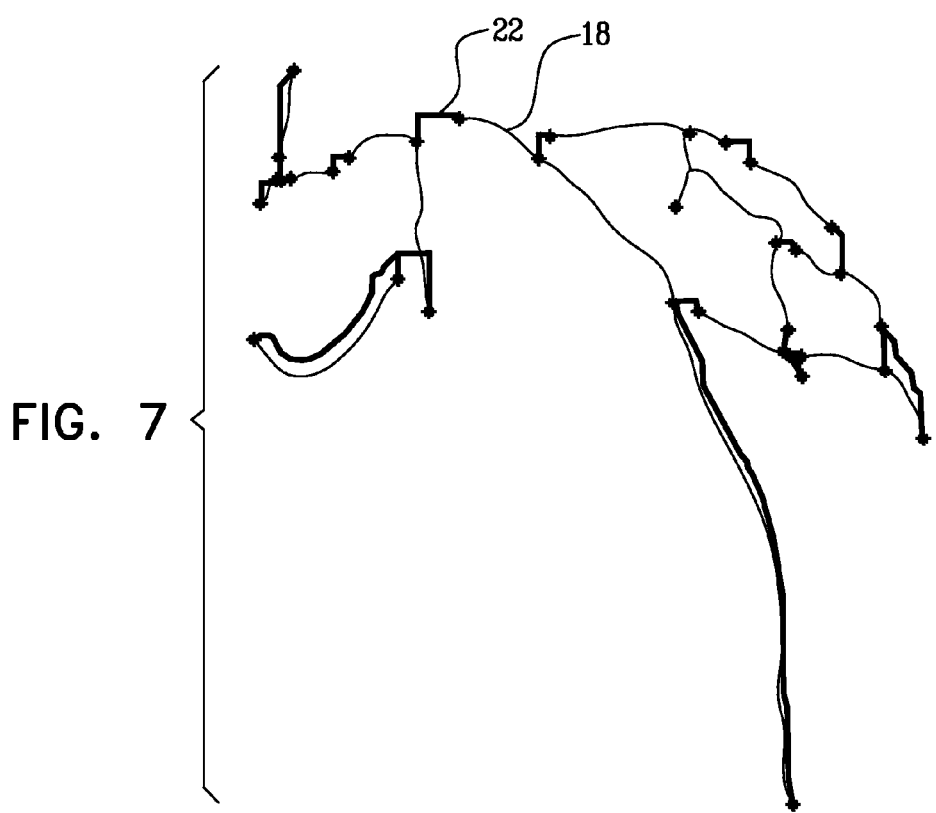
FIG. 7 shows gaps between end points in the center lines having been bridged automatically, in accordance with some applications of the present invention.

Reference is now made to FIG. 7, which shows bridges 22 in gaps between end points in center lines 18, the bridges having been generated automatically, in accordance with some applications of the present invention.

In Phase 9 of the automatic road map generation, the boundaries (i.e., edges or edge lines) of one or more designated vessels are determined, typically automatically. For some applications, such boundaries are determined by means of region-based adaptive thresholding of the vesselness image. Alternatively or additionally, such boundaries are determined by means of a region-growing algorithm. Further alternatively or additionally, such boundaries are determined by means of an edge detector, and/or by means of a morphological operation. For some applications, such boundaries are determined by means of a watershed technique, which splits an image into areas, based on the topology of the image. Alternatively or additionally, such boundaries are determined by means of a live contour, and/or by means of matching filters.

For some applications, the determination of boundaries is made with reference to known typical structures of the coronary tree. Typically, in such cases, boundaries are determined in certain vessel segments based upon what is typical at the corresponding section of a coronary tree.

For some applications, the determination of boundaries is made with reference to structures of the coronary tree of the specific subject. Typically, boundaries are generated based upon what has been previously observed, by means of imaging a corresponding section of the subject's coronary tree. In accordance with respective applications, the imaging modality used to image the corresponding section of the subject's coronary tree is the same as the modality that is used to generate the angiograms, or is a different imaging modality (for example, pre-operative CT) from the modality used to generate the angiograms (for example, fluoroscopy).

For some applications, the boundaries are determined by means of a dynamic programming approach, optimizing a penalty function. For example, the penalty function may be based upon image derivatives along directions perpendicular to the center line, and/or the distance from the center line.

For some applications, center lines are determined for the vessels identified in most of, or the entire, image frame, while boundaries are only determined for specific vessels or sections of vessels. For example, boundaries of specific vessels may be determined upon the user indicating, typically by means of an input device, a region of interest or a specific vessel of interest or a specific section of such vessel.

For some applications, the determination of boundaries is made while accounting for the specific viewing angle at which the images are generated.

Figure 8:
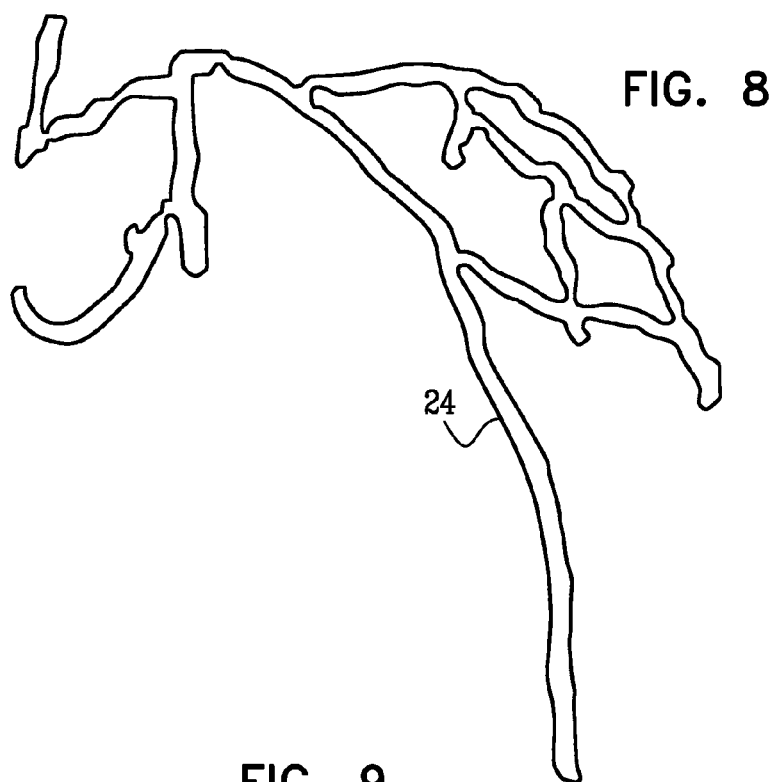
FIG. 8 shows edge lines (i.e., boundaries) of the blood vessels, which were detected automatically, in accordance with some applications of the present invention.

Reference is now made to FIG. 8, which shows edge lines 24 (i.e., boundaries) of blood vessels, which were detected automatically, in accordance with some applications of the present invention.

For some applications, the system automatically validates a point/segment as being part of the center line, and points/segments as being part of edge lines at sides of the center line, by cross-referencing the center line points/segments and edge line points/segments with respect to each other. For example, at each side of a potential center line, an edge the gradient of which is perpendicular, or almost perpendicular, to that of the center line is selected such that the two gradients are in opposite directions and leading away from the center line. Typically, such validation is used for the elimination of inappropriate center lines (or pixels attributed to such lines) and/or edge lines (or pixels attributed to such lines) and for the selection of those that are most appropriate.

For some applications, and typically subsequently to the aforementioned validation of matching between center lines and edge lines, missing points/sections in center lines are deduced and added. For some applications, vectors obtained from a Frangi-like filter are applied from known points at both sides of a gap in a center line and into the gap. Such vectors are local and typically are applied incrementally with each increment based upon a new local computation, until the gap is typically eliminated.

For some applications, and typically subsequently to the aforementioned validation of matching between center lines and edge lines, missing points/sections in edge lines are deduced and added. For some applications, sets of edge points are selected at both sides of a gap. A dynamic programming approach, optimizing a penalty function, is then applied to fill in the gap by proposing additional edge points, the distances from the center line of which edge points are typically similar to those of the adjacent, already-known edge points. The process is typically applied continuously until the gap in the edge line is bridged.

For some applications, the road map includes an image or contour of a tool that was situated within one of the blood vessels at the time of the angiogram. Alternatively or additionally, the road map includes markers, and/or a graphical representation of markers, of a tool that was situated, at the time of the angiogram, within one of the blood vessels. For example, the road map may include, in addition to the boundaries of the vessel, small circles indicating the positions of the markers of a coronary balloon while such balloon was situated within the vessel at the time the angiogram was taken.

Figure 9:
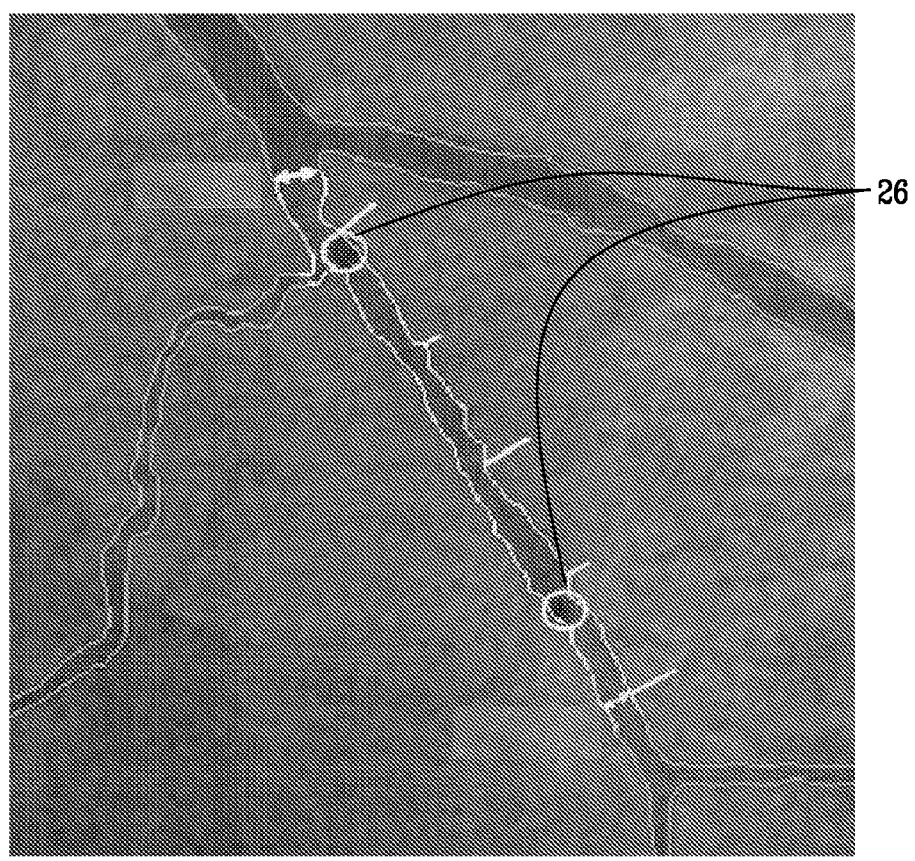
FIG. 9 shows a road map in which the markers of a balloon situated within an artery are visible, in accordance with some applications of the present invention.

Reference is now made to FIG. 9, which shows a road map in which markers 26 of a balloon situated within an artery are visible, in accordance with some applications of the present invention.

For some applications, generation of the road map is intra-procedural. For example, the road map may be automatically generated in real time, or in near real time relative to the end of the angiographic segment. Alternatively, the automatic generation of the road map is post-procedural.

It is noted that, for some applications, not all of the steps shown in FIG. 1 are performed for the automatic generation of the road map.

Generation of Distance Indicators

Figure 10:
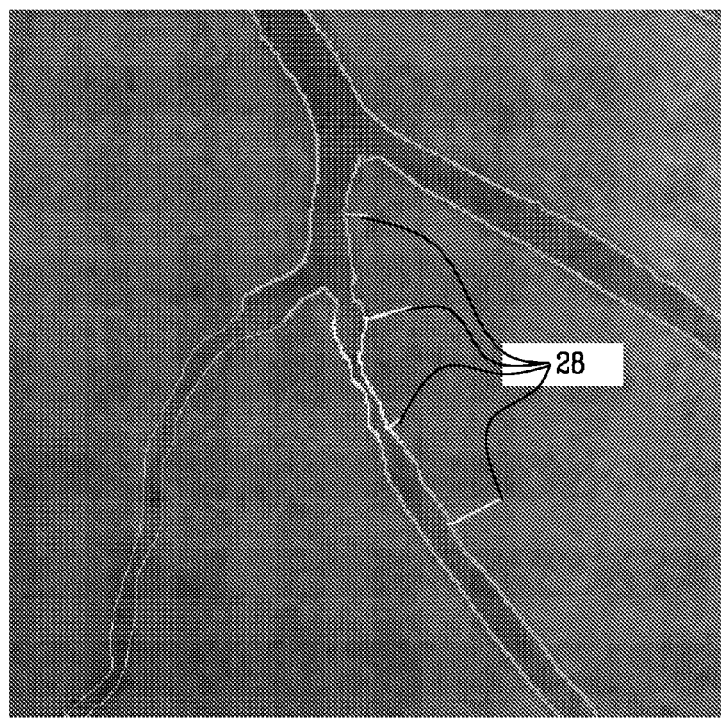
FIG. 10 shows distance indicators on a road map, in accordance with some applications of the present invention.

Reference is now made to FIG. 10, which shows distance indicators 28 on a road map, in accordance with some applications of the present invention. For some applications, a road map is generated that includes distance indicators (e.g., notches) placed along or across a designated vessel or a section thereof. For example, the indicators may be placed in order to show the length or the diameter of the vessel or section thereof. For some applications, the distance indicators are generated automatically.

For some applications, distance indicators are longitudinal, and are placed along a borderline, and/or along a center line (or any other characterizing or representative line) of a designated vessel. For some applications, segments of a designated vessel are marked in different colors corresponding to distances.

For some applications, the distances between the distance indicators are known. For example, the distances between the indicators may be determined based upon some known anatomical feature, or based upon a known dimension of another element that is, or has been, present in the image stream. For example, the known dimension may be the distance between radiopaque (or otherwise visible) markers or segments of a tool. For some applications, the tool is a balloon, a marker wire, a stent, an endoluminal measurement catheter (such as an FFR catheter), and/or an endoluminal imaging catheter (such as an MRI, OCT, IVUS, NIRS, and/or an ultrasound catheter).

For some applications, the known dimension is the length of an already-deployed stent, and/or the length of a radiopaque (or otherwise visible) segment of a tool (e.g., a guide wire). Alternatively or additionally, the known dimension is the diameter of a tool, such as a guiding catheter. For some applications, the diameter of the guiding catheter is indicated by the user. Alternatively or additionally, the diameter of the guiding catheter is a default value set in the system or otherwise determined by the system.

For some applications, the guiding catheter is indicated by the user, via an input device (e.g., by pointing to the catheter using the input device). Alternatively or additionally, the guiding catheter is identified automatically by the system, by means of image processing. For some applications, the user indicates the image region in which the guiding catheter is located, and then the guiding catheter is detected automatically. For example, the user may indicate (using an input device) a point anywhere in the region of the guiding catheter, and then the guiding catheter is detected automatically. Or, the user may indicate a point on the guiding catheter itself for its identification.

Figure 11:
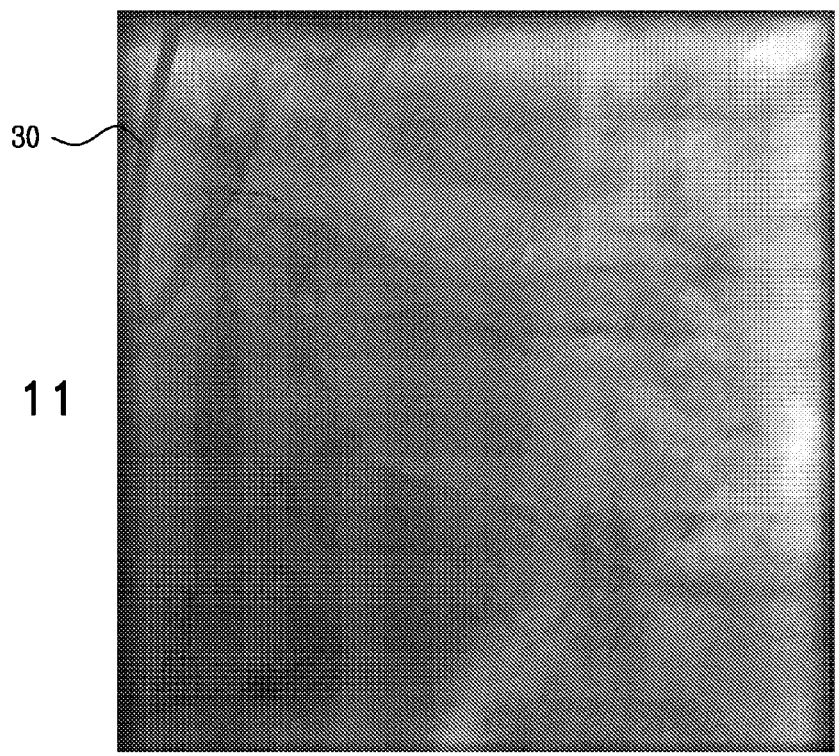
FIG. 11 shows an image in which a guiding catheter has been segmented, in accordance with some applications of the present invention.

Reference is now made to FIG. 11, which shows a fluoroscopic image in which a guiding catheter 30 has been segmented, in accordance with some applications of the present invention. For some applications, after the guiding catheter is detected, it is segmented automatically so that the portion of its lumen that is within the image frame is highlighted. (Although the image in FIG. 11 is black-and-white, typically the segmented catheter is highlighted in color.) For some applications, the guiding catheter is automatically detected and/or segmented using techniques similar to those described hereinabove for the automatic identification of vessels.

For some applications, distance indicators are placed, in the form of a grid, in the entire image frame, in a region of interest within the image frame, and/or in a segment of a vessel within the image frame.

For some applications, distance indicators are placed, in the form of concentric circles, in the entire image frame, in a region of interest within the image frame, and/or in a segment of a vessel within the image frame. For some applications, distance indicators are placed in the form of concentric circles, the center of which circles is at the current location of a cursor positioned by the user, or a location otherwise indicated by the user.

For some applications, the distance indicators are used for measurements, for example, quantitative vessel analysis (QVA) measurements, as described hereinbelow.

Displaying the Road Map and the Fluoroscopic Image Stream

For some applications, a road map (e.g., an automatically generated road map, as described hereinabove) is displayed in combination or conjunction with a stabilized image stream, for example, as described in WO 08/107,905 to Iddan, which is incorporated herein by reference. For example, the road map may be overlaid upon a stabilized or non-stabilized image stream, typically automatically. For some applications, the road map is overlaid on a current image stream in real time, or in near real time. Alternatively or additionally, the road map is overlaid on an image stream, in reloop mode (i.e., a mode in which an image stream, which is typically a recent sequence, is replayed in a loop). For example, the road map may be overlaid on a fluoroscopic image stream from which the road map was derived, while the fluoroscopic image stream is being replayed in a loop.

Figure 12:
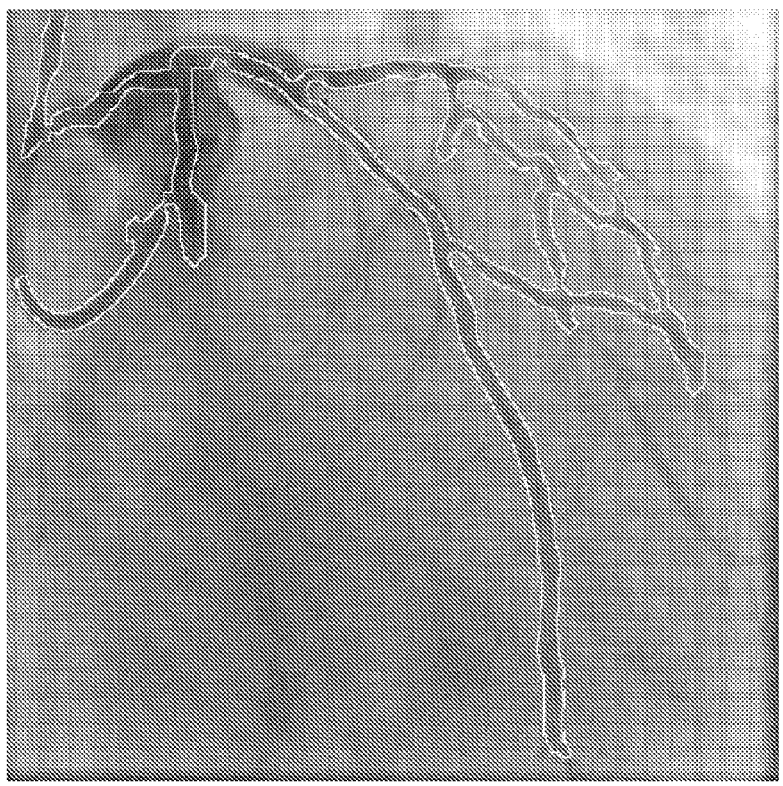
FIG. 12 shows an automatically-generated road map, overlaid upon the angiogram from which it was generated, in accordance with some applications of the present invention.

Reference is now made to FIG. 12, which shows an automatically-generated road map, overlaid upon the angiogram from which it was generated, in accordance with some applications of the present invention. For some applications, overlaying of the road map on the angiogram from which it was created is used to evaluate the accuracy and/or completeness of the road map. As shown, the road map is typically marked as a set of thin boundary lines (although the road map may be marked in a different manner).

Figure 13:
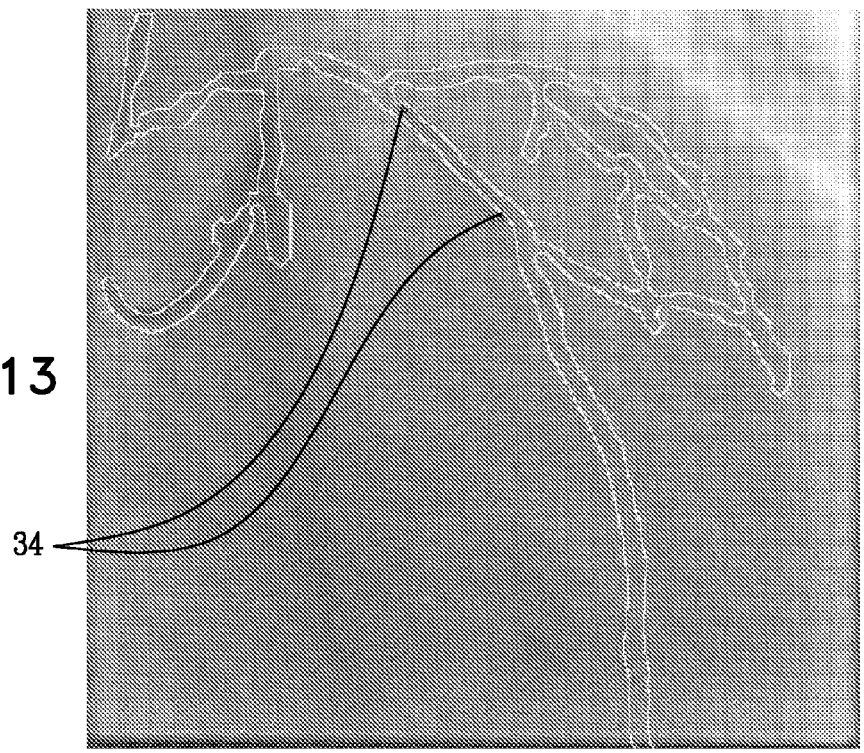
FIG. 13 shows an automatically-generated road map, overlaid upon an image frame belonging to a stabilized image stream, in accordance with some applications of the present invention.

Reference is now made to FIG. 13, which shows an automatically-generated road map, overlaid upon an image frame belonging to a stabilized image stream, in accordance with some applications of the present invention. As shown in FIG. 13, for some applications, the road map is overlaid upon a fluoroscopic image frame that is not an angiogram (that is, the road map is overlaid on an image frame that was generated in the absence of a contrast agent). As shown, the road map is marked as a lighter-colored boundary line (although the road map may be marked in a different manner). Thus, the layout of the vasculature is depicted even though the vasculature itself is invisible in the underlying fluoroscopic image. An inflated coronary balloon can be identified in the fluoroscopic image by its two dark markers 34. Thus, the location of the balloon within the road map is determined.

For some applications, using the techniques described herein facilitates further identification of the location of the balloon vis-à-vis the vessel in which it is placed, without requiring additional angiograms. Additional angiograms may necessitate irradiation of subject and/or staff, and/or the additional injection of a potentially-damaging contrast agent. Thus, by displaying the road map on top of the fluoroscopic image, irradiation of those involved in the procedure and the total dosage of contrast agent administered to the subject may be reduced. Alternatively or additionally, there are other advantages to displaying the road map on top of the fluoroscopic image.

Figure 14:
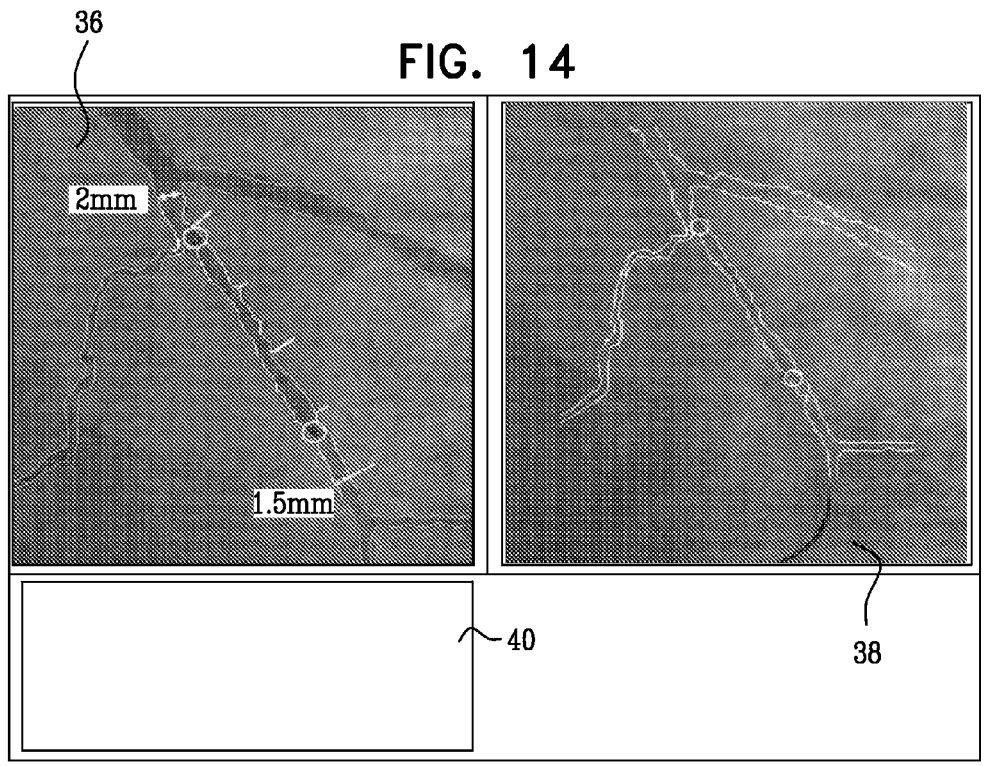
FIG. 14 shows a road map displayed side-by-side with a stabilized fluoroscopic image stream, edge lines of the road-map also being overlaid upon the fluoroscopic image stream, in accordance with some applications of the present invention.

Reference is now made to FIG. 14, which shows a road map 36 displayed side-by-side with a stabilized fluoroscopic image stream 38, edge lines of the road-map also being overlaid upon the fluoroscopic image stream, in accordance with some applications of the present invention. For some applications, the road map is displayed side-by-side with the fluoroscopic image stream. In accordance with respective applications, the fluoroscopic image stream that is displayed next to the road map is the native stream, a gated stream, an image tracked stream, and/or an image stream that is both gated and image tracked. For some applications, a quantitative-vessel-analysis box 40 is displayed on the screen. Quantitative vessel analysis measurements and/or diagrams are displayed in box 40 as described hereinbelow.

For some applications, image tracking of the fluoroscopic image stream is performed with respect to the guiding catheter or with respect to a segment thereof, as described hereinbelow. Alternatively or additionally, image tracking is performed with respect to radiopaque markers or segments of a tool (e.g., a balloon, a stent, a valve, or a different tool), as described hereinbelow.

For some applications, the road map is generally displayed side-by-side with the fluoroscopic image stream, and from time to time is momentarily overlaid upon the fluoroscopic image stream. In accordance with respective applications, the fluoroscopic image stream is native, gated, image tracked, and/or stabilized. For some applications, such overlaying is preceded by registration of the road map to fluoroscopic images. Typically, the road map is registered automatically, on-line, to the fluoroscopic images. Further typically, fiducials are identified within the road map and within the fluoroscopic image stream, in order to facilitate the registration of the road map to the fluoroscopic image stream. Fiducials are typically chosen that are observable even in images of the fluoroscopic image stream that are generated in the absence of a contrast agent. For example, the registration may be performed by means of a portion(s) (e.g., a marker, or a radiopaque portion) of a tool that is observable both in the road map and in the fluoroscopic images. For some applications, a road map corresponding to a given phase of the subject's cardiac cycle is generated, and is overlaid on a fluoroscopic image stream that is gated with respect to the same phase.

Figure 15:
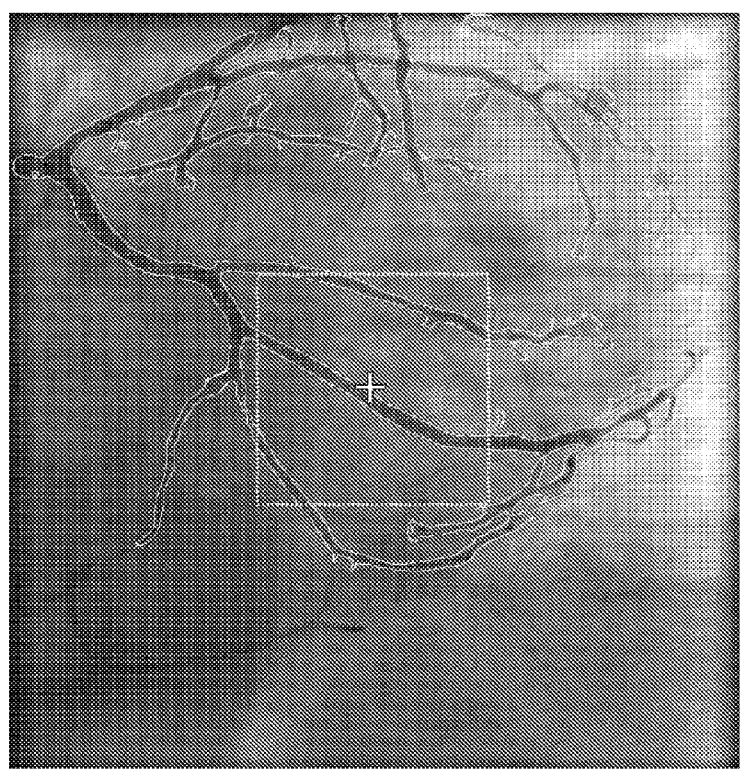
FIG. 15 shows a region of interest marked on a road map, in accordance with some applications of the present invention.

Reference is now made to FIG. 15 which shows a road map on which a region of interest (ROI) has been marked. For some applications, the road map that is displayed corresponds to a specific region of interest (ROI) within the angiogram(s) from which it was generated. For some applications, the ROI is automatically set to be the central region of the angiogram. Alternatively or additionally, the ROI is indicated by the user, such as by marking, using an input device, the center of the ROI, or a window encompassing the ROI. Further alternatively or additionally, the ROI is at first set automatically by the system and then modified by the user. For some applications, the size of the ROI that is displayed is pre-defined. For some applications, the zoom factor at which an image in the ROI is displayed may be changed by the user. In accordance with respective applications, the zoom factor at which a road map in the ROI is displayed is pre-defined, or may be changed by the user.

For some applications, the road map is toggled between the full view (i.e., on the entire angiogram(s) from which it was generated) and the zoom-in view (i.e., only the ROI). Alternatively or additionally, the road map switches automatically from the full view to the zoom-in view once a tool, such as a balloon, is identified by the system to have entered the ROI in a corresponding fluoroscopic image. For some applications, the balloon is identified as having entered the ROI based upon the presence of a radiopaque (or otherwise visible) marker(s) or segment, or some other identifiable portion, of the tool within the ROI. Similarly, for some applications, the road map switches automatically from the zoom-in view back to the full view once the aforementioned tool is identified by the system to have exited the ROI in a corresponding fluoroscopic image. For some applications, such switching, in either direction, is performed by the user. For some applications, the techniques described in the present paragraph are applied to the display of the fluoroscopic image stream.

For some applications, leafing (i.e., browsing) back and forth among multiple angiograms is enabled. Typically, leafing is performed among different images belonging to the same angiographic sequence. For example, the user may wish to observe the gradual spread of contrast agent along multiple angiograms belonging to the same angiographic sequence.

For some applications, leafing is performed among selected angiograms belonging to different angiographic sequences. For example, when determining the placement of a stent by means of an angiogram prior to its deployment, the user may wish to observe an angiogram belonging to a prior sequence in which balloon pre-dilatation was performed at the same lesion in order to ensure that the stent is placed at substantially the same location as the location at which pre-dilatation had been performed.

For some applications, the road map being displayed in conjunction with the fluoroscopic image stream comprises an image of the contrast agent itself, for example, as described in WO 08/107,905 to Iddan, which is incorporated herein by reference. For some applications, the road map comprises a synthesized background(s), enhancement(s), contour(s), pattern(s), texture(s), shade(s) and/or color(s) that was created based upon the visual information acquired from the injection and/or dissipation of contrast agent, using computer graphics and/or image processing techniques. Alternatively or additionally, the gray level of the road map is inversed, such that the road map appears light against a darkened background.

For some applications, the summation or combination of two road maps generated at different times in the procedure is displayed, for example, as described in WO 08/107,905 to Iddan, which is incorporated herein by reference. Typically, a road map generated during a given phase of a first cardiac cycle is summed with a road map generated during a same phase of a second (typically immediately subsequent) cardiac cycle, to create a combined road map that displays more coronary vessels and/or displays coronary vessels with greater clarity. For some applications, such as in the case of a total or partial occlusion in a coronary vessel, the combined road map may comprise the summation or combination of a road map created from an injection of a contrast agent proximally to the occlusion, and a second road map created from an injection of a contrast agent distally to the occlusion, such as via a collateral vessel and/or in a retrograde direction. For some applications, such road maps, which are based on the proximally- and distally-injected contrast agent, are created in the same phase of one or more cardiac cycles, which are not necessarily adjacent cardiac cycles.

For some applications, a three-dimensional road map is constructed by combining two or more two-dimensional road maps recorded from viewing angles that are typically different by 30 degrees or more, for example, as described in WO 08/107,905 to Iddan, which is incorporated herein by reference. For some applications, the two two-dimensional road maps (from which a three-dimensional road map is constructed) are recorded concurrently from two different viewing angles, such as by means of a bi-plane fluoroscopy system. Alternatively or additionally, a three-dimensional road map is created from CT angiography images, typically pre-procedural ones, and then correlated with the real time two-dimensional road map created from intra-procedural angiography. Further alternatively or additionally, a three-dimensional road map is constructed from two or more different images taken from the same viewing angle but during different phases in the cardiac cycle.

For some applications, the images displayed in conjunction with the road map and the stabilized image stream also comprise medical tools or probes. For example, images (or contours) of such tools may be overlaid or projected upon or within the road map. Alternatively or additionally, the markers or radiopaque segments of such tools (or graphical indications of such markers or segments) are overlaid or projected upon or within the road map. For some applications, the segment of the road map that is generally closer or closest to a designated tool is highlighted or indicated in some graphical manner.

For some applications, the road map is corrected, typically automatically, with respect to a designated vessel, based upon the layout of a tool situated in that vessel. For example, the road map may be corrected, typically automatically, with respect to a designated vessel, based upon the detected location of markers or radiopaque segments of a tool situated in that vessel. For some applications, if the tools (or markers or radiopaque segments thereof) are detected to be outside of the road map, then the road map is redrawn or reshaped so that such tools (or markers or radiopaque segments thereof) consequently appear to be within the road map.

For some applications, the medical tools or probes displayed in conjunction with the road map are activated or deployed in synchronization with a specific phase of a physiological signal or process, for example, as described in WO 08/107,905 to Iddan, which is incorporated herein by reference. For some applications, the road map is displayed in conjunction with an image stream that is stabilized with respect to that same phase.

For some applications, and in the case of images pertaining to a cyclically-moving organ, different road maps are displayed, typically in a cyclical manner, in conjunction with the then-current phase of the organ's motion cycle. For example, a dynamic road map as described may be correlated to the cardiac cycle, and/or the respiratory cycle.

Performing Measurements

For some applications, measurements are performed, typically automatically, based upon the determined boundaries of given vessels. For example, measurements may be performed based upon boundaries generated by means of the boundary generation techniques described hereinabove for most or all vessels within an image. Or, measurements may be performed on a specific vessel or segment of a vessel, the boundaries of which have been generated in accordance with the techniques described hereinabove.

Such measurements typically include lesion dimensions, reference artery dimensions, and quantitative vessel analysis (QVA), for estimating the extent of occlusion at a designated lesion. (QVA as used herein refers to the performance of the measurement techniques associated with a technique that is known as quantitative coronary angiography (QCA), but includes performing the measurement techniques (a) on any blood vessel of the subject, and not, specifically, a coronary artery, and (b) on any image of the blood vessel, and not, specifically, on an image of the blood vessel acquired using contrast agent. When performed with respect to coronary arteries, QVA is generally similar to QCA.)

For some applications, performing QVA using the techniques described herein facilitates the performance of measurements without requiring a manual process of constructing the center line and deriving the vessel edges. Typically, QVA is performed automatically or almost automatically, necessitating little to no user intervention or interaction, by using the aforementioned techniques described hereinabove for the automatic generation of center lines and edge lines.

For some applications, center lines and edge lines are validated by cross-referencing the lines, as described hereinabove. Subsequently, missing points/sections in edge lines are deduced and added, as described hereinabove, to support the aforementioned automatic or nearly automatic QVA. For example, sets of edge points may be selected at both sides of the gap, and a dynamic programming approach, optimizing a penalty function, is then applied to fill in the gap by proposing additional edge points whose distances from the center line are typically similar to those of the adjacent, already-known edge points. The process is typically applied continuously until the gap in the edge line is bridged.

Figure 18:
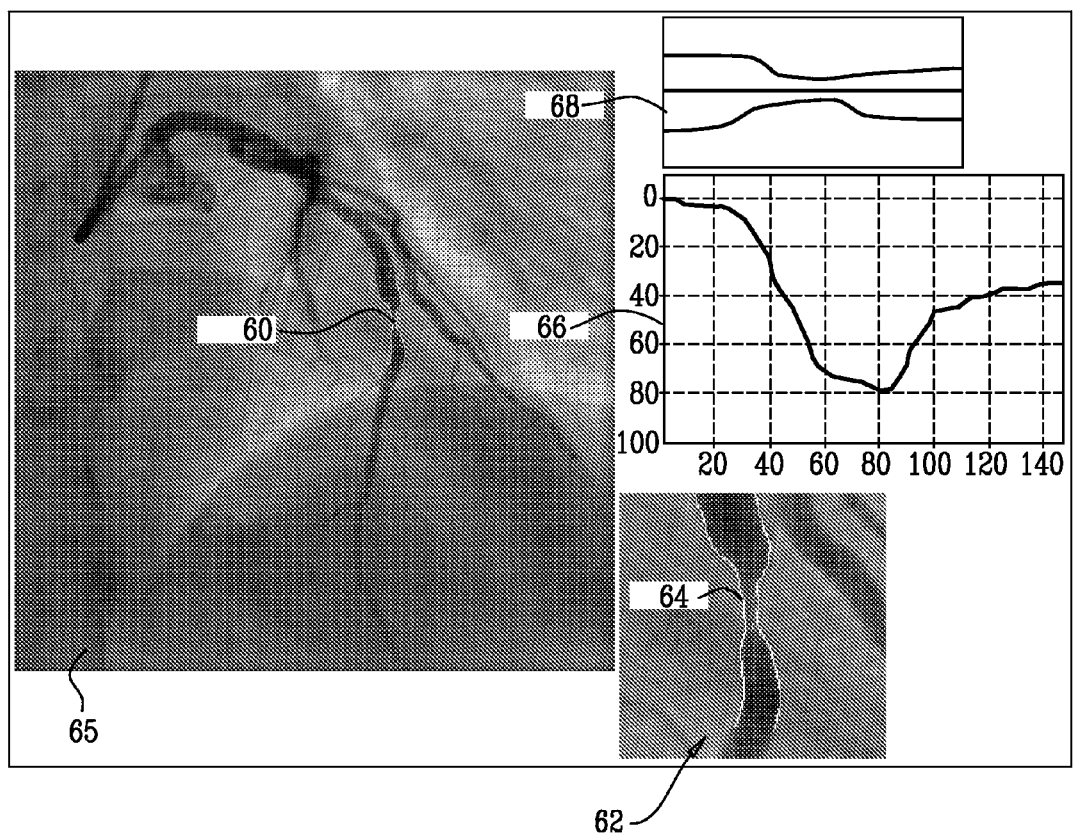
FIG. 18 shows QVA diameter diagrams, in accordance with some applications of the present invention.
Figure 19:
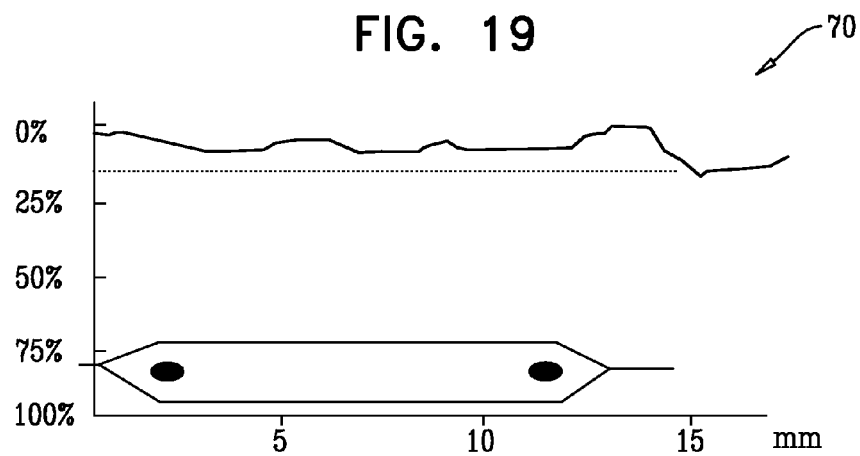
FIG. 19 shows a QVA diagram, comprising a representation of a tool at its relative location within the lesion on which QVA has been performed, in accordance with some applications of the present invention.

Reference is now made to FIGS. 16 and 19, which show, respectively, (a) a QVA box 48 which typically displays a QVA diagram with respect to a segment of a vessel that is part of a road map 44, and (b) a QVA diagram 70, in accordance with some applications of the present invention. As shown in FIG. 19, the horizontal axis of the QVA diagram represents the longitudinal dimension of an occlusion, with distance indicators, while the vertical axis represents the extent (such as percentage relative to the reference artery) of the occlusion. For some applications (typically, when a reference dimension, such as the diameter of the guiding catheter, has not yet been determined), the horizontal axis does not include distance indicators, but represents the longitudinal dimension of the occlusion. Typically, as shown in FIG. 16, and as shown on other figures which are described hereinbelow, the QVA diagram is displayed on the same screen as a road map, an angiogram, and/or a fluoroscopic image of the vessel that is occluded. (Although it is shown as a box in FIG. 16, box 48 typically appears like one of the QVA diagrams shown in FIGS. 18 and 19.)

For some applications, an ROI is indicated and then measurements referring to one or more vessels within the ROI are performed and displayed automatically. In accordance with respective applications, the ROI is determined automatically (for example, by designating the central area of the image frame as the ROI), or is determined by the user. For some applications, road map 44 is displayed alongside a fluoroscopic image stream 46, such as a live fluoroscopic image stream.

Figure 17A:
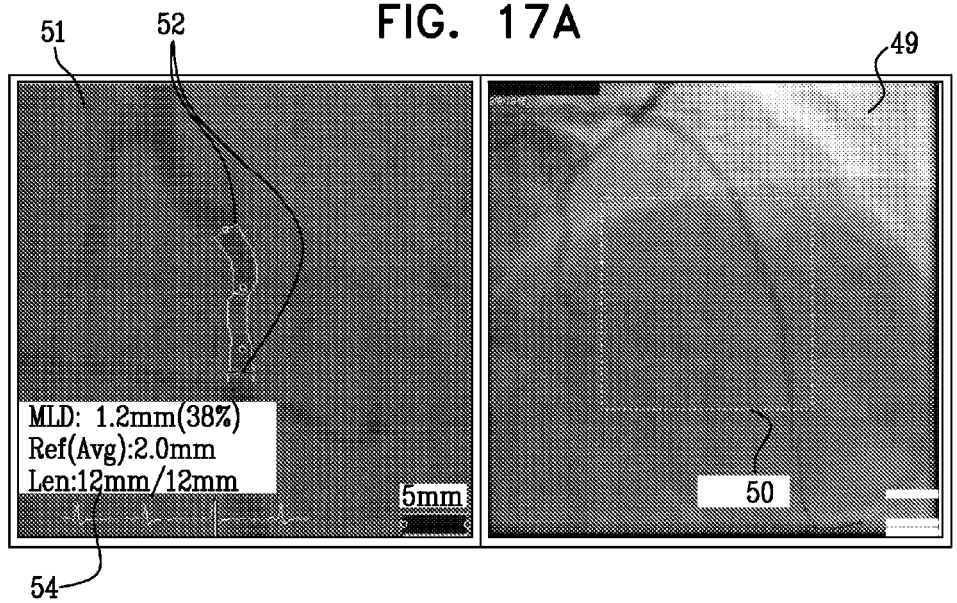
FIGS. 17A-B are schematic illustrations of a screen displaying QVA data with respect to a segment of a vessel that is part a selected angiographic image, in accordance with some applications of the present invention.

Reference is now made to FIG. 17A, which shows displayed on a screen (a) an angiogram 49, an ROI 50 having been identified in the angiogram, (b) an enlargement 51 of the ROI, in which a segment of a vessel (including edges and ends 52) is marked, and (c) QVA measurements 54 of the segment, in accordance with some applications of the present invention. For some applications, as an alternative, or in addition to, displaying a QVA diagram, QVA measurements are displayed, as shown in FIG. 17A.

Figure 17B:
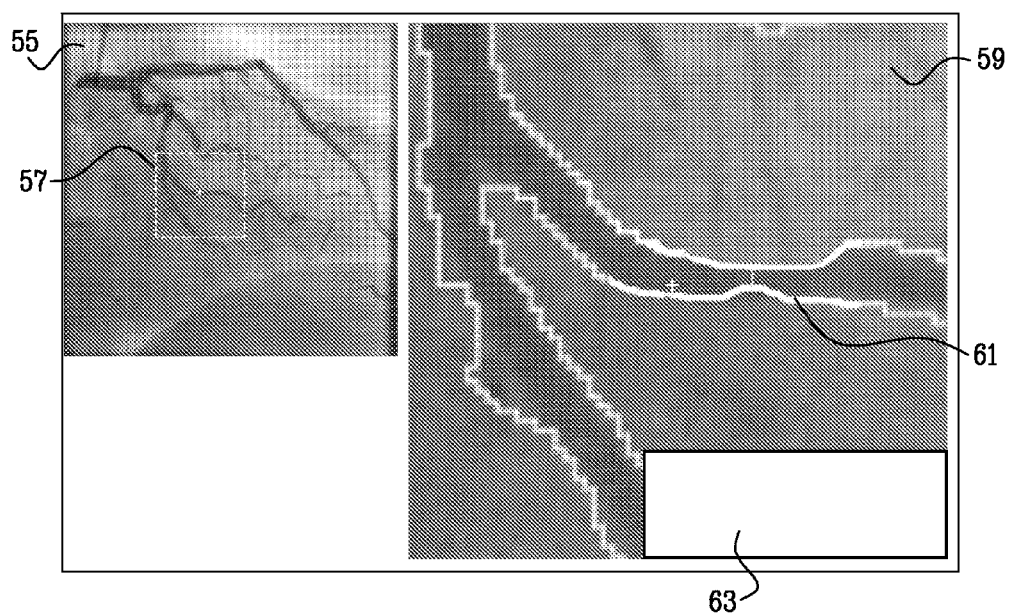

Reference is also made to FIG. 17B, which shows displayed on a screen (a) an angiogram 55, an ROI 57 having been identified in the angiogram, (b) an enlarged roadmap 59 of the ROI, in which a segment 61 of a vessel is marked, and (c) a QVA box 63 of the segment, in accordance with some applications of the present invention. (Although it is shown as a box in FIG. 17B, QVA box 63 typically appears like one of the QVA diagrams shown in FIGS. 18 and 19.)

For some applications, a user designates a single location in an image that is at or near a given location of a given blood vessel in the image. For example, using an input device, the user may click at or near the given location. For some applications, in response to the user designating the single location, the system automatically detects a lesion in the vicinity. For example, the system may identify edge lines and the reference diameters of the lesion. The reference diameters of a lesion are typically the diameters of the vessel at the longitudinal extremities of the lesion (the longitudinal extremities also being known as "healthy shoulders," or "reference arteries" to those skilled in the art). For some applications, the reference diameters are the broadest location within the section of the blood vessel that is analyzed. In response to detecting the lesion, QVA is performed with respect to the lesion. For some applications, the lesion is graphically indicated, for example, by highlighting or coloring the section of the vessel that is determined to be the lesion.

For some applications, a lesion is automatically detected in accordance with the following procedure. Scan lines are generated perpendicular to the centerline of a segment of the vessel that is sampled. The image is resampled along the scan lines. Corresponding gray-level values are stored as columns of a rectangular matrix M, thereby resampling the segment of the vessel as a straightened vessel segment. For the straightened vessel segment, optimum upper and lower paths are determined (with respect to the middle row of M), which connect the first and last columns of M. The optimization criterion takes into account the changes in gray-level along columns of M, and the paths' slopes. The vessel edge lines are obtained via back projection of upper and lower optimal paths on the original image.

A shortest path algorithm (such as that described by Dijkstra) is used in order to avoid irregularities, such as small gaps and loops, in the edge lines. For some applications, the centerline is corrected based upon the detected edge lines, and new scan lines are constructed. For each new scan line, vessel diameter is defined as a distance between the two points where the scan line intersects vessel boundaries.

For some applications, the technique described for the automatic identification of a lesion is used to automatically identify a guiding catheter. Typically, based on the known diameter (or another known dimension) of the catheter, image units (i.e., pixels) are converted to absolute units (e.g., millimeters or French units). Thus, for some applications, measurements are provided in absolute units, such as, lesion length, the diameter of the vessel at each point along the centerline, and/or minimum lumen diameter (which is also known as the MLD). For some applications, the level of occlusion (which is typically provided as a percentage) at the minimum lumen diameter is determined by comparing the diameter of the vessel at that point, to the diameter of the vessel at reference points of the vessel.

For some applications, in response to the user designating the single location (as described hereinabove), edge detection and QVA are automatically performed up until proximal and distal locations that are at suitable distances along the vessel in, respectively, proximal and distal directions. For some applications, QVA is performed at distances along the vessel from the location that are equal in both proximal (i.e., typically upstream) and distal (i.e., typically downstream) directions along the vessel. Alternatively, the proximal distance is greater than the distal distance. For example, in some cases it may be planned for a stent to be deployed at a lesion within the blood vessel, such that the majority of the stent is deployed proximal of the center of the lesion. Therefore, in response to the user designating the center of the lesion, the QVA is performed up to a distance along the blood vessel in the proximal direction that is greater than the distance along the blood vessel along which the QVA is performed in the distal direction. Further alternatively, the proximal distance is less than the distal distance (for example, in cases in which the center of a stent is to be deployed at a location that is distal with respect to the center of a lesion).

For some applications, the maximum total distance along the blood vessel along which QVA is performed typically automatically, is equal to the length of the longest balloon or stent that is used with the system. For some applications, the total distance along the blood vessel along which QVA is performed is equal to the length of the stent most likely to be used. In accordance with respective applications of the invention, such distances are preset, or are indicated by the user.

For some applications, the narrowest location within the region with respect to which the QVA is performed is marked, and/or the minimal lumen diameter at that location is indicated at that location. As described hereinabove, for some applications, the system automatically detects the reference diameters of a lesion. For some applications, the diameter of the lumen at the healthy shoulders is displayed. As described hereinabove, for some applications, the system automatically performs QVA along a given distance along the vessel. For some applications, the system automatically detects reference diameters of a lesion within that distance, and (optionally) displays the diameter of the lumen at the healthy shoulders of the lesion. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user moves a cursor (i.e., a manually controlled indicator on a computer screen) along (i.e., through, on, beside, over, or parallel to the length or direction of) the designated vessel in the image, and interactively receives an indication of the vessel's diameter at the current location of the cursor. Alternatively or additionally, the user receives an indication of the minimum lumen diameter, or of reference diameters of a lesion in the vicinity of the current location of the cursor. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user designates a first location with the cursor. Subsequently, the user moves the cursor along the blood vessel and receives an indication of the average diameter, the minimum diameter, and/or another quantitative measure of the blood vessel between the first location and the current location of the cursor. Alternatively or additionally, the user moves a cursor along the designated vessel and interactively receives an indication of the longitudinal distance between the current location of the cursor and the first location, the proximal end, and/or the distal end, of the vessel. Further alternatively or additionally, the user receives an indication of the minimum lumen diameter, or of reference diameters of a lesion in the vicinity of the current location of the cursor. For some applications, the level of occlusion of the blood vessel at the minimum lumen diameter is determined by comparing the minimum lumen diameter to the reference diameters, for example, by comparing the minimum lumen diameter to an average of the two reference diameters.

For some applications, the user moves a cursor along the designated vessel and interactively receives an indication of the longitudinal distance between the current location of the cursor and the proximal location of the vessel described hereinabove. Alternatively or additionally, the user moves a cursor along the designated vessel and interactively receives an indication of the longitudinal distance between the current location of the cursor and the distal location of the vessel described hereinabove. Typically, the aforementioned longitudinal distances are calculated along the vessel's center line. Further typically, the distances are determined based upon some known anatomical feature, or based upon a known dimension of another element that is, or has been, present in the image stream, as described hereinabove.

For some applications, the interactive QVA techniques described in the previous paragraph are used to replace virtual stenting. For example, instead of determining which stent should be placed at a lesion by graphically generating a virtual stent at the lesion, QVA is performed with respect to the lesion. Based upon the QVA, it is determined which stent should be placed at the lesion, and/or specific dimensions of a stent that should be placed at the lesion.

For some applications, as the user moves the cursor over the vessel, the portion of the vessel over which the cursor has moved is graphically indicated, for example, by highlighting or coloring the section of the vessel over which the cursor has moved. For some applications, in this manner, the user generates a graphical indication of a lesion. For some applications, such graphical indication of the lesion is used to replace virtual stenting.

For some applications, in response to an input from the user, the processor only allows movement of the cursor on the screen along (i.e., through, on, beside, over, or parallel to the length or direction of) paths of the blood vessels. For example, the cursor may be allowed to move along center lines, or other lines within the blood vessels. Or, the cursor may be allowed to move alongside the blood vessels but in a direction that is parallel to paths (for example, center lines) of the blood vessels. For some applications, the user moves an input device such as a joystick or mouse in a given direction (e.g., left or right), while the system constrains the actual on-screen movement of the cursor to the proximal and distal directions of the closest blood vessel. (In the context of the present application, the term 'cursor' should be understood to refer to any form of on-screen indication of a location provided by a user input device.) Alternatively or additionally, the input device (e.g., the joystick) provides haptic feedback to the subject by constraining movement of the input device to directions that correspond to paths of blood vessels.

For some applications, a "derived" feature is displayed inside or adjacent to the blood vessel, or at a different location in the image. The derived feature may be a diameter line (e.g., diameter line 142 in FIG. 38B), or a percentage of narrowing relative to a reference diameter of the blood vessel at a location, or the minimum lumen diameter of a vessel segment, or an indication of the reference diameters corresponding to a longitudinal location of the vessel, or a combination thereof. The derived feature typically corresponds to the current longitudinal location of the cursor along the blood vessel. For example, the percentage of narrowing, relative to a reference diameter, of the blood vessel at the current longitudinal location of the cursor may be displayed (typically in an alphanumeric format). Or, the minimum lumen diameter of a vessel segment corresponding to the current longitudinal location of the cursor may be displayed.

For some applications, the feature is displayed at a longitudinal location, within or along the vessel, which corresponds to the location of the cursor. For example, the diameter line may be displayed inside the vessel at the current longitudinal location of the cursor. In response to movement by the user of the input device, the derived feature is moved within or along the vessel to a location that is derived from the current position of the cursor. For some applications, the feature is displayed at an in-vessel location that is the closest in-vessel location to the location of an out-of-vessel cursor that is displayed alongside the blood vessel. For some applications, in response to movement by the user of the input device, the processor only allows movement of the feature on the screen along paths of the blood vessels. In accordance with respective embodiments, the processor only allows movement of the feature on the screen along paths of the blood vessels, with or without restricting movement of the cursor to being along the paths of the blood vessels.

Figure 38A:
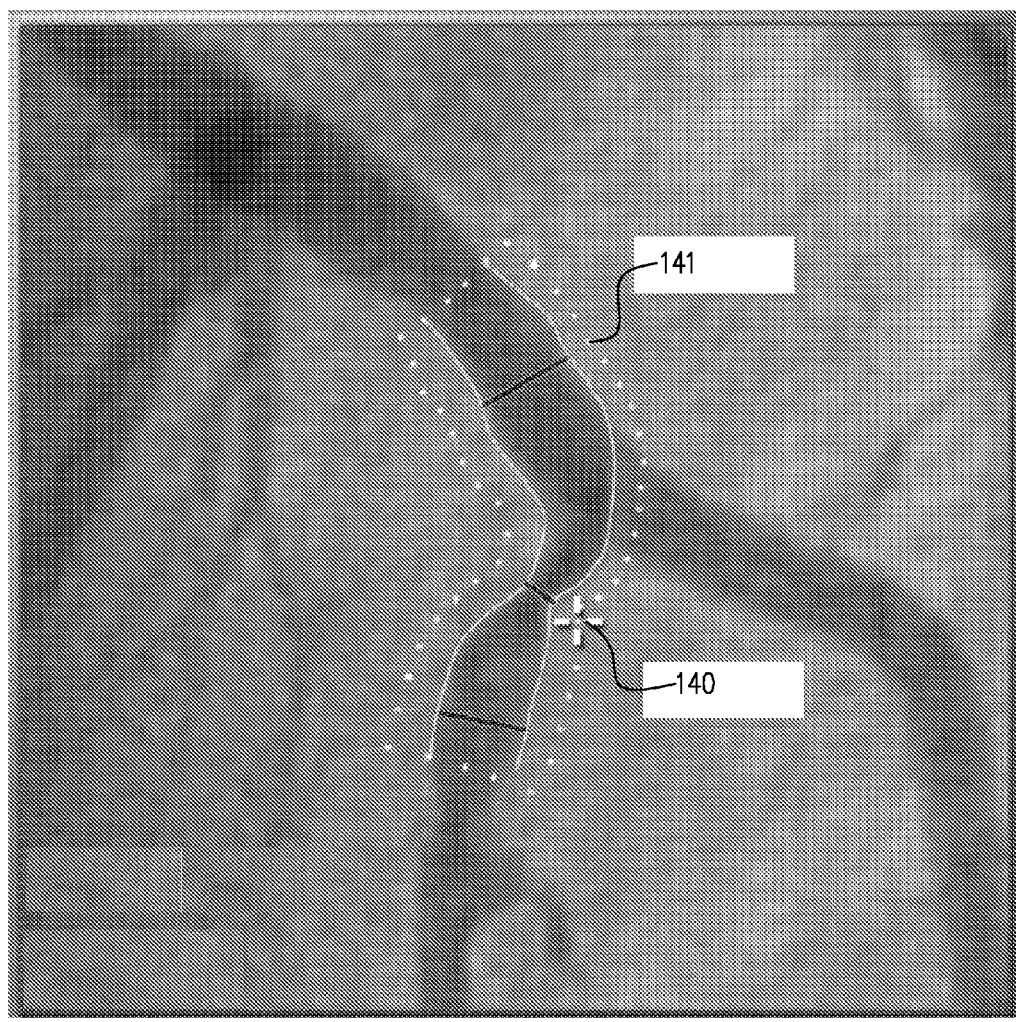
FIGS. 38A, 38B, 38C, and 38D show the movement of a cursor on an image of one or more blood vessels, and the display of a derived feature (or another output) on the image based upon the current location of the cursor with respect to the vessels, in accordance with some applications of the present invention.

Reference is now made to FIGS. 38A-D, which are schematic illustrations of the movement of a cursor 140 on an image of one or more blood vessels, and the display of a derived feature (or another output) on the image based upon the current location of the cursor with respect to the vessels, in accordance with some applications of the present invention. For some applications, a virtual envelope 141 (indicated by dotted lines in FIG. 38A) is automatically defined by the system along a displayed blood vessel or a section thereof. The virtual envelope is a virtual region around the blood vessel that the system defines (typically according to defined parameters, as described hereinbelow) and uses, for example, to apply the techniques described hereinbelow. Typically, the virtual envelope is not actually shown to the user. However, the scope of the present invention includes showing the virtual envelope to the user, for example, as shown in FIG. 38A.

In accordance with respective embodiments, the envelope is defined in two dimensions or more. For example, a three-dimensional envelope may be applied to cardiac CT or cardiac MRI images. Furthermore, in accordance with respective embodiments, the virtual envelope is defined by the system based upon a distance from the vessel's center lines or edge lines, the distance being measured in either image pixels or physical units. For example, the distance of the outer extent of the envelope from the vessel center line may be more than 0.5% (e.g., more than 1%), and/or less than 5% (e.g., less than 2%) of the total number of pixels that are displayed across the width of the display. Alternatively or additionally, the distance of the outer extent of the envelope from the vessel center line may be more than 25% (e.g., more than 40%), and/or less than 75% (e.g., less than 60%) of the number of pixels that correspond to the diameter of the vessel. Further alternatively or additionally, the distance of the outer extent of the envelope from the vessel center line may be a fixed number of pixels, e.g., more than 5 (e.g., more than 10), and/or less than 40 (e.g., less than 20).

Typically, as long as the input from the user, via the input device, indicates that the cursor is within the virtual envelope of a given blood vessel, an output is displayed on the image corresponding to the given blood vessel. For example, the cursor or a corresponding derived feature (such as a diameter line, as described hereinabove) may be displayed inside or alongside the blood vessel, and/or the actual on-screen movement of the cursor, or of the corresponding feature, may be constrained along the proximal and distal directions of the blood vessel ("the first vessel").

Figure 38B:
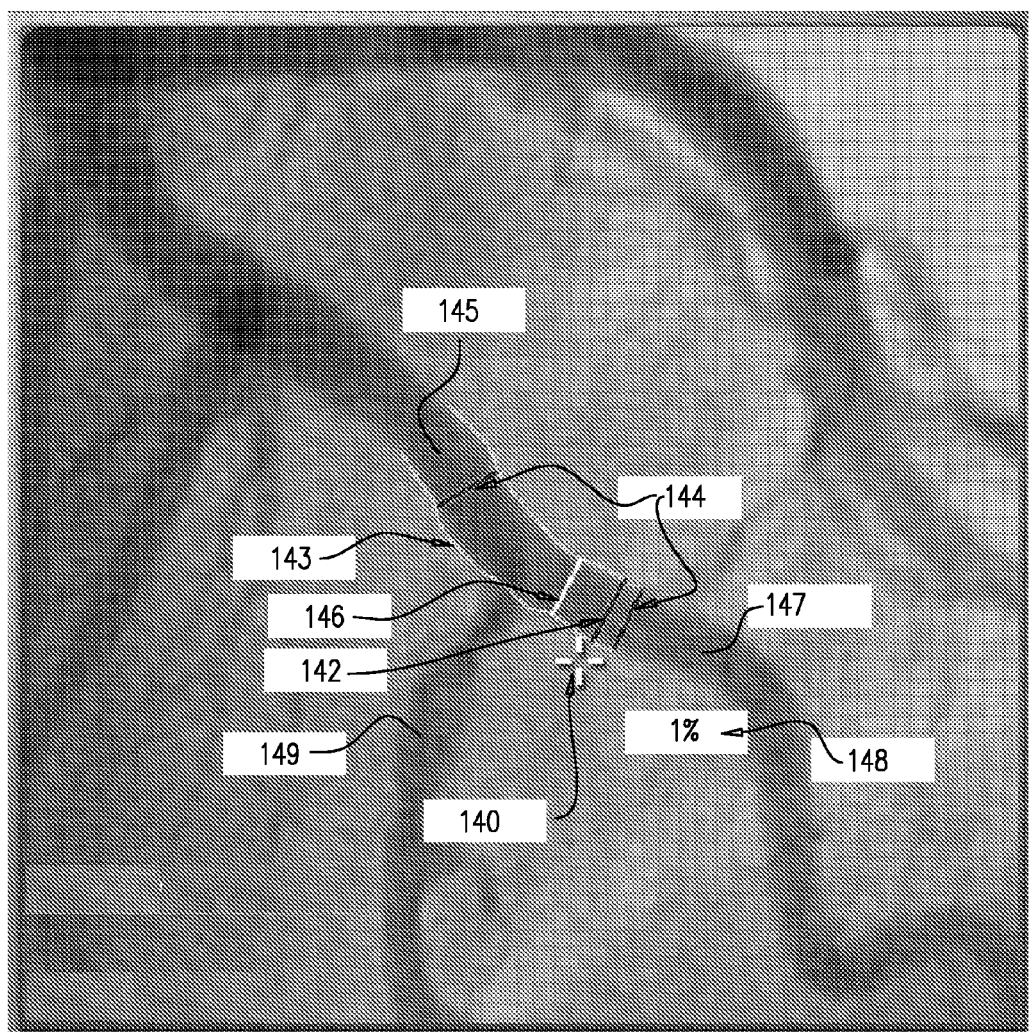
Figure 38C:
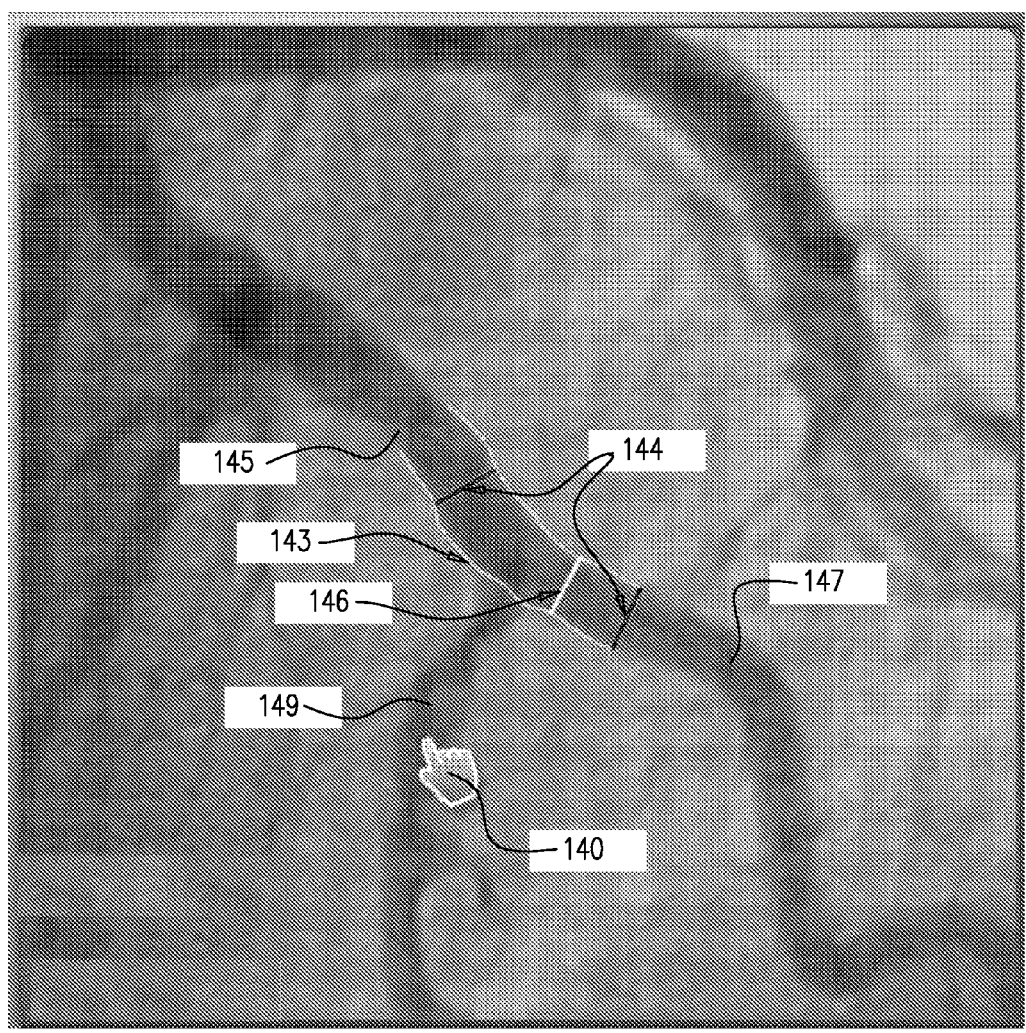
Figure 38D:
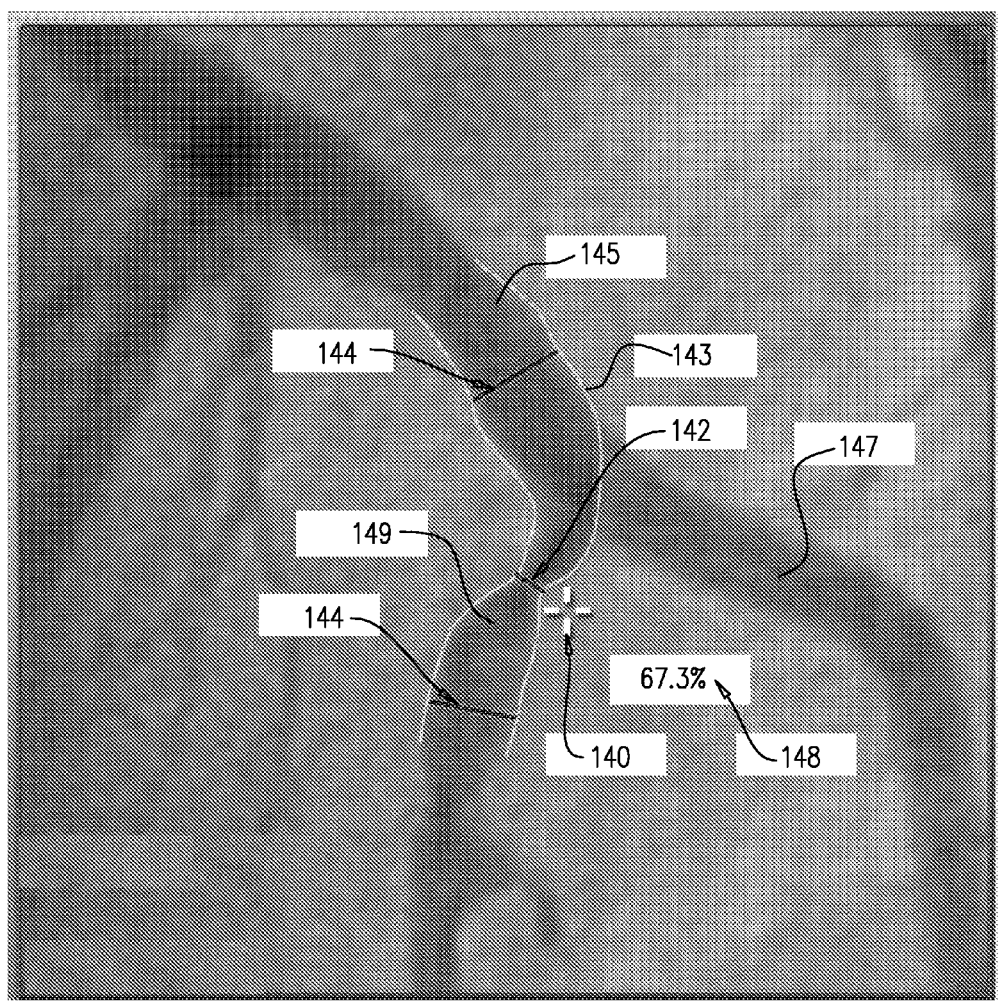

For some applications, as shown in FIGS. 38B-D, a virtual envelope is used in the performance of QVA (and/or virtual stenting) on a vessel segment comprising the bifurcation of a main vessel 145 into two or more branches (e.g., a main branch 147 on the right, and a side branch 149 on the left, as shown). As long as the cursor is within the virtual envelope, QVA (and/or virtual stenting) is performed upon the currently-selected branch of the bifurcation. However, once the cursor exits the virtual envelope, the system searches for another branch of the bifurcation (or another blood vessel), identifies the other branch (or blood vessel) and performs QVA (and/or virtual stenting) on the other branch (or blood vessel), all according to the vessel identification and QVA principles described hereinabove.

For some applications, the search for the other branch is performed automatically by the system, e.g., in response to the cursor being moved out of the envelope of the first branch. Alternatively or additionally, the search is performed, or initiated by the user, for example, by the user indicating that the system should perform the search (e.g., by clicking a mouse), subsequent to moving the cursor out of the virtual envelope. For some applications, the system identifies blood vessels and corresponding envelopes over the entire image, or over an entire portion of the image, prior to the user moving the cursor out of the virtual envelope of the first vessel. For such applications, the system searches for the other blood vessel by searching for an already-defined vessel envelope in the vicinity of the current location of the cursor. Alternatively, in response to the current location of the cursor, the system identifies vessels and corresponding envelopes in the vicinity of the cursor.

For some applications, the current location of the cursor is interpreted by the system as an indication that there is an increased probability that there is a blood vessel in the vicinity of the current location of the cursor than in another portion of the image. For example, the vesselness of pixels in the image (as defined hereinabove) may be weighted such that pixels in the vicinity of the current location of the cursor are assigned a greater weight than pixels in another portion of the image. For some applications, weightings are applied to the vesselness of pixels that are inversely related to the distance of the pixels from the current location of the cursor.

For some applications, prior to performing QVA on one or both of the branches, the system automatically defines a vessel segment that includes a portion of the main vessel. A graphic representation of the vessel segment is generated that includes one or both of the branches and a portion of the main vessel. The identification by the system that the branch and the main vessel form a single continuous vessel segment may be made by connecting vessel edge lines, or vessel center lines, or both.

FIG. 38B shows cursor 140 in a vicinity of (i.e., inside the virtual envelope of) a vessel, with the cursor represented as a small cross and a corresponding in-vessel diameter line 142, typically, at the location closest to the cursor. As described hereinabove, the vessel segment shown is a bifurcation, with a vessel segment having been identified that includes the main vessel 145 and the main branch 147. The edges 143 and reference diameters 144 of the vessel segment are marked, as is the minimum lumen diameter 146 in the segment. Analysis is performed with respect to the vessel segment, in accordance with the techniques described hereinabove. For some applications, the percentage occlusion 148 relative to the reference diameter, at the current location of the in-vessel diameter line, is also displayed, in alphanumeric format. Alternatively or additionally, the minimum lumen diameter of the vessel segment is displayed.

Once the cursor is moved outside the virtual envelope, the system searches for another blood vessel (or a vessel that branches from the first vessel) in the vicinity of the cursor, according to the principles for identifying a blood vessel described hereinabove. As described hereinabove, in accordance with respective embodiments, the search is initiated automatically, or in response to an input from the user, and the search is performed on already-identified blood vessels, or the search includes the identification of new blood vessels. For some applications, once a new vessel (or branch of the first vessel) is selected, subsequent actual on-screen movement of the cursor (or of a corresponding feature) is automatically constrained along the proximal and distal directions of that new vessel (or branch).

For some applications, the on-screen symbol indicating the location of the cursor is automatically changed once outside the aforementioned virtual envelope, to indicate that the system has changed its current mode from constraining movement of the cursor to a current vessel (or branch) to looking for a new vessel (or branch) in the vicinity of the cursor.

FIG. 38C shows on-line cursor 140 positioned further away from (i.e., now outside the virtual envelope of) the analyzed segment of the first vessel, with the cursor having changed its graphical representation from a cross to a small hand. As shown, at this stage, corresponding in-vessel features, such as diameter line 142 shown in FIG. 38B, are no longer displayed. At this stage (and, optionally, in response to an input from the user), the system searches for a new vessel in the vicinity of the current position of the cursor. In response thereto, the system typically identifies a new vessel segment on which to perform QVA, in accordance with the techniques described hereinabove. For some applications, the system provides an indication to the user that a new vessel has been identified, but the performance of QVA on the new vessel is initiated in response to an input from the user (e.g., by the user clicking on the identified vessel with a mouse).

FIG. 38D shows the left-side vessel branch 149, corresponding to the new on-screen location of the cursor, having been identified (and, optionally, selected by the user). In response thereto, a vessel segment has been identified that includes a portion of the main vessel. The graphical representation of the cursor has changed back to a small cross, indicating that a new vessel segment has been identified, and a corresponding in-vessel feature (i.e., diameter line 142) is shown at the location closest to the cursor.

It is noted that although some applications of the present invention have been described with respect to branches of a bifurcating blood vessel, the scope of the present invention includes applying the techniques described herein to other blood vessels, mutatis mutandis. Furthermore, the scope of the present invention includes applying the techniques described with respect to blood vessels to lumens of a subject's body other than blood vessels, for example, a lumen of the gastrointestinal tract or lumens of the respiratory system.

It is noted that although some applications of the present invention are described as being performed in response to a user moving a cursor on a display, the scope of the present invention includes applying such techniques in response to the user designating a location on the display, but without a cursor being displayed, mutatis mutandis. For example, in response to an input from the user via an input device (such as a mouse) indicating a location, a derived feature may be displayed on the display without a cursor being displayed. For some applications, the display is a touch-screen display and the user designates a location on the display by touching the display, with or without a cursor being displayed.

Reference is now made to FIG. 18, which shows QVA diameter diagrams 66 and 68, in accordance with some applications of the present invention. As described hereinabove, for some applications, an ROI 62 is identified (for example, an ROI in an angiogram 65 is identified, as shown in FIG. 18). For some applications, a user identifies and designates the location of the center of a lesion 64, for example, by clicking on the center of the lesion in the angiographic image, or in the enlarged image of the ROI. For some applications, QVA diagram 68 of the lesion is generated, in which both edges of the vessel are illustrated at their original shape in the form of a diameter diagram. In diagram 68, the vessel's edges are aligned and depicted along and at both sides of the vessel's straightened center line, such that the center line serves as the horizontal axis of the diagram. Alternatively or additionally, QVA diagram 66 is generated. QVA diagram 66 is a graph which plots the diameter, or the level (e.g., percentage) of occlusion of the blood vessel (on the y-axis) against the longitudinal distance along the blood vessel on the x-axis. Thus, using diagram 66, the cumulative narrowing at any given point along the vessel may be observed. For some applications, generating diagram 66 facilitates identification of the narrowest location within the occlusion and the extent of narrowing at that location.

For some applications, a sequence of endoluminal cross-sectional images is generated by an endoluminal imaging catheter. Respective cross-sectional images of the blood vessel are assigned as corresponding to regions of an extraluminal image of the blood vessel (for example, by registering the endoluminal images to the extraluminal image). QVA diagrams or measurements are generated for regions of the extraluminal image. Respective cross-sectional images of the blood vessel are displayed together with (e.g., alongside) the corresponding QVA diagram and/or measurements. For some applications, the endoluminal images (with or without the corresponding QVA diagrams and/or measurements) are displayed as stacked and aligned along a straightened center line of the blood vessel. For some applications, the endoluminal images are generated by the imaging catheter during its pullback. In accordance with respective applications, the endoluminal imaging catheter may be, for example, an IVUS catheter, an OCT catheter, a NIRS catheter, an MRI catheter, or any combination thereof.

For some applications, QVA is performed in response to the user clicking at or near two locations along a vessel, the locations indicating the proximal and distal edges of the lesion. For some applications, a graphical window appears on the screen, and the two locations are designated based on how the user positions the edges of the window and/or sizes the window, with respect to the designated vessel. For some applications, the size of the window changes automatically until the user clicks to indicate that the then-current size is to be selected.

Reference is now made to FIG. 19, which shows a QVA diagram 70 comprising a representation of a tool at its relative location within the lesion on which QVA has been performed, in accordance with some applications of the present invention. For some applications, when a tool such as a balloon and/or stent is present at the occlusion at the time a QVA diagram is generated, a representation of the tool, or of radiopaque markers or segments thereof, is incorporated into the QVA diagram with the position of the tool indicated relative to the occlusion, as shown. Typically, the tool representation is displayed within the lesion on the QVA diagram, at a location that corresponds to the actual location of the tool within the lesion. For some applications, the location of the tool relative to the lesion is determined automatically. For some applications, QVA is performed automatically, upon the identification of the aforementioned radiopaque markers or radiopaque segments within a vessel. For example, QVA may be performed on a segment of the vessel between the two markers, or along a pre-defined distance along the vessel from a site that is a given distance beyond one of the markers, or between two sites that are at respective given distances beyond respective markers.

For some applications, the distance indicators in a road map described hereinabove are used for measurements (e.g., automatic measurements). For example, measurements may be performed of (a) the dimensions of an artery, such as the length and/or diameter of the artery, and or (b) the dimensions of a lesion, such as the length and/or diameter of the lesion. For some applications, the diameter of a reference point of the artery (or of a different artery), at one or both sides of an occlusion, is measured. In accordance with respective applications, the reference point of the artery is indicated by the user, or is identified, typically automatically, by means of image processing due to its larger diameter relatively to that of the occlusion. For some applications, the reference point of the artery is assumed by the system to be at a set distance from the center of the occlusion, or at a set distance from the center of an ROI.

Figure 20:
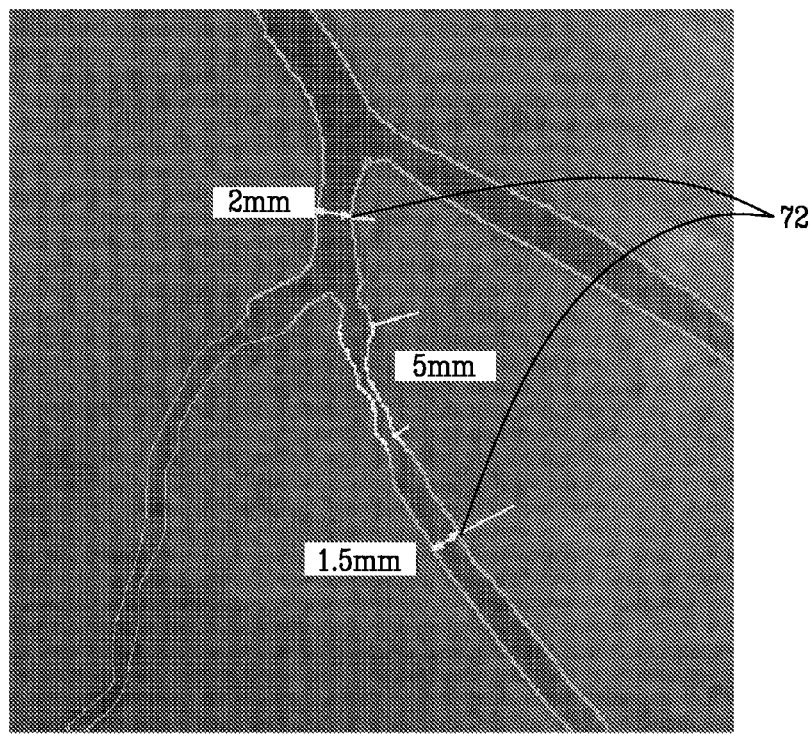
FIG. 20 shows a road map that displays measurements of the diameter of the reference artery at both sides of an occlusion, in accordance with some applications of the present invention.

Reference is now made to FIG. 20, which shows a road map upon which are displayed measurements 72 of the diameter of reference points of an artery on both sides of an occlusion, in accordance with some applications of the present invention.

For some applications, the measurements are used in the selection of a medical tool (e.g., a balloon, and/or a stent) to be deployed at the occlusion.

Image Tracking and Tool Positioning

For some applications, a virtual tool is positioned upon the road map, and/or upon the stabilized images. Typically, the positioning of a virtual tool is an intermediate step leading to the selection and positioning of a corresponding actual tool. For some applications, techniques for the generation and positioning of a virtual tool described in WO 08/107,905 to Iddan, which is incorporated herein by reference, are used in combination with techniques described herein.

For some applications, image tracking is applied to a stream of image frames to facilitate the positioning of a tool, deployment of a tool, the deployment of an already-deployed tool (such as by post-dilatation of a balloon within an already-deployed stent), post-deployment analysis of a deployed tool, general observations, or any combination thereof.

For some applications, image tracking is performed with respect to a radiopaque (or otherwise visible) segment or marker(s) of the tool, which is/are visible in most or all image frames and are identified automatically by means of image processing. The tool is aligned in image frames of the image stream, based on the identified markers or segment of the tool. For example, the image frames may be aligned such that markers in at least most of the image frames are aligned. The aligned image frames are displayed as an image stream. For some applications, image frames are tracked in the aforementioned manner, but with respect to a portion of the subject's anatomy, for example, vascular calcification of the subject.

For some applications, the tool with respect to which image frames are tracked is a balloon, a marker wire, a guide wire, a stent, an endoluminal imaging catheter (e.g., a catheter that uses an imaging modality that is MRI, OCT, IVUS, NIRS, ultrasound, or any combination thereof), and/or an endoluminal measurement catheter (e.g., an FFR catheter).

The identification of the markers or radiopaque segments is typically performed automatically by the system. For some applications, the identification is performed within one or more entire image frames. Alternatively, the identification is performed within an ROI which was previously set by the system and/or the user. Further alternatively, the ROI is automatically set by the system to include regions in which the markers are more likely to appear, and to exclude regions in which the markers are less likely to appear. For some applications, the ROI is indicated graphically, overlaid upon the image stream.

For some applications, markers are identified by the user designating a region within the image in which the markers are more likely to appear, followed by the system automatically identifying the markers within that region. For some applications, the user is subsequently prompted to confirm the identification selection of markers by the system. In accordance with respective applications, the region is designated by the user within a dynamic image stream, or within a static image frame taken from within the image stream. Alternatively, the user clicks on (or otherwise indicates) the device or the vicinity of the device, and, in response, the image tracking with respect to the device markers or segments commences.

Once the markers have been identified in one or more image frames, then the system typically continues to identify (i.e., detect) those markers automatically in the subsequent image frames along the image stream or a segment thereof, and displays a tracked image stream. Typically, in order to detect the markers, the system accounts for phenomena such as the following:

(1) In some image frames, contrast agent may hide, or partially hide the markers. Typically, if the markers are not visible due to the contrast agent in a given frame, then that frame is skipped and is not used in the image-tracked image stream. For some applications, the system identifies markers in image frames in which the markers are partially hidden by the contrast agent, and the image frames are used in the image-tracked image stream.

(2) A fluoroscopic image is typically a two-dimensional projection of the three-dimensional portion of the subject's body that is being imaged. This may result in darkened regions, which appear similar to markers, but which are not markers. For example, regions of the image in which vessels (particularly vessels that contain contrast agent) are projected onto the two-dimensional image such that they appear to be crossing each other, may appear as a dark circle. Similarly, regions in which a tool crosses a vessel, two tools cross each other, a tool crosses the edge of a rib, or a vessel crosses the edge of a rib, may appear similar to a marker. Examples of such tools include a wire (such as a CABG wire, or a guide wire), a CABG clip, an electrode, a lead, and/or a catheter lumen.

(3) In a dynamic image stream, markers may be blurred due to the rapid movement of blood vessels.

For some applications, image frames in which the markers are not identified are automatically skipped. For some applications, blending is performed among tracked image frames which may further stabilize the tracked image frames. When image frames of the original image stream are skipped (e.g., due to non-identification of a marker), then the transition between the adjacent image frames to the skipped image frame is typically performed with blending.

For some applications, a mask is applied to the tracked image stream such that the areas more remote from the tracked markers, which typically have greater motion in the tracked image stream, are blurred, hidden, or partially hidden. Such a masked image stream may be easier for a user to observe, because of the reduction in distractions in the tracked image stream. Alternatively or additionally, the periphery of the image (e.g., the anatomy outside the vascular system) is blurred, hidden, or partially hidden.

For some applications, the automatic identification of markers comprises some or all of the following phases, which are typically performed in real time:

a. Pre-processing: Individual image frames (or an ROI within such frames) along the image sequence are pre-processed in order to facilitate the subsequent identification of markers. Such pre-processing typically comprises the reduction of static and/or dynamic noise, background removal, or a combination thereof. For some applications, a median filter, a Mexican hat filter, a directional Mexican hat filter, and/or a low-pass filter is applied to the individual image frames. For some applications, the preprocessing includes the detection and removal from the image frames of CABG wires, wires and/or electrodes of implanted tools such as pacemakers or defibrillators, and/or wires and/or electrodes of external devices such as an ECG monitor, and/or an external defibrillator.

b. Filtering of non-marker-like features: Individual image frames (or an ROI within such frames) along the image sequence are processed to filter out remaining features that are clearly not markers. For some applications, the filtering includes the application to the image frames of a median filter, a Mexican hat filter, a directional Mexican hat filter, a maximal stable external regions (MSER) filter, an MSER-like filter, a Hessian filter, or a combination thereof.

For some applications, Hessian eigenvalues are calculated for each pixel in each image frame, or for all pixels within an ROI of the image frame. Typically, local clusters of pixels with high minimal eigenvalues represent a "paraboloid-like" area in the image and are identified as a potential radiopaque marker.

c. Scoring: Remaining features in individual image frames (or an ROI within such frames) along the image sequence are assigned a "fitness" score (i.e., a "markerness" score, or a "dotness" score in the case of the most common markers), describing the likelihood that they are markers. For some applications, the score is calculated from the abovementioned filtering.

d. Matching: Remaining features in individual image frames (or an ROI within such frames) are analyzed for matching with one another. For example, in the case of aiming to detect the two radiopaque markers of a coronary balloon, pair matching is performed. Such matching is typically performed based upon relative location, distance, orientation, visual similarity, and/or other factors.

e. Detection: For some applications, once a pair of clusters (with such two clusters being strong candidates to be tool markers) has been identified at a similar distance from one another and/or relative angle to one another in several consecutive image frames, the pair of clusters is determined to be the two markers of a tool.

f. Tracking: Typically, image tracking, as described hereinabove is performed with respect to the two markers for the purposes of image stabilization and/or enhancement.

It should be noted that while using a pair of radiopaque markers as a primary example, the techniques disclosed above (or a derivation thereof) may be applied to other radiopaque (or otherwise visible) segment(s) or marker(s) or feature(s) of a tool, or feature(s) of the anatomy, which are visible in most or all image frames.

For some applications, for the purpose of image tracking, the identified segment or marker(s) of the tool is aligned automatically in most, or all, image frames such that it remains at a similar or same relative position throughout the image stream. Further typically, this results in the tool being aligned automatically in most, or all, image frames such that it remains at a similar or same relative position throughout the image stream.

For some applications, a virtual line that connects the markers is aligned such that it remains at the same or a similar relative position throughout the image stream. For example, the alignment may include translating individual image frames such that the markers (or the virtual line connecting the markers) remain at a same or similar location within the image frames throughout the tracked image stream. Alternatively or additionally, the alignment includes rotating individual image frames such that the angle of the virtual line connecting the markers is same or similar throughout the tracked image stream. Further alternatively or additionally, the alignment includes scaling of individual image frames such that the distance between the markers is the same throughout the tracked image stream. For some applications, the alignment is performed with respect to a virtual feature calculated from the individual locations of the markers. For example, the virtual feature may be an average between the locations of the individual markers, or a weighted average of the locations of the individual markers.

For some applications, image tracking on markers, or on a virtual feature derived from the markers, continues for as long as certain parameters pertaining to such markers are observed at similar values in at least most of the image frames (or in a ROI within such frames). For example, the parameters may include the markers' location, distance from one another, angle relative to one another, linear velocity between consecutive frames, angular velocity between consecutive frames, sizes, "markerness" score, x-ray intensity, surrounding intensity gradients, or any combination thereof.

Typically, the aforementioned image tracking results in the tool being displayed as relatively stable, while the surrounding anatomy is displayed as moving relative to the generally-stable tool in the course of the organ's motion cycle.

For some applications, visibility of image elements surrounding the tool is reduced in the displayed, tracked image stream, in order to reduce visual distractions. Typically, such reduction in visibility facilitates observation of the tool and the vicinity of the tool within the tracked image stream. For some applications, the reduction in visibility is achieved by applying a mask to the images, such that the visibility of regions of the displayed tracked images that are relatively remote from the tool is reduced. For some applications, the visibility of the image elements is reduced gradually, such that there is a typically inverse relationship between the distance of an image element from the tool and the visibility of such image element in the displayed, tracked images.

For some applications, in the region of the tool, pixels are displayed that are not averaged. Pixels that are distant from the tool are averaged with pixels from other image frames that are in a corresponding location to those pixels, for example, as described hereinbelow. For some applications, there is a direct relationship between the extent to which pixels are averaged, and the distance of the pixels from the tool.

Image tracking with respect to a portion of the tool typically effects a visual separation between two elements of the motion of the tool positioned within a vessel attached to the heart. The motion of the tool together with the vessel is typically hidden, while the motion of the tool relative to the vessel typically remains visible. For some applications, such separation of motion elements typically facilitates the ability of the user to determine the extent of the motion of the tool relative to the vessel (e.g., cyclic longitudinal motion within the blood vessel) in the course of the heart's motion cycle. That, in turn, typically enables the user to determine the importance of deploying the tool at a specific phase in the motion cycle, and if so, at which specific phase, and location.

For example, when placing a balloon (or a balloon carrying a stent) relative to a designated lesion within a coronary artery, image tracking is performed on the radiopaque marker(s) of the balloon. Consequently, the motion of the balloon together with the artery, in the course of the heart's motion cycle, is typically hidden. At the same time, the motion of the balloon relative to the artery, in the course of the heart's motion cycle, typically remains visible. Consequently, the user can observe (typically while being demonstrated by contrast agent) the location of the balloon prior to its inflation, and/or the stent prior to its deployment, at a systolic or end-systolic phase versus a diastolic or end-diastolic phase. Based on the observed locations of the balloon or the stent, deployment of the balloon or the stent at a desired location is timed to the phase in the cardiac cycle at which the pre-deployment position is at the desired location.

In accordance with respective applications, the user observes the balloon in the described manner, in real time, in near real time, or in reloop mode.

For some applications, the extent of the motion of the balloon relative to the artery is quantified automatically. For example, the location of the tool's markers or radiopaque segments relative to a known anatomical feature (such as an occlusion, a bifurcation, an ostium) is automatically determined over the course of a cardiac cycle.

For some applications, image tracking is performed with respect to the radiopaque segment(s) of a tool configured to penetrate an occlusion. The inventors hypothesize that such image tracking facilitates determination by a user of the orientation of the tool relative to the vessel at any given moment, and thus assists the operator in determining when to push forward and/or activate the tool.

For some applications, identification of the end-diastolic and end-systolic points within a cardiac cycle is determined from an ECG signal, and/or by means of image processing. For example, such means of image processing may include the identification of a reversal of the direction in which a tool's radiopaque segment(s) moves.

For some applications, the possibly-varying location of the tool vis-à-vis the vessel in the course of the heart's motion cycle is further highlighted by graphical means. For example, portions (such as the radiopaque segment(s) or marker(s)) of the tool may be presented in different colors, shapes, textures and/or sizes at a systolic or end-systolic phase versus a diastolic or end-diastolic phase. Alternatively or additionally, other elements in the image frames change their appearance according to the phase in the motion cycle. Further alternatively or additionally, sounds are used to denote a selected phase in the motion cycle.

Figure 21:
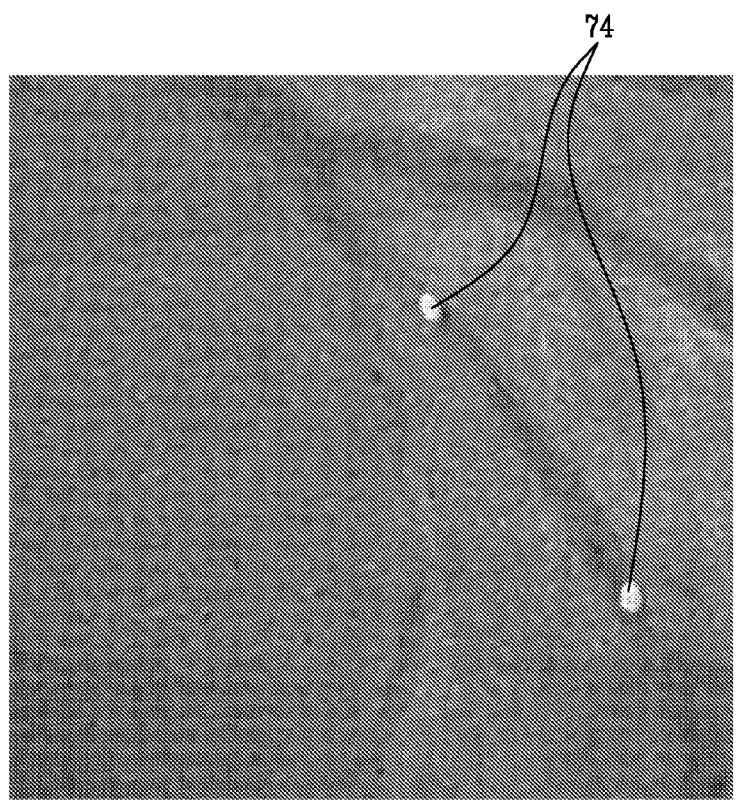
FIG. 21 shows markers of a balloon that are highlighted during at least one given phase of the cardiac cycle, in accordance with some applications of the present invention.

Reference is now made to FIG. 21, which shows markers 74 of a balloon within a vessel in an angiogram. For some applications, the markers are artificially colored a first color in one phase of the cardiac cycle (e.g., the end-systolic phase), and are colored a different color in a different phase of the cardiac cycle (e.g., the end-diastolic phase).

Figure 22A:
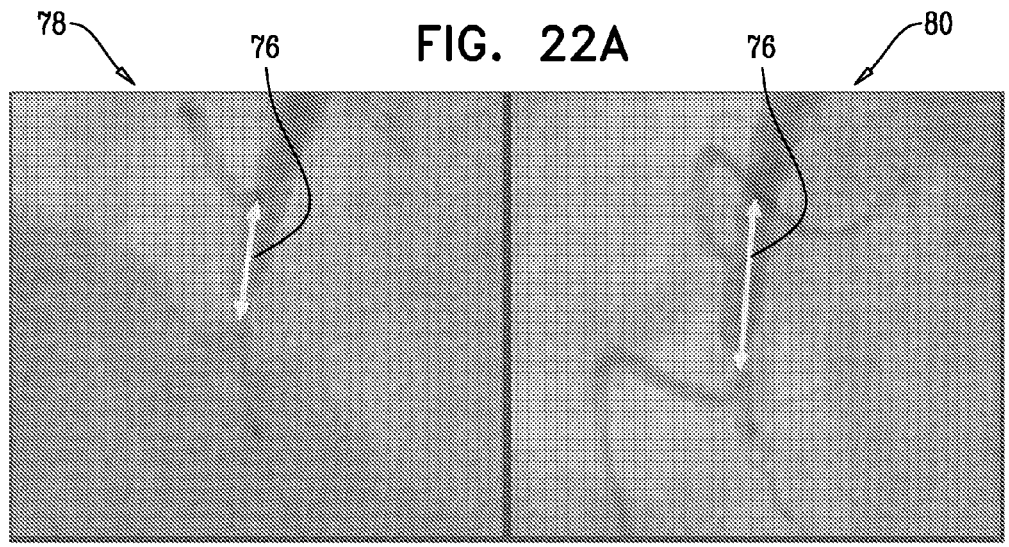
FIG. 22A shows two stabilized images of markers of a balloon inside an artery, at respective phases of the cardiac cycle, in accordance with some applications of the present invention.

Reference is also made to FIG. 22A, which shows images 78 and 80 of markers of a balloon situated within a coronary artery, at respective phases of the subject's cardiac cycle. Arrow 76 in each of the figures denotes the distance of the upper marker from the beginning of an occlusion of the coronary artery. It may be observed that the pre-deployment position of the marker relative to the artery is substantially different at different phases of the cardiac cycle, indicating to the inventors that proper deployment at a desired location should to be timed to the phase in the cardiac cycle at which the pre-deployment position is at the desired location.

Figure 22B:
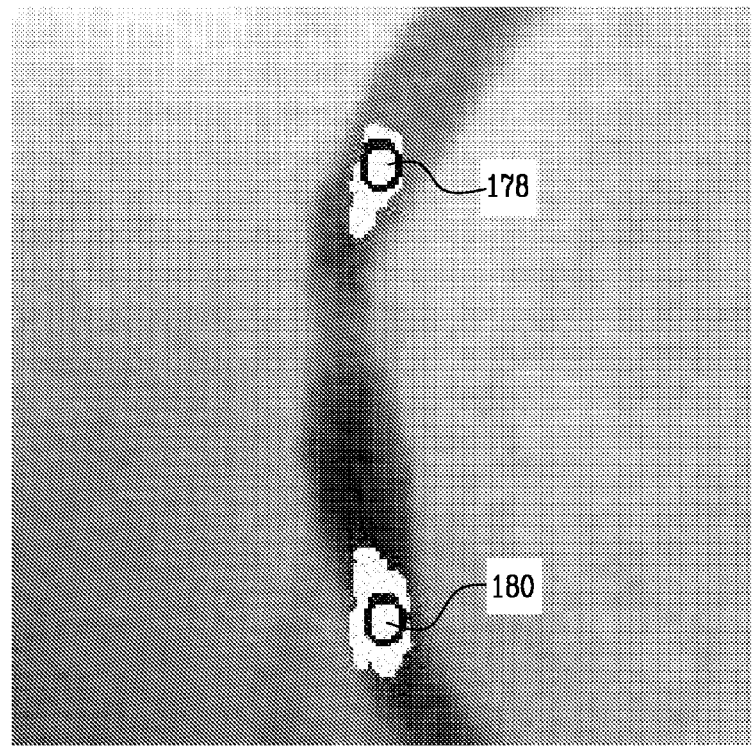
FIG. 22B shows clouds representing markers of a tool inside an artery displayed on an image of the artery that has been enhanced and stabilized with respect to an anatomical feature of the artery, in accordance with some applications of the present invention.

Reference is now made to FIG. 22B, which shows clouds 178 and 180, representing markers of a balloon or a different tool inside an artery displayed on an image of the artery that has been enhanced and stabilized with respect to an anatomical feature of the artery, in accordance with some applications of the present invention. For some applications, a balloon carrying a stent is positioned at a lesion (e.g., a narrowing) within a coronary vessel. A corresponding angiographic image sequence is stabilized, and, optionally enhanced, with respect to an anatomical feature of the vessel, for example, with respect to the narrowing, in accordance with the techniques described hereinbelow.

For some applications, by virtue of stabilizing the image stream with respect to the narrowing in the vessel, the (for example) two radiopaque markers from the individual image frames appear as two clouds, since the markers move with respect to the narrowing, due to motion of the stent with respect to the vessel. Alternatively, movement of the markers with respect to the vessel is determined by the system, in accordance with the techniques described hereinbelow. A representation of the determined movement of the markers with respect to the vessel is generated on the image, for example, by generating clouds 178 and 180 on the image. For some applications, a plurality of stabilized image frames are combined (e.g., added, and/or averaged) into a single image frame (i.e., a composite image frame) and the clouds are displayed on the single image frame. The clouds indicate regions of the image in which the markers appeared during the period of time in which the plurality of stabilized image frames were acquired. Thus, the clouds indicate relative tool-to-vessel motion resulting from the cyclical motion of the vessel. For some applications, such visual information is used by the operator in order to determine the preferred length and positioning of the pre-deployed stent such that upon deployment, the stent would be most likely to cover the entire narrowing.

For some applications, rather than showing clouds 178 and 180 on a single, composite image frame, movement of the markers is shown on an image stream. For example, an image stream that is stabilized with respect to a feature of the vessel may be displayed. By displaying the image stream that is stabilized with respect to the feature of the vessel, movement of the markers with respect to the vessel over the course of the image stream is automatically displayed. For some applications, the stabilized image stream is overlaid on a (typically composite) stabilized stationary image frame, such that the movement of the markers over the course of the image stream may be observed, with respect to an image of a stationary vessel.

The size of the clouds typically serves as an indication of a need to use a mechanism for facilitating synchronized actuation and/or movement of a tool, e.g., synchronized inflation of the balloon (as described hereinbelow, for example, with reference to FIGS. 39A-D). Typically, a greater length of the clouds indicates a greater need to use a mechanism for facilitating synchronized actuation and/or movement of the tool, since this indicates greater movement of the tool with respect to the vessel due to motion of the vessel. Thus, for some applications, in order to determine the extent of the movement of a tool with respect to a vessel, a composite image, and/or an image stream as described with reference to FIG. 22B is displayed. For some applications, such a composite image, and/or such an image stream is displayed in order to determine whether there is a need to use a mechanism for actuating a tool in a synchronized manner.

For some applications, techniques are provided for facilitating the determination of the location of a tool, such as a balloon or a balloon carrying a stent, with respect to an artery, during image sequences for which a contrast agent has not been administered to the subject. For some applications, the current locations of radiopaque markers or radiopaque segments of the tool are determined with respect to a road map that was generated from a previously—acquired angiogram. Typically, the procedure includes some or all of the following phases, and is typically performed in real time:

a. A road map is generated, typically automatically, for example, according to techniques described hereinabove. Typically, the road map is updated automatically during the procedure, in response to the system detecting that a new angiographic sequence has commenced, as described hereinabove. For some applications, commencement of the new angiographic sequence is detected even when the angiographic sequence is performed under fluoro mode. For some applications, the shape of a vessel through which tools are inserted changes in the course of the procedure due to occlusions being reduced, the tool itself straightening the artery, and/or other reasons, and the road map is updated in order to account for these changes.

b. Features residing within the vessel at a relatively fixed location are identified, such features being observable even in images generated in the absence of contrast agent. Such features may include a distal portion of the guiding catheter through which the tool is inserted, a radiopaque portion of the guide wire upon which the tool is inserted, and/or other features. For some applications, the identification of such features is automatic, or semi-automatic (i.e., requiring some user interaction but less than would be required without using the techniques described herein), for example, in accordance with techniques described hereinabove. For some applications, the entire length of the guide wire (or of the catheter carrying the tool) is identified, for example using techniques similar to the ones described hereinabove for the automatic identification of center lines.

c. A current image stream of the tool inside the blood vessel is generated. The markers or radiopaque segments of the tool that is currently inserted into the blood vessel are identified in the image stream, typically automatically and typically in real time, according to techniques described hereinabove. The markers or radiopaque segments are identified even in current images generated in the absence of contrast agent (and in which the artery itself is not visible). The location of the markers with respect to the observable features is determined based upon the current image stream.

d. The tool markers or radiopaque segments are projected, typically automatically and typically in real time, upon the previously-generated road map. Typically, the current location for marker projection within the road map is calculated relative to the aforementioned observable features described in step b. For example, the current distance(s) of the markers from the observable feature(s) (as determined in step c) may be applied along the applicable vessel in the road map in order to determine the location on the road map at which the markers will be projected. For some applications, the angiogram from which the road map is generated is gated to a specific phase in the cardiac cycle (e.g., the end-diastolic phase), and the location of the markers with respect to the observable features is determined in a current image frame that is also gated to that phase.

In an alternative application, the road map is projected (continuously or in a gated manner) upon the image stream that contains the markers or radiopaque segments (as opposed to the image stream being projected upon the road map).

Synchronized Tool Deployment

For some applications, once the location of the tool is suspected to or has been determined to vary in the course of the organ's motion cycle, actuation of the tool is synchronized to a selected phase in the motion cycle of the organ. For some applications, the synchronized actuation of the tool is performed in accordance with techniques described in WO 08/107,905 to Iddan, which is incorporated herein by reference.

For example, when inflating a balloon (or, for example, a balloon carrying a stent) relative to a designated lesion within a coronary artery, and if the pre-deployment position of the balloon relative to the artery varies considerably over the course of the heart's motion cycle, then the user may place the balloon such that its location relative to the lesion is correct at a specific phase of the cardiac cycle, and then inflate the balloon in synchronization to that phase. For some applications, such synchronized inflation is performed by means of apparatus for facilitating synchronized inflation described in WO 08/107,905 to Iddan, which is incorporated herein by reference.

For some applications, inflation is synchronized specifically to a selected phase in the subject's ECG signal. The ECG signal is typically received from an ECG monitor, or from a cardiac rhythm management (CRM) device, such as a pacer, or a defibrillator. For some applications, the processor identifies the selected phase of the ECG signal. Alternatively, the selected phase (e.g., the R wave of the ECG signal) is identified by the ECG monitor. Further alternatively, the selected phase (e.g., the R wave of the ECG signal) is identified by the CRM device.

For some applications, the aforementioned synchronization (and/or the synchronization of the actuation, deployment, and/or movement of other tools described herein) accounts for the delay in the generation of the ECG signal by the ECG monitor. For example, the delay may be determined in the following manner: A cardiac signal is generated by an electronic patient simulator. That signal is then fed as an input signal to the ECG monitor. The time difference between that input signal and the corresponding ECG signal produced by the ECG monitor is measured with an oscilloscope. If the delay D1 is measured in milliseconds and the heart rate (HR) is measured in beats per second, then, in order to actuate the tool in synchronization with a given phase of the ECG signal (e.g., the R-wave), a signal to actuate the tool is applied ((1000/HR)−D1) milliseconds after the given phase of the ECG cycle is detected.

For some applications, the value of HR as applied to the aforementioned synchronization is set according to the subject's most current heart rate. Alternatively, the value of HR is set according to the subject's average heart rate along a selected number of most recent cardiac cycles.

Figure 23A:
FIG. 23A shows a balloon being inflated inside a stent, there being overhanging regions at ends of the balloon that are inflated in synchronization with the subject's cardiac cycle, in accordance with some applications of the present invention.

Reference is now made to FIG. 23A, which shows an image of a balloon being inflated inside a stent. In FIG. 23A, edge lines have been added manually to the balloon, although, in accordance with some applications of the present invention, edge lines are added automatically. In the course of the deployment of certain tools within a vessel, a balloon is inflated within the tool, in order to expand the tool such that the tool comes into contact with an inner surface of the vessel. For example, a balloon may be inflated inside a stent such that the stent is brought into contact with an arterial wall. Alternatively, a balloon may be inflated inside a prosthetic valve, in order to deploy the valve adjacent to the remains of a natural valve. Further alternatively, a balloon may be inflated inside a graft, in order to deploy the graft.

Typically, the tool is shorter than the balloon, therefore, the balloon has overhanging portions at each end of the balloon. In such cases, one or both of the overhanging portions of the balloon typically initially expands before the remainder of the balloon expands. The overhanging portion becomes attached to the inner surface of the vessel, and, at that point, the longitudinal position of the balloon (and the tool) relative to the vessel typically becomes fixed, such that there is no longitudinal motion of the balloon relative the vessel. Subsequently, inflation pressure is further raised so that the tool itself attaches to the inner surface of the vessel.

For some applications, synchronization is applied such that the inflation is performed in a stepwise manner, in phase with a selected phase of the cardiac cycle, throughout the entire inflation procedure. Alternatively, synchronization is applied only during certain segment(s) of the inflation process, while inflation during earlier or later segment(s) of the process remains continuous.

For some applications, when deploying a tool (e.g., a stent) using the balloon, synchronization is applied in one or more steps to the inflation of one or more of the overhanging portions of the balloon, until the overhanging portion has become attached to the inner surface of the vessel and the longitudinal position of the balloon relative to the vessel has been fixed. Subsequently, the remainder of the inflation process, is continuous (and typically not synchronized) until the stent itself has become attached to the inner surface of the blood vessel.

Alternatively, inflation of the balloon is at first continuous until sufficient pressure has been applied to unfold the balloon. Subsequently, synchronization is applied in one or more steps to the inflation of one or more of the overhanging portions of the balloon, until the overhanging portion has become attached to the endoluminal wall and the longitudinal position of the balloon relative to the vessel has been fixed. Subsequently thereto, the remainder of the inflation process is continuous (and not synchronized) until the stent itself has become attached to the inner surface of the blood vessel.

For some applications, timing of the aforementioned one or more synchronized steps, relative to the detected desired phase in the vessel's motion cycle, takes into account parameters which affect the time delay D2 milliseconds between the activation of an inflation step by the aforementioned device for facilitating synchronized inflation and the corresponding increase in the diameter of the balloon and/or stent being inflated. For some applications, parameters that affect D2 include catheter parameters (e.g., length, inner diameter), balloon and tool (e.g., stent) parameters (e.g., length, diameter, nominal pressure), inflation fluid parameters (e.g., viscosity, relative portions of saline and contrast agent), or any combination thereof.

Typically, an additional parameter which affects the aforementioned time delay D2 is the amount of air trapped within the catheter carrying the balloon and/or stent. For some applications, activation of the apparatus for facilitating synchronized inflation is preceded by suction of trapped air out of the catheter. For example, such suction may be performed manually by the operator, such as by means of a syringe connected to the proximal end of the catheter. Alternatively, the suction may be performed by an electromechanical apparatus. For some applications, the electromechanical apparatus is coupled with the apparatus facilitating synchronized inflation.

For some applications, D2 is derived by measuring the time lag from (a) the moment a phase in the ECG signal (such as an R-wave) is sensed by the ECG device to (b) the moment a corresponding change in endoluminal pressure is sensed by a pressure sensor in the vicinity of the proximal end of the catheter. (For example, a pressure sensor 155 may be disposed between a valve 156 and a distal luer 154 of an accumulator-modulator 150, as described hereinbelow, with reference to FIGS. 39A-D.) Such a time lag is typically equal to the time it has taken the change in pressure to propagate back from the distal tip of the catheter to the proximal end of the catheter, the proximal end being connected to the apparatus facilitating synchronized inflation. D2 is typically proportional or generally equal to that lag, since D2 measures the delay associated with propagation of pressure over the same distance, in the opposite direction, i.e., from the proximal end of the catheter to its distal tip.

For some applications, delay D2 is measured in milliseconds, and the heart rate is measured in beats per second. In such cases, subsequent to detecting the desired phase of the subject's ECG (or other) signal, the actuation signal for actuating the tool is generated after $((1000/HR)-D2)$ milliseconds.

For some applications, in order to account for the aforementioned ECG-related delay D1 and inflation-related delay D2, and where the heart rate is calculated as HR beats per second, the actuation signal is delayed by $((1000/HR)-D1-D2)$ milliseconds, after detecting the desired phase of the subject's ECG signal.

For some applications, synchronization is applied to the deployment of a stent that is not balloon-inflatable but rather is self-expanding. For some applications, a delay of D3 milliseconds between the activation of the self-expansion mechanism and the stent actually expanding to the lumen's internal diameter is determined by means of ex-vivo experimentation with the stent. Alternatively or additionally, D3 is determined by means of performing measurements, under intra-procedural imaging, of in-vivo stent deployments.

For some applications, delay D3 is measured in milliseconds, and the heart rate is measured in beats per second. In such cases, subsequent to detecting the desired phase of the subject's ECG (or other) signal, the actuation signal for actuating the tool is generated after $((1000/HR)-D3)$ milliseconds.

For some applications, when accounting for the aforementioned ECG-related delay D1 and expansion-related delay D3, and where the heart rate is calculated as HR beats per second, the actuation signal is generated $((1000/HR)-D1-D3)$ milliseconds, after detecting the desired phase of the subject's ECG signal.

In further applications, the aforementioned synchronization is applied to the gated (for example, stepwise) motion and/or activation of a tool used for penetrating an occlusion within the vessel, and/or to a different tool.

Reference is now made to FIGS. 23B and 23C, which are schematic illustrations of apparatus for use with an inflation device 82, including a reusable portion 84, and a single-use portion 86, in accordance with some applications of the present invention. The reusable portion may be coupled and decoupled with respect to the single-use portion, as shown, respectively, in FIG. 23B and FIG. 23C. As described in WO 08/107,905 to Iddan, which is incorporated herein by reference, some portions of the apparatus for facilitating a synchronized inflation of a balloon and/or stent may be reusable, while other portions may be intended for single use. For some applications, the reusable portions are ones which do not come in contact, during the inflation process, with the inflation substance (such as a fluid), and the portions intended for single use are ones which come in contact, during the inflation process, with the inflation substance (such as a fluid). Alternatively or additionally, the reusable portions are ones which do not come in contact, during the inflation process, with the tool being inflated (such as a catheter carrying a balloon, a stent, and/or a valve), and the portions intended for single use are ones which come in contact, during the inflation process, with the tool being inflated (such as a catheter carrying a balloon, a stent, and/or a valve).

Reference is now made to FIGS. 39A-D, which are schematic illustrations of an extrabody accumulator-modulator 150 for facilitating the synchronized inflation of a balloon, in accordance with some applications of the present invention. A proximal luer 152 of the accumulator-modulator connects the accumulator-modulator to inflation device 82. A distal luer 154 of the accumulator-modulator connects the accumulator-modulator to the catheter 151 that supplies the balloon. Thus, the output of inflation device 82 (typically in the form of inflation fluid) supplies accumulator-modulator 150, and the output of accumulator-modulator 150 supplies the catheter. As described in US 2008/0221442 to Tolkowsky, which is incorporated herein by reference, synchronization of balloon inflation to the subject's cardiac cycle is typically facilitated by the accumulator-modulator. Accumulator-modulator 150 is generally similar to the accumulator-modulator described in US 2008/0221442 to Tolkowsky, except for the differences described herein.

Accumulator-modulator 150 facilitates intermittent balloon inflation that is performed in part, in a synchronized manner and in synchronization with the patient's ECG signal. The modulator part of the accumulator-modulator is typically responsible primarily for the synchronization of the inflation of the balloon to the ECG, or to a different physiological signal. For some applications, a processor determines that the physiological signal is at the suitable phase and sends a signal to the accumulator-modulator that actuates the balloon inflation. The accumulator portion of the accumulator-modulator facilitates a continuous build-up of the inflation pressure despite the inflation itself being in part intermittent, as described in US 2008/0221442 to Tolkowsky.

As described hereinabove, for some applications, a portion of the inflation process is continuous and a portion of the inflation process is synchronized. For example, inflation of the balloon may be synchronized only during the attachment of the overhanging portion of the balloon to the endoluminal wall, as described hereinabove. For such applications, the inflation fluid flows through the accumulator-modulator during the synchronized segment of the inflation process, however it bypasses the accumulator portion during one or more continuous segments of the inflation process, before and/or after the synchronized segment of the inflation process. Alternatively, the inflation fluid flows through the accumulator-modulator throughout the inflation process. However, the accumulator is prevented from accumulating fluid during one or more of the continuous phases of the inflation process.

A valve 156, controls the flow of inflation fluid through accumulator-modulator 150. For some applications, the valve is operated by a solenoid. Alternatively or additionally, other means are used for operating the solenoid. The flow of inflation fluid is in the direction of arrow 158 (shown in FIG. 39B). During continuous phases of the inflation process, valve 156 is open.

Figure 39B:
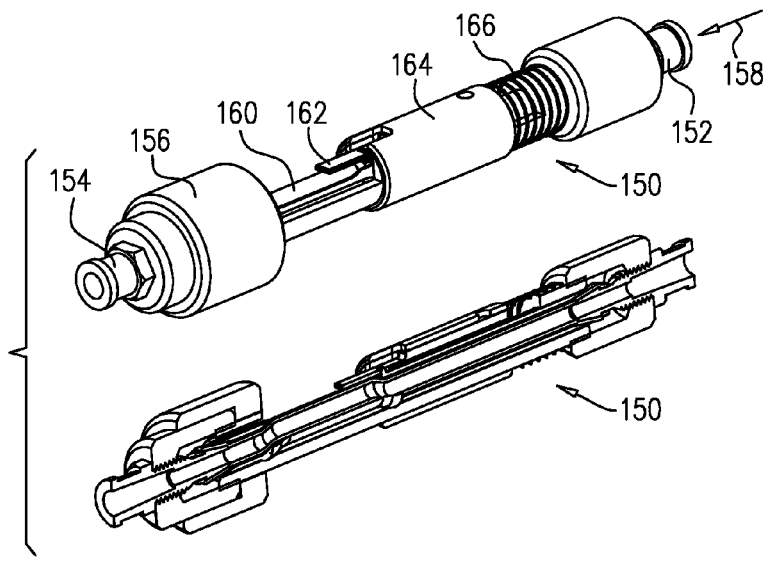

FIG. 39B shows a three-dimensional view, and a cross-sectional view of accumulator-modulator 150 during a preparatory phase of the inflation process, in which the apparatus is prepared for inflation of the balloon, in accordance with some applications of the present invention. Valve 156 is in an open position. Air is suctioned out of the catheter. Subsequently, elastic tube 160 of the accumulator-modulator and the catheter are filled (but, typically, not inflated or pressurized) with inflation fluid, during this phase. For some applications, during this phase, the balloon is filled with a small amount of inflation fluid, for example, in order to unfold folds in the balloon. All of the aforementioned preparatory steps are typical steps that are performed in preparation for balloon-inflation procedures, mutatis mutandis, even in the absence of accumulator-modulator 150. During the preparatory phase, a sliding portion 164 of the accumulator-modulator is locked by a lock 162 that prevents the sliding portion from advancing distally.

Typically, subsequent to the preparatory phase of the inflation process, the valve is closed, and inflation fluid continues to flow into the accumulator-modulator. Elastic tube 160 serves as an accumulator, in which inflation fluid is accumulated when the valve is closed. Typically, energy is accumulated in the elastic tube due to the accumulation of fluid in the elastic tube, and the resultant elastic deformation of the elastic tube. Subsequently, lock 162 is released after the accumulator has accumulated a sufficient amount of fluid (e.g., in response to such accumulation). For some applications, expansion of the elastic tube pushes the lock upwards, thereby snapping open the lock. The release of lock 162 releases sliding portion 164, and the sliding portion is advanced over the elastic tube by a spring 166. The advance of the sliding portion over the elastic tube is typically impeded by the accumulated fluid inside the elastic portion.

Figure 39C:
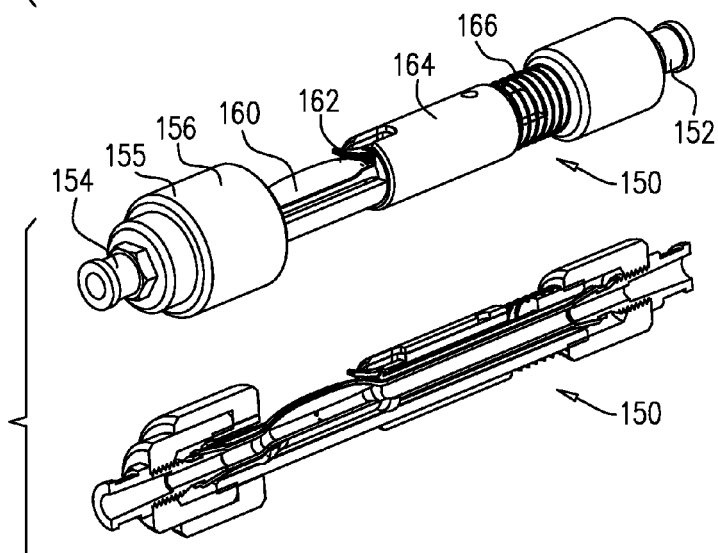

Subsequently, when a signal is received by the accumulator-modulator indicating that the subject's cardiac cycle is at a suitable phase for the overhanging portion to be attached to the endoluminal wall, valve 156 opens. For some applications, a processor determines that the subject's cardiac cycle is at the suitable phase (for example, in response to the subject's ECG signal), and sends a signal to the accumulator-modulator that actuates the opening of the valve. FIG. 39C shows the accumulator-modulator at this phase, i.e., the valve having been opened, the fluid having accumulated inside elastic tube 160, and with lock 162 having been released.

Figure 39D:
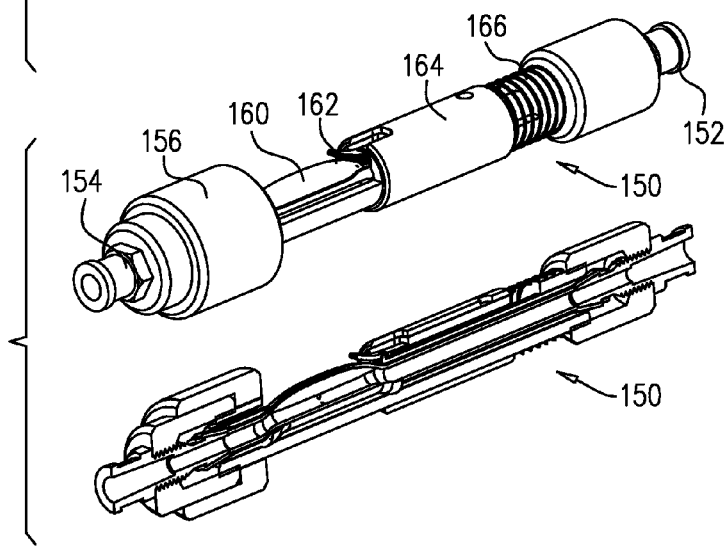

In response to the opening of the valve, the inflation fluid flows out of the distal end of the accumulator-modulator, into the catheter (and pressure in elastic tube 160 typically drops). The release of the fluid from the elastic tube allows the sliding portion to advance over the elastic tube. The advancement of the sliding portion over the elastic tube neutralizes the function of the elastic tube as an accumulator, since the sliding portion prevents the elastic tube from being able to expand. For some applications, the sliding portion assists the flow of fluid out of the accumulator. FIG. 39D shows the accumulator-modulator at this phase, the sliding portion having advanced over the elastic tube, thereby neutralizing the accumulator.

As described hereinabove, for some applications, inflation of the balloon subsequent to the inflation of the overhanging portion of the balloon is continuous, since the longitudinal position of the balloon relative to the vessel has been fixed. The function of the accumulator is typically neutralized during the continuous remainder of the inflation process. For some applications, neutralizing the accumulator function results in the continuous remainder of the inflation process being smoother and faster, compared to when the inflation fluid flows through an accumulator that has not been neutralized during this phase (e.g., compared to if the inflation fluid were to flow through elastic tube 160, with valve 156 open, but without the sliding portion constricting the elastic tube).

Typically, accumulator-modulator 150, shown in FIGS. 39A-D facilitates synchronized inflation of the balloon in a single step, i.e., by synchronizing inflation of the overhanging portions of the balloon with a given phase of a single cardiac cycle of the subject. For some applications, accumulator modulator facilitates synchronized inflation of the balloon over more than one cardiac cycle. For example, spring 166 may be replaced by a solenoid. Initially the accumulator-modulator acts generally in accordance with the technique described hereinabove. However, subsequent to the first phase of the synchronized inflation of the balloon, the solenoid moves the sliding portion proximally. Valve 156 is closed and fluid is accumulated in elastic tube. Typically, fluid is accumulated in the tube for a period of time that is greater than a single cardiac cycle (e.g., five or more cardiac cycles), in order to allow enough fluid to accumulate in the elastic tube to facilitate the next step of the synchronized inflation. Subsequent to the fluid accumulating in the elastic tube, the valve is opened and the solenoid slides the sliding portion distally, in synchronization with the given phase of the cardiac cycle. This procedure is repeated until the end of the synchronized inflation phase of the inflation process. After the final step of the synchronized inflation (i.e., at the commencement of the continuous inflation phase) the sliding portion remains in the distal position, thereby preventing the elastic tube from accumulating fluid.

The scope of the present invention includes using a different accumulator-modulator that functions only during a synchronized phase of the inflation process, but that is bypassed and/or neutralized during continuous phases of the inflation process that are before and/or after the synchronized phase. For example, an accumulator may be used that includes a piston and a spring that are disposed above a chamber. The upper surface of the chamber is a diaphragm, which functions in a manner generally similar to elastic tube 160, described with reference to FIGS. 39B-D (i.e., during a synchronized phase of the inflation process the diaphragm facilitates the accumulation of inflation fluid in the chamber, and an accumulation of energy, by the diaphragm being moved by the fluid). During the preparatory phase of the inflation process, a valve (that is generally similar to valve 156 described with reference to FIGS. 39B-D) is open and the fluid flows through the chamber and into the catheter, in a generally similar manner to that described hereinabove. At the initiation of the synchronized phase of the inflation, the valve is closed. The resulting accumulation of fluid in the chamber pushes the diaphragm upward, thereby pushing the piston upward against the resistance of the spring, and thereby accumulating energy in the spring. When a signal is received by the accumulator-modulator indicating that the subject's cardiac cycle is at a suitable phase for the overhanging portion to be attached to the endoluminal wall, the valve opens. The release of the fluid from the chamber, due to the opening of the valve, causes the spring to push the piston downward with force against the diaphragm. The piston includes a locking mechanism, such that in response to the piston being pushed downward with force, the piston becomes locked in a fixed position with respect to the diaphragm. The locked position of the piston is such that the diaphragm is unable to move upward. Thus, the piston inhibits the apparatus from acting as an accumulator.

For some applications, a diaphragm and piston that are generally similar to the diaphragm and piston described hereinabove are used. However, instead of the diaphragm and the piston moving upward in response to fluid flowing into the chamber, the diaphragm and piston are in upward positions with respect to the chamber from the outset of the inflation process. The spring is initially disposed in a preloaded position above the piston, the spring being constricted by the piston. The diaphragm, by virtue of being in the upward position with respect to the chamber (i.e., in a position that generally increases the volume of the chamber relative to a downward position of the diaphragm), facilitates an accumulation of inflation fluid into the chamber, when the valve is closed. When a signal is received by the accumulator-modulator indicating that the subject's cardiac cycle is at a suitable phase for the overhanging portion to be attached to the endoluminal wall, the valve opens. For some applications, the release of the fluid from the chamber, due to the opening of the valve, causes the spring to push the piston downward with force against the diaphragm. Alternatively, the spring is actuated to push the piston downward with force, but not necessarily due to the release of the fluid from the chamber. As described hereinabove, the piston includes a locking mechanism, such that in response to the piston being pushed downward with force, the piston becomes locked in a fixed position with respect to the diaphragm. The locked position of the piston is such that the diaphragm is locked in a downward position with respect to the chamber and is unable to move upward. Thus, the piston inhibits the apparatus from acting as an accumulator. For some applications, the chamber is bypassed during a continuous phase of the inflation, for example, in accordance with the techniques described hereinbelow.

Furthermore, the scope of the present invention includes using an accumulator-modulator that includes an accumulation-inhibiting functionality for different medical tools that function in both continuous and synchronized modes, the accumulation-inhibiting functionality being configured to inhibit accumulation of energy in the accumulator, during the functioning of the tool in the continuous mode.

Still furthermore, the scope of the present invention includes using an accumulation-bypass mechanism that bypasses an accumulation-facilitator during a continuous phase of tool actuation (e.g., balloon inflation). For example, apparatus that is generally similar to that described with reference to FIGS. 39B-D may be used. However, during the continuous inflation phase, instead of sliding portion 164 inhibiting accumulation of fluid in the elastic tube, fluid flow via the elastic tube is bypassed. For example, there may be a separate tube that provides fluid flow from inflation device 82 to catheter 151, without the fluid flowing through accumulator-modulator 150. A switch (e.g., an electronic and/or a mechanical switch) diverts the fluid, such that the fluid flows via the separate tube during one or more continuous phases of the inflation.

Enhancement of an Image

For some applications, the image of the tool within the stabilized image stream is enhanced in real time or near real time. For some applications enhancement of the image of the tool is performed in combination with the techniques described in WO 08/107,905 to Iddan, which is incorporated herein by reference.

For some applications, enhancement is performed automatically upon frames that have been image-tracked such that the tool is displayed in a same or similar relative location throughout most or all frames, as described hereinabove. For some applications, enhancement is performed by means of temporal filtering of the image-tracked frames. Typically, enhancement is performed in real time, or in near real time.

For some applications, the temporal filtering applies a weighted averaging function to the value of each pixel, as defined by its relative locations in a series of consecutive frames, and displays the resulting image. Alternatively or additionally, the temporal filtering applies a median function to the value of each pixel, as defined by its relative locations in a series of consecutive frames, and displays the resulting image. Further alternatively or additionally, the temporal filtering applies a mode function to the value of each pixel, as defined by its relative locations in a series of consecutive frames, and displays the resulting image.

For some applications, in addition to the application of a temporal filter, a spatial filter is applied to increase the contrast in the enhanced image. For example, the spatial filter may be a leveling filter. For some applications, contrast is increased by histogram stretching, and/or by gamma correction.

In accordance with respective applications, contrast enhancement is specifically applied to the edges of a tool, such as a balloon, or to the struts of a tool, such as a stent.

For some applications, only the final image, representing the outcome of the enhancement process, is displayed. Alternatively, intermediate frames, reflecting gradual enhancement, are also displayed on-line.

For some applications, enhancement is performed upon a number of typically-consecutive gated image frames. When using gated images, the enhancement is typically applied to fewer image frames than when the enhancement is applied to non-gated image frames, which may degrade the outcome of the enhancement process. However, such gated frames are often already aligned to a substantial extent, which may improve the outcome of the enhancement process.

For some applications, the enhancement is performed with respect to an image of an anatomical structure. For example, the anatomical structure may be a valve or a portion thereof, and/or a section of a vessel. For some applications, the structure is a lesion, which is typically visualized during contrast injection. For some applications, the lesion is identified by the user, for example, as part of the automated QVA process described hereinabove. For some applications, enhancement is applied, in particular, to the edges of the structure, which are made visible by means of contrast agent, or which are visible even without contrast agent due to a physiological phenomenon. For example, calcification is typically visible even without contrast agent.

For some applications, enhancement is performed utilizing only stabilized (e.g., image tracked, and/or gated) image frames. Alternatively, the enhancement utilizes non-stabilized image frames. For example, in the case of a calcified anatomical structure, such structure is typically more rigid than its environment and therefore motion during the cardiac cycle is typically reduced. Therefore, for some applications, non-stabilized images of the calcified structure are used for the enhancement.

For some applications, for the purpose of enhancing an anatomical structure, the shape and/or orientation of which structure varies during its motion cycle, some or all of the following steps are performed, typically on line:
  a. The anatomical structure in a selected image frame is identified, for example during angiography. For some applications, the identification is automatic (for example, the most significant occlusion along an imaged vessel is automatically identified). Alternatively, the identification of the feature is manual (for example, by the user clicking on the occlusion or in the vicinity of the occlusion in order to initiate the automated QVA disclosed hereinabove).
  b. The same anatomical feature is identified, typically automatically and typically by means of image processing, in additional image frames which are typically part of the same image sequence to which the frame in the preceding step belongs. For some applications, such means of image processing include pattern matching, and/or non-rigid object tracking techniques. For some applications, the image processing includes QVA techniques.
  c. Image frames are realigned, typically automatically, such that the orientation of the anatomical feature in at least most of them is similar.
  d. The aligned image frames are then displayed, typically automatically and according to techniques disclosed hereinabove, in the form of a stabilized image stream or an image stream that is both stabilized and enhanced.
  e. The shape of the aforementioned anatomical feature may vary over the organ's motion cycle. For example, in the area of the occlusion, an occluded vessel may be straight in some phases and twisted in others. For some applications, a baseline image frame is identified, in which the feature is in a shape that is designated as a baseline shape. The anatomical feature is identified in image frames in which the feature does not have the baseline shape, and, in such image frames, the feature is deformed, such that its shape becomes more similar to the baseline shape. The image frames in which the feature has been deformed are displayed in an image stream, together with the baseline image frame. Typically, this results in an image stream in which the shape of the feature is more similar along the image stream, than if the feature had not been deformed in some of the image frames. The deformation of the feature is typically performed automatically.

The deformation described in step (e) above typically facilitates the generation of an enhanced composite image, or enhanced image stream, which is of higher clarity (with respect to the anatomy of the feature) compared with the pre-deformation enhanced image or movie. For some applications, the visibility of the feature in an image stream is increased by deforming the feature as described above, but without applying other image enhancement techniques.

For some applications, one or more of the following steps are applied to an angiographic sequence of a vessel. The steps are typically performed automatically and on-line:
  a. A vessel segment having a given (typically distinctive) shape (e.g., a lesion, a bifurcation, etc.) is tracked such that an image stream or a composite image is stabilized with respect to the vessel segment;
  b. The tracked image stream or composite image is enhanced. Typically, the enhancement utilizes the alignment of the frames that results from the image-tracking, in accordance with the techniques described herein;
  c. The motion of a device relative to the vessel segment, throughout the motion cycle(s) of the vessel is analyzed. Typically, the device is disposed within the vessel segment. For example, the device may be a stent mounted on a balloon.

It is noted that for some applications, analysis of motion of the device relative to the vessel segment (i.e., step (c)) is performed on images of a vessel segment that have been tracked (i.e., step (a)), without the tracked images having been enhanced (i.e., step (b)).

(a) Tracking a Vessel Segment Having a Given Shape

For some applications, a region of interest (ROI) of an angiographic sequence is stabilized, and, optionally, enhanced. The enhancement is based on using imaging data from several frames in the sequence, rather than just a single frame. For some applications, imaging data from several frames in the sequence is used to (a) enhance the image, (b) enhance the resolution of the image, and/or (c) track the location of device markers relative to a lesion, thereby facilitating the correct deployment of the device, as described hereinabove with reference to FIG. 22B.

For some applications, the region of interest is selected by a user, for example, by the user clicking with a mouse on or near a vessel. In response to the input by the user, an ROI may be designated having a given size, and that is centered around the indicated region of interest. Alternatively, in response to the input by the user, the vessel boundaries of the vessel are automatically determined, and the ROI is defined based upon these vessel boundaries. Typically, the ROI corresponds to an area of interest for the physician, e.g., a lesion in the vessel. Further alternatively, the system automatically identifies markers of a device that is inside the vessel that is to be stabilized, in accordance with the techniques described herein. The ROI is defined based upon the location of the markers.

In order to use the data from several frames, the frames typically need to be registered to each other. An angiographic sequence is typically several seconds long. Therefore, during the acquisition time of the sequence, the vessel segment typically translates and rotates. The vessel further undergoes non-rigid mechanical deformation, e.g., due to the subject's respiratory and cardiac cycles. In addition, lesions in the vessel may have a different appearance throughout the cardiac cycle, which is particularly true for lesions that are not symmetrical (i.e., non-concentric) with respect to the center line of the vessel. Furthermore, due to the non-homogenous flow of the contrast material, portions of the vessel may appear differently in different frames, even along a short angiographic sequence.

For some applications, a processor includes a vessel-tracking functionality. A sequence of angiographic images is provided as input to the vessel-tracking functionality. In addition, an ROI in an image chosen from the sequence ('the baseline image') is provided as input to the vessel-tracking functionality. The ROI indicates the region of interest, and is typically defined in accordance with the techniques described hereinabove. The ROI is cropped from the baseline image to create a template (i.e., baseline) image of the ROI. Other images belonging to the sequence of images are matched to this template, in accordance with the techniques described hereinbelow.

The location of the template in each of the images in the sequence is typically established using the following two steps. First, a rough estimate of the location of the template is estimated. In this first step, it is assumed that the template merely undergoes a translation and rotation among images belonging to the same sequence. In a second step, once the system has compensated for this translation and rotation, it is assumed that the lesion underwent an additional non-rigid deformation, and this non-rigid deformation is determined by the system. The first and second steps are described hereinbelow, as rigid-tracking and non-rigid registration, respectively. The first and second steps are performed, respectively, by rigid-tracking functionality, and non-rigid deformation functionality of vessel-tracking functionality of the system.

Rigid-tracking functionality: In order to perform rigid-tracking on a given image of the sequence, the template and the image are provided as inputs to the rigid-tracking functionality. The rigid-tracking functionality locates the rotated and translated template in the image. This is accomplished by computing the gradients of the template image and of the given image, for example, by using the Sobel operator. Subsequently, the Normalized Cross-Correlation (NCC) between the gradients of the template and of the given image is calculated. The pixel location in which the NCC image attains its maximal value corresponds to the location in which there is the highest correlation to the template. Therefore, it is to this location that the rigid-tracking functionality determines that the template is most likely to have translated.

The template may have also rotated. Therefore, this computation of NCC is repeated for rotated versions of the template. This results in several NCC images, each corresponding to a different rotation of the template (e.g., rotations of 10 degrees, 20 degrees, 30 degrees, etc.). The maximal image value over all of these NCC images is determined by the rigid-tracking functionality to be the most likely rotation and translation of the template in the current image. For some applications, the estimated location and rotation is further refined by computing the NCC for a more refined set of angles. For example, having established that the maximal image value corresponds to a rotation of 20 degrees, NCC values may also be computed for rotations of 16 degrees, 18 degrees, 22 degrees, and 24 degrees, and the maximal image value over this refined range of angles may be determined.

Subsequent to the rigid-tracking functionality locating the template in the given image, the image is cropped, in a manner that accounts for the determined rotation of the template around the new estimated location of the template. This reduces the image to a smaller patch (i.e., a portion of the entire image). The rigid-tracking process is applied to all of the images in the angiographic sequence. Thus, the output of the rigid-tracking functionality is a sequence of cropped patches, each of the patches corresponding to the vessel segment in an image of the angiographic sequence.

Non-rigid registration functionality: The non-rigid registration functionality receives as an input the sequence of cropped patches that are outputted from the rigid-tracking functionality. Each of the patches is assumed to contain a mechanically-deformed version of the template. The non-rigid registration functionality accounts for these deformations. For each patch, the non-rigid registration functionality establishes the specific transformation which relates the patch to the template. Once this transformation is established, the processor reverses the deformation that the template has undergone in the specific patch. This may be regarded as unwarping of the patch. For some applications, unwarping is applied in accordance with the techniques described in the Kybic article cited hereinabove, which is incorporated herein by reference. Thus, the output of the non-rigid registration functionality is a set of unwarped patches, which coincide with the template.

Typically, the transformation is determined by determining which is the transformation that would result in the patch being most similar to the template, when the patch is unwarped according to the transformation. For some applications, in order to determine the transformation, a parametric form of possible transformations is designated by the system. The parametric form defines the possible transformations that the system analyzes. The system additionally designates one or more similarity criteria, which are the criteria that are used to measure the similarity between the unwarped patch and the template.

For some applications, similarity between the unwarped patch and the template is determined by determining the sum of absolute differences of the norm of the gradient images, or of the intensity images of the unwarped patch and the template. Alternatively or additionally, the similarity is determined by the correlation coefficient between the images, the mutual information between them, the correlation ratio, and/or the residual-complexity, for example, as described in the Myronenko article cited hereinabove, which is incorporated herein by reference.

For some applications, the form of the possible transformation is parameterized by an affine transformation. Alternatively, the form of possible transformations is parameterized by a mesh of control points over the images. The transformation of each pixel is given by interpolating the values at the control points. The interpolation is performed using B-spline or similar functions, for example, as described in the Rueckert article cited hereinabove, which is incorporated herein by reference.

An optimization process of the non-rigid registration functionality iteratively establishes the values of the control-points that maximize the similarity metric. For some applications, in order to account for large deformations, the optimization process is performed on a Gaussian pyramid of the registered images, in a coarse-to-fine approach.

For some applications, the non-rigid registration functionality determines the transformations of respective patches with respect to the template, by automatically extracting the vessel boundary points of the template and of the current patch. The non-rigid registration functionality determines the transformation that aligns these boundary points using an iterative process. For example, the non-rigid registration functionality may determine the transformation in accordance with the techniques described in the Chui article cited hereinabove, which is incorporated herein by reference.

The output of the non-rigid registration is a set of unwarped patches that match the template.

Patch-selection functionality: A patch-selection functionality of the processor selects which of the unwarped patches to use for further processing, as described hereinbelow. The correspondence of each of the unwarped patches to the template is ranked. For example, the ranking may be performed based on the similarity score between the unwarped patch and the template, which was already determined by the non-rigid tracking functionality. For some applications, patches are ranked in response to the phase of the cardiac cycle at which the image frames from which the patches were derived were acquired. For example, a patch that is derived from an image frame that was acquired at a phase of the cardiac cycle that is temporally closer to the phase of the cardiac cycle at which the baseline image frame was acquired, may be assigned a higher ranking than a patch that is derived from an image frame that was acquired at a phase of the cardiac cycle that is temporally further from the phase of the cardiac cycle at which the baseline image frame was acquired, ceteris paribus.

Alternatively or additionally, in order to perform the ranking of the unwarped patches, the boundaries of the vessel of the template and each of the unwarped patches are compared. It is to be expected that the boundaries of the unwarped patch and of the template should lie in close proximity to one another, and that the gradient at corresponding boundary locations of the unwarped patch should be approximately collinear with those of the template. For some applications, the vessel boundaries and the center line of the vessel in the template are determined, typically in accordance with the techniques described hereinabove. Similarly, the vessel boundaries and the center line of the vessel in the unwarped patch are determined, typically in accordance with the techniques described hereinabove. For some applications, since the template and the unwarped patch are expected to generally resemble each other, the vessel boundaries of the unwarped patch are determined based upon the center line of the template. Subsequent to determining the vessel boundaries and center lines of the template and of the unwarped patch, a measure is used to rank the proximity and co-linearity of the gradient at the vessel boundaries of the template and each of the unwarped patches. For some applications, a subset of the unwarped patches is selected according to this ranking. Alternatively or additionally, the patches are assigned respective weightings according to the ranking, as described hereinbelow.

(b) Enhancement of the Image Stream Using the Alignment Among Frames.

Enhancement-functionality: The template and a set of unwarped patches are typically provided as inputs to the enhancement-functionality of the system. For some applications, the enhancement functionality enhances the template image by generating a weighted-average of the unwarped patches. In accordance with respective applications, the weights are uniform, or patches with a higher similarity measure (as described hereinabove), or with higher rankings (as described hereinabove) are assigned correspondingly greater weightings. For some applications, the resolution of the template is enhanced by performing super-resolution, using the patches and the transformation corresponding to each one of them as inputs, for example, in accordance with the techniques described in the Farsiu article cited hereinabove, which is incorporated herein by reference.

Based upon the steps described until this stage, the output of the enhancement functionality is an enhanced version of the template image. For some applications, enhancement is applied to all of the patches that were output from the non-rigid tracking sub-module. All such patches generally correspond to the template. Therefore, at least some of the above steps are repeated for all of the remaining patches in the sequence.

Each of the patches is treated as the template, as described hereinabove. Typically, in the repeat steps, the rigid-tracking functionality is not applied to the image sequence. The non-rigid registration functionality is applied to the patches, but now with a different template. This produces a set of unwarped patches, now unwarped towards this new template. The patch-selection functionality is typically applied to the new set of unwarped patches in order to select a subset of these patches. Typically, the patch-selection functionality has already derived the center line of the first template. Therefore, for some applications, the patch-selection functionality does not necessarily derive the center lines of the subsequent templates. Rather, the patch-selection functionality determines the locations of the center lines of the subsequent templates based upon the center line of the first template, and the transformation between the first template and the current template.

Based on the outputs of the aforementioned functionalities, the new template is enhanced. This reiteration of the enhancement process over all of the patches produces a sequence of enhanced patches, corresponding to the original angiogram sequence. For some applications, a subset of patches is selected from the sequence and displayed, for example, based on the ranking of the similarity of the patches to the original template.

The image sequence that results from the raw angiographic sequence being stabilized or stabilized and enhanced is presented to the user (e.g., the physician).

(c) Analyzing and Depicting Relative Motion

For some applications, the motion of a device relative to the vessel segment, throughout the motion cycle(s) of the vessel is analyzed, as described hereinabove with reference to FIG. 22B. Typically, the device is disposed within the vessel segment. For example, the device may be a stent mounted on a balloon. For some applications, the motion of the device is depicted in an image stream or a composite image that is generated in accordance with the techniques described hereinabove, by virtue of the image stream or the composite image being stabilized with respect to the vessel segment. Alternatively, the system determines positions of the device at respective phases of the motion cycle of the organ and displays the positions on an image stream or on a composite image, in accordance with the techniques described hereinbelow. For some applications, the depiction of the motion of the device relative to the vessel segment leads to an estimation of potential risk of device malalignment upon its deployment, as described hereinabove, with reference to FIG. 22B.

Using the techniques described hereinabove, the transformation between a template that contains an anatomical feature (e.g., a lesion), to the other patches that contain the feature in the angiogram sequence is determined. Thus, every location in each patch can be mapped to the template. For some applications, a device is positioned at the vessel segment that defines the template. Markers of the device are located within the image, in accordance with the techniques described herein. The locations of the markers of the device in each patch in the sequence are mapped to their corresponding location in the template. For some applications, the template (or the enhanced template, or an enhanced or non-enhanced image stream) is displayed overlaid with a map that shows the locations of the device markers throughout the sequence, relative to the lesion. Thus, in a single image or in an image stream, the user receives an estimation of the locations of the markers, with respect to the lesion, throughout the entire sequence, or in a portion of the sequence.

For some applications, the system derives the locations of the markers over the course of the sequence, in accordance with the techniques described hereinabove. In response to deriving the locations of the markers with respect to the vessel, an output, for example, an alphanumeric or an audio output, is generated that indicates to the user the extent of the movement of the markers with respect to the vessel. For example, the output may include an indication of the total movement of the device relative to the vessel, an indication of the percentage of the frames in which the device is suitably positioned with respect to the vessel, or directions to the user to move the device by a given amount. For some applications, the output indicating the motion of the device relative to the vessel segment leads to an estimation of potential risk of device malalignment upon its deployment, as described hereinabove, with reference to FIG. 22B.

In accordance with respective applications, the motion of the device is depicted on a composite image that is generated from combining tracked image frames, an image stream that is generated from tracked image frames, a composite image that is generated from tracked and enhanced image frames, or an image stream that is generated from tracked and enhanced image frames. Furthermore, in accordance with respective applications, the locations of the markers (a) are determined by the system in accordance with the techniques described hereinabove and are then overlaid on the image(s), or (b) appear on the image(s) by virtue of tracking the image frames with respect to the anatomical feature and not with respect to the markers.

In the cases in which a device is located in the vicinity of the lesion, the markers of the device may interfere with the non-rigid registration process. It is assumed that the markers may move independently of the lesion due to the relative motion between the catheter carrying the device and the vessel. Therefore, for some applications, the system does not use the area that the markers enclose in the image during the non-rigid registration process. For such applications, before the registration is performed, the device markers are automatically located, for example, in accordance with the techniques described hereinabove.

For some applications, the markers are removed from the image by inpainting, the goal of the inpainting typically being to remove elements from the image, as naturally as possible (with as few visual artifacts as possible). For some applications, random values are assigned to the pixels inside the detected locations of the markers. For example, values of pixels from the immediate surroundings of the detected markers may be assigned to the pixels that correspond to the markers. Alternatively or additionally, techniques for inpainting may be applied as described in the Bartalmio article cited hereinabove, which is incorporated herein by reference. For some applications, during the non-rigid registration process, the system does not inpaint the markers, but rather the system disregards the area of the image that the markers enclose, during the non-rigid registration process.

For some applications, the enhancement of images of vessels facilitates the demonstration of such vessels not by pure contrast agent (as is typically done without applications of the current invention), but rather with a mixture of contrast agent with a dilutive agent such as saline. Using a lower total quantity of contrast agent typically reduces risks to the subject's health that may be associated with such an agent. For some applications, mixing of the contrast agent with the dilutive agent is performed by means of a faucet device to which reservoirs of the agents are connected.

For some applications, image enhancement is performed during the positioning of a tool, during the deployment of the tool, and/or upon the completion of the deployment of the tool. For example, an enhanced image or image stream may be used to evaluate whether a tool has been fully deployed.

For some applications, the edges of the enhanced tool are automatically emphasized. Alternatively or additionally, measurements of the enhanced tool are automatically generated and displayed. Such emphasis of edges and addition of measurements may be useful, for example, to evaluate whether the tool has been fully deployed.

For some applications, enhancement is generated from fluoro (i.e., low dose) images as opposed to cine (i.e., high dose) images, despite the typically-lower quality of such images in comparison to cine images. Alternatively, enhancement is generated from cine images.

For some applications, a sequence of endoluminal cross-sectional images generated by an imaging catheter along a vessel segment is displayed together (such as side-by-side) with the enhanced image of that segment and/or of a tool positioned (for example, a balloon) or deployed (for example, a stent) within that segment. For example, the imaging catheter may be an IVUS catheter, an OCT catheter, a NIRS catheter, and MRI catheter, or any combination thereof.

For some applications, extraluminal images of an anatomical structure (e.g., a luminal segment) are co-registered with endoluminal images of the structure. Typically, the outcome of such co-registration provides the operator with additional clinical information considered helpful with the procedure.

For some applications, one or more endoluminal images of a vessel segment are co-registered with the extraluminal image(s) of the vessel segment, for example, generally in accordance with the techniques described in US 2007/0038061 to Huennekens, which is incorporated herein by reference.

For some applications, co-registration is performed with respect to one or more anatomical features observable if both extraluminal images and endoluminal images. For example, the features may include a partial or total occlusion, an aneurism, a malformation, some other form of a lesion, a bifurcation, a curve, and/or a valve.

For some applications, co-registration is performed with respect to at least a portion of a luminal device observable in both the extraluminal images and the endoluminal images. For example, the portion of the device may include a proximal end of a deployed stent, a distal end of a deployed stent, a proximal end of a deployed graft, a distal end of a deployed graft, and/or a segment of a deployed valve.

For some applications, co-registration is performed with respect to a known distance along the lumen. For example, the co-registration may be performed by determining a pull-back or push-forward distance of an endoluminal imaging probe from a given location within the lumen. The distance along a longitudinal line of the lumen from the location is then determined in the extraluminal image. For example, the distance may be measured along a lumen center line of the extraluminal image that is generated in accordance with the techniques disclosed hereinabove.

For some applications, an extraluminal image steam that is co-registered with endoluminal images is stabilized. For example, the stabilization may be performed in accordance with the techniques described hereinabove, and/or techniques described in US 2008/0221442 to Tolkowsky, which is incorporated herein by reference. For some applications, the stabilized extraluminal image stream is also enhanced, for example, in accordance with the techniques described hereinabove.

For some applications, an endoluminal image steam that is co-registered with extraluminal images is stabilized. For example, the stabilization may be performed in accordance with the techniques described hereinabove, and/or techniques described in US 2008/0221442 to Tolkowsky, which is incorporated herein by reference. For some applications, the stabilized endoluminal image stream is also enhanced, for example, in accordance with the techniques described hereinabove.

Based upon the co-registration, the endoluminal image is typically displayed together (e.g., on the same or on separate displays) with the co-registered extraluminal image(s) comprising the coronary lesion.

Although techniques for co-registering extraluminal and extraluminal images to one another are described hereinabove primarily with respect to extraluminal fluoroscopic/angiographic images and endoluminal IVUS images, the scope of the present invention includes applying the techniques described herein to other forms of extraluminal and endoluminal images, mutatis mutandis. For example, the extraluminal images may include images generated by fluoroscopy, CT, MRI, ultrasound, PET, SPECT, other extraluminal imaging techniques, or any combination thereof. The endoluminal images may include images generated by optical coherence tomography (OCT), near-infrared Spectroscopy (NIRS), intravascular ultrasound (IVUS), magnetic resonance (MR), other endoluminal imaging techniques, or any combination thereof. Examples of the anatomical structure to which the aforementioned co-registration of extraluminal and endoluminal images may be applied include a coronary vessel, a coronary lesion, a vessel, a vascular lesion, a lumen, a luminal lesion, and/or a valve. It is noted that the scope of the present invention includes applying the techniques described herein to lumens of a subject's body other than blood vessels (for example, a lumen of the gastrointestinal or respiratory tract).

For some applications, enhancement is performed continuously and on-line in the form of a tracked and enhanced image stream. For example, such enhancement may be performed upon a determined number of recent frames, the determined number being set automatically by the system, or set and/or adjusted by the user.

For some applications, enhancement is performed by generating exponential moving average images. For some applications, enhancement is performed by averaging sets of two or more image frames that have been image tracked, in order to generate a plurality of averaged image frames. Thus, moving components in the image frames are, at least to some extent, averaged out, whereas components that appear to be stationary (e.g., the region of the image frames with respect to which the frames are tracked) remain. Subsequently, the averaged image frames are typically displayed as an image stream. For some applications, a moving-average image frame is generated, and an image frame (typically, the most recently acquired image frame) is averaged with the moving-average image frame, in order to generate a new moving-average image frame. Typically, the moving average image frame is an average (or a weighted average) of all of the previously acquired image frames of a given sequence. Alternatively, the moving average image frame is an average (or a weighted average) of a given number of most-recently acquired image frames. This process is repeated in order to generate further moving-average image frames. For some applications, the moving average image frame and the image frame that is averaged therewith, are assigned different weightings. Typically, successive moving-average image frames are displayed as an image stream.

For some applications, the aforementioned tracked and continuously-enhanced on-line image stream is displayed side by side with the native image stream, or the video-tracked image stream, or the gated image stream, or an image sequence of a typically-recent contrast injection, or a typically-recent static angiographic image frame, or a typically-recent static angiographic image frame with the markers or radiopaque segments of a tool displayed thereon, or any combination thereof.

For some applications, a mask is applied to the tracked and continuously-enhanced image stream such that the areas more remote from the tracked markers or radiopaque segments, which typically have greater motion, are blurred, hidden, or partially hidden. Typically, an image stream that is masked in this manner is easier for a user to observe.

Reference is now made to FIG. 24, which shows an enhanced image of an inflated coronary balloon, in accordance with some applications of the present invention. As shown, edges have been emphasized with a line and dimensions have been provided, in accordance with some applications of the present invention. Typically, the edges are emphasized, and/or the dimensions are provided, automatically.

Figure 25:
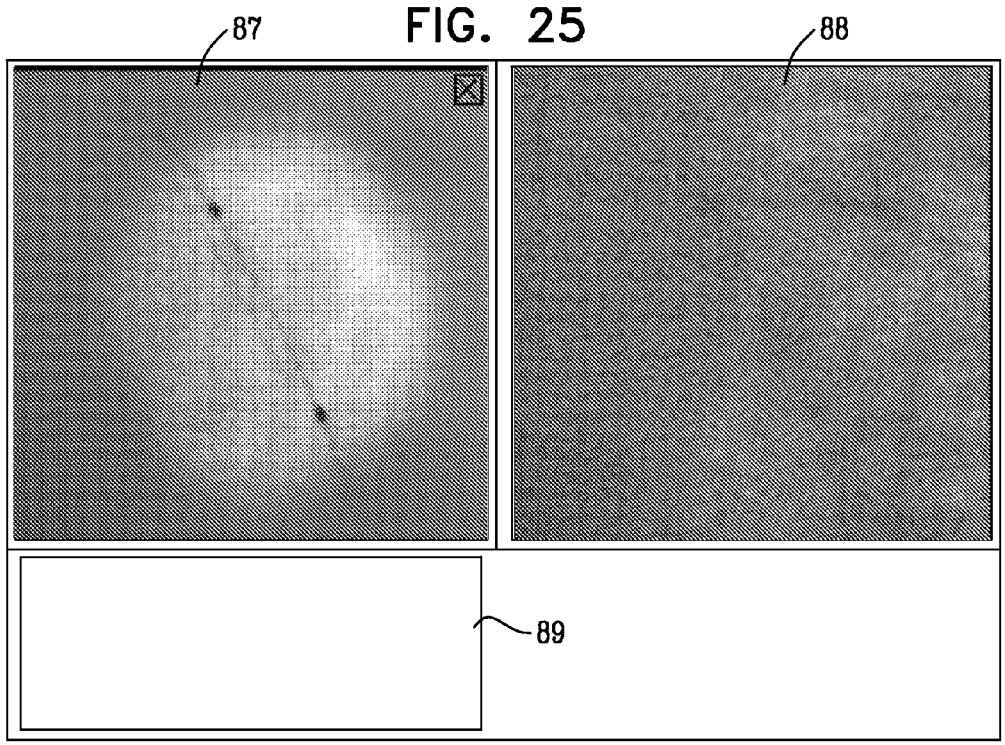
FIG. 25 shows an image of a deployed coronary stent that was automatically enhanced, alongside a raw image of the stent, in accordance with some applications of the present invention.

Reference is now made to FIG. 25, which shows an automatically-enhanced image frame 87 of a deployed coronary stent that was generated, in accordance with some applications of the present invention. The enhanced image was generated from fluoro (i.e., as opposed to cine) images, which typically renders such enhancement more difficult to perform. The enhanced image is shown alongside a native image frame 88 of the image stream from which the enhanced image was generated. For some applications, QVA measurements, and/or a QVA diagram are displayed on the screen, for example in a QVA box 89.

Figure 26:
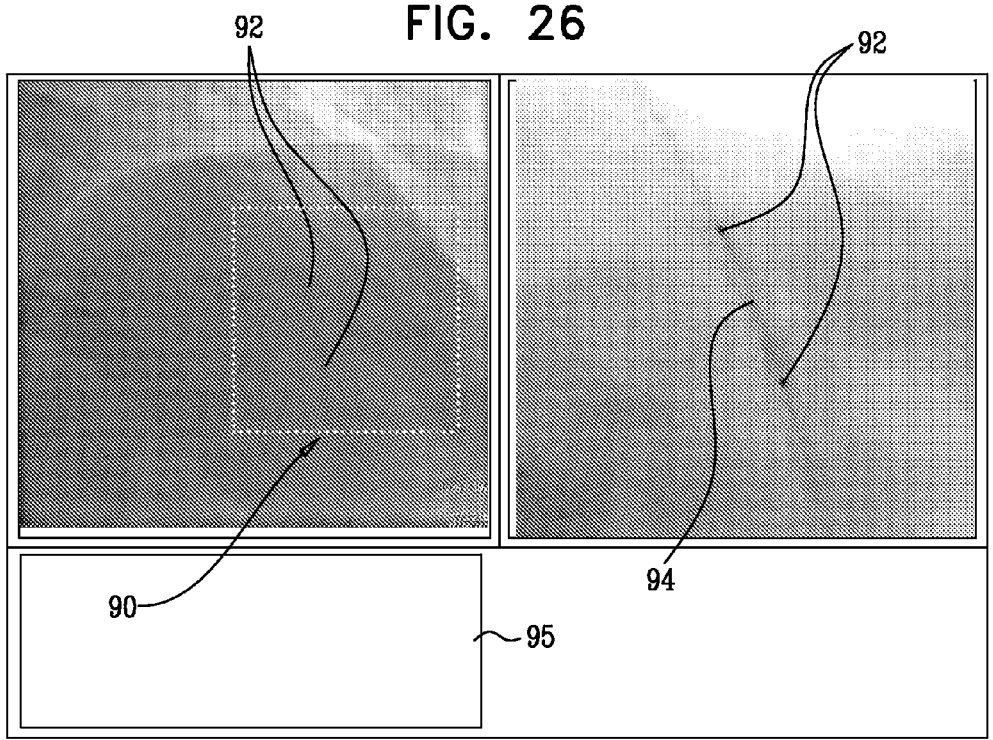
FIG. 26 shows an image stream that was tracked and enhanced, displayed side by side with a native image stream, in accordance with some applications of the present invention.

Reference is now made to FIG. 26, which shows a frame of a tracked and enhanced image stream (on the right) displayed side by side with a frame of the native image stream, in accordance with some applications of the present invention. An ROI 90 is indicated in the native image stream, within which a stent having markers 92 is located. For some applications, only the ROI is displayed in the tracked and enhanced image stream. It may be observed that in the tracked and enhanced image frame, markers 92 and struts 94 of the stent are more visible than in the native image frame. The struts are more visible due to the vicinity of the struts to the markers, the image frames having been tracked and enhanced with respect to the markers. For some applications, QVA measurements, and/or a QVA diagram are displayed on the screen, for example in a QVA box 95.

Figure 27:
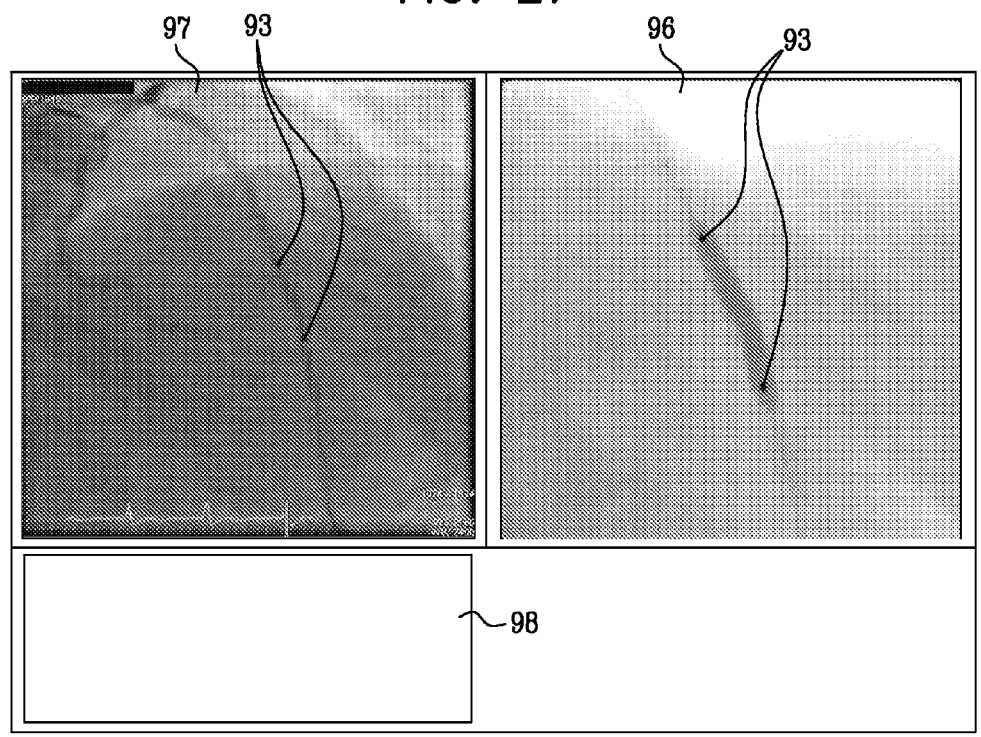
FIG. 27 shows an image stream that was tracked and enhanced, displayed side by side with a recent angiographic image frame, in accordance with some applications of the present invention.

Reference is now made to FIG. 27, which shows a frame 96 of a tracked and enhanced image stream (on the right) displayed side by side with a recent angiographic image frame 97, in accordance with some applications of the present invention. Markers 93 of an inflated balloon may be observed in both of the images. For some applications, QVA measurements, and/or a QVA diagram are displayed on the screen, for example in a QVA box 98.

For some applications, an image stream is enhanced with respect to a tool, such as an inflated balloon, or a deployed stent. An analysis similar to the QVA analysis, which was described hereinabove with respect to vessel edges, is performed and displayed for the edges of a boosted tool.

Additional Techniques for Image Improvement

Images of the heart and its vicinity often comprise additional elements that are not part of the heart itself and/or its vascular structure. Some of these elements are natural ones, such as the rib cage or spine. Some of these elements are artificial elements that were placed within the subject's body in the course of a previously-performed coronary bypass surgery, or that are currently placed on or within the subject's body. For example, the elements may include wires (e.g., CABG wires, or guide wires), electrodes, leads, and/or clips (e.g., CABG clips). Such elements typically appear within a fluoroscopic image as particularly dark (or particularly light in an inverted image).

Such elements, and in particular the latter, artificial ones, may increase the burden placed upon the physician observing the images, as they often divert the physician's visual attention from the heart and the vascular structure. Such diversion of attention may be caused by the additional elements moving at a different frequency and/or magnitude from the heart and its vasculature. In addition, such diversion of attention may be caused by the additional elements being of a different color or gray level from the heart and its vasculature.

For some applications, such additional elements are removed, in full or in part, from a stabilized (e.g., an image tracked) image stream. For example, such elements may be identified automatically, and the gray level of such elements may be changed such that they become more similar to the general background of the cardiac image. For some applications, such elements are identified and then removed from the stabilized image stream by means of a temporal or spatial filter, utilizing the fact that their motion may differ in time and/or relative location from the motion of the heart itself.

For some applications, elements are removed from the stabilized image stream, and the resulting gap is bridged by means of image processing. For example, bridging may be performed by means of gradually changing the gray level (or color) from its value at one side of the gap to its value at the other side of the gap.

For some applications, such elements automatically become less visible in the stabilized image stream, compared with their visibility in the native image stream. Typically this is because the images are not tracked with respect to such elements. Therefore, the relative position of such elements within the image frame typically changes in successive image-tracked image frames. For some applications, as described hereinabove, the image-tracked image frames are averaged, which typically further reduces the visibility of such elements.

For some applications, such elements are removed from the stabilized image stream by means of applying a mask, the mask having been derived from a road map that is generated automatically, as described hereinabove. For example, based upon the road map, a mask is applied to the image stream such that (a) the visibility of portions of the image stream that lie within the road map, and within a given distance from the road map, is not reduced, but (b) the visibility of other portions of the image stream is reduced.

In another example, based upon the road map, a mask is applied to the image stream such that (a) the visibility of portions of the image stream that lie within the road map have the smallest amount of reduction (if any), and (b) the visibility of other portions of the image stream is reduced, such that portions of the image stream further from the road map tend to be reduced more than portions of the image stream closer to the road map.

For some applications, a set of masks are generated, each of the masks corresponding to a respective phase of the cardiac cycle. When the image stream is displayed, masks are applied to image frames of the image stream in sequence, such that when an image frame showing blood vessels during a given phase of the cardiac cycle is displayed, the corresponding mask is applied to the image frame. Alternatively, a mask is generated corresponding to a given phase of the cardiac cycle. The image stream is gated to the same phase of the cardiac cycle, and the mask is applied to the gated image stream.

Example 1 of a Coronary Procedure

Figure 28:
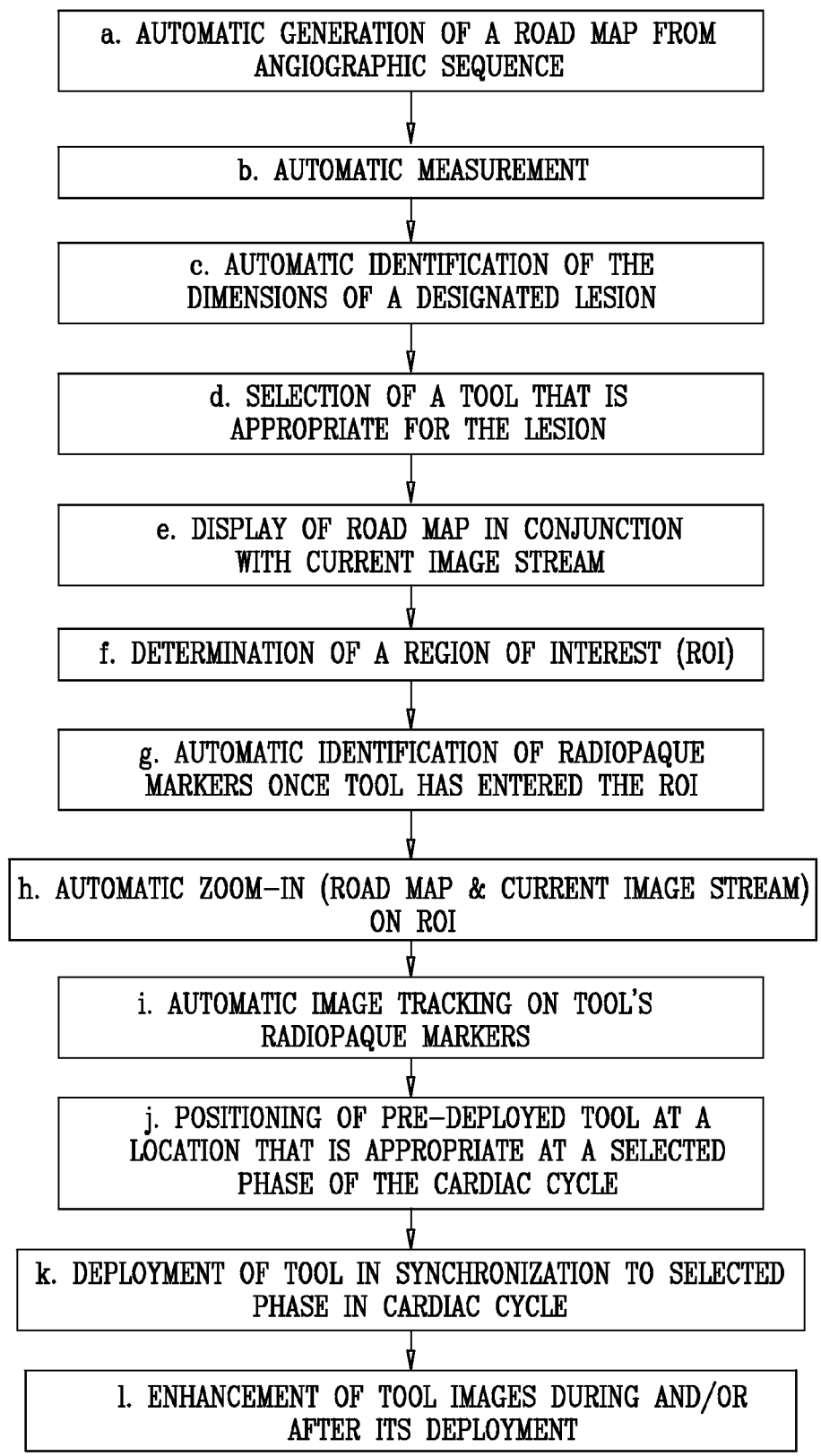
FIG. 28 is a flow chart of a sequence of steps, one or more of which may be performed in a coronary angioplasty procedure, in accordance with some applications of the present invention.

Reference is now made to FIG. 28, which is a flow chart of a sequence of steps, one or more of which may be performed in a coronary angioplasty procedure, in accordance with some applications of the present invention. For some applications, the steps of the procedure are not performed in the order in which they are shown in FIG. 28. Typically, the procedure includes one or more of the following steps:

a. During the diagnosis of the coronary tree by means of angiography, a road map is automatically generated upon each angiographic sequence.
b. For each road map, measurements are generated automatically or mostly automatically, typically relatively to some known reference dimension.
c. Lesion and/or artery dimensions, or distance indicators for such dimensions, are identified automatically or mostly automatically, typically relatively to some known reference dimension.
d. Tools (e.g., balloons and stents of specific dimensions) are selected based upon those measurements.
e. A road map is presented side-by-side with, and (optionally) is occasionally overlaid upon, the current fluoroscopic image stream. The fluoroscopic image stream may be native or stabilized.
f. An ROI is determined automatically or indicated by the user.
g. Once a tool has entered the ROI, its radiopaque segment(s)/markers(s) are automatically identified by the system. For some applications, the user clicks on the tool or in the vicinity of the tool, at which point automatic identification of the segment(s)/marker(s) commences. For some applications, in response to determining the position of the radiopaque segment(s)/markers(s), the shape of the road map is adjusted.
h. The fluoroscopic image stream and/or the road map is automatically zoomed into the ROI.
i. Image tracking commences automatically on the radiopaque tool segment(s)/markers(s). A tracked image stream is generated and displayed. Motion of the tool over the course of the heart's motion cycle, relative to the vessel and, specifically, relative to a designated lesion, is observed and (optionally) highlighted by graphical means.
j. The pre-deployed tool is positioned such that its location is appropriate, relative to the designated lesion, at a selected phase of the cardiac cycle.

k. Tool deployment is performed such that it is synchronized, during some or all of the deployment process, to the selected phase in the cardiac cycle.

l. Tool images are enhanced, both during the deployment and upon its completion, to assess the properness of the deployment. For some applications, such enhancement is performed and displayed continuously and on-line in the course of tool positioning, deployment and post-deployment. For some applications, image tracking, and/or image enhancement, before, during, and/or after the deployment of the tool is performed with respect to the lesion.

Example 2 of a Coronary Procedure

Figure 29:
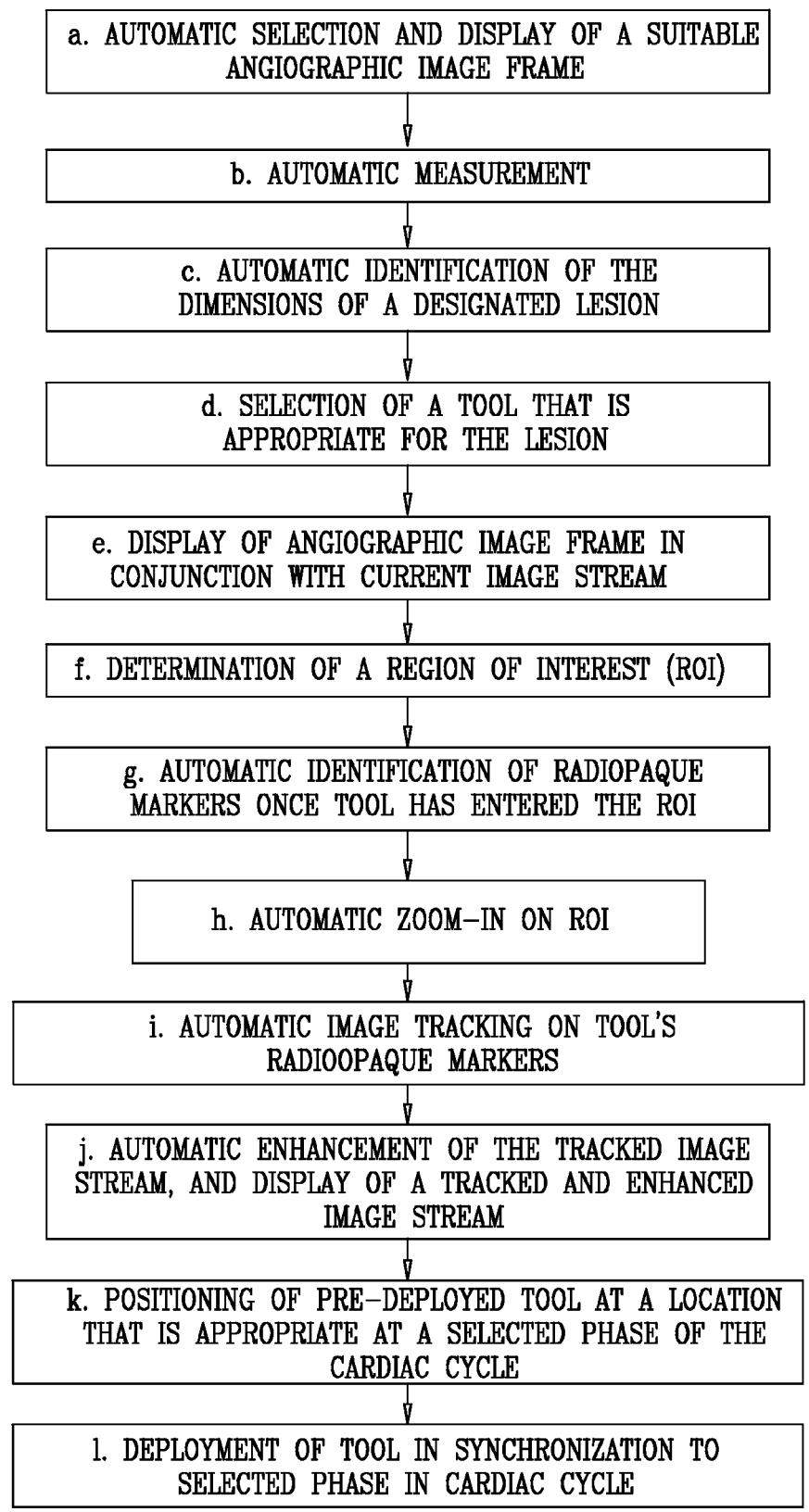
FIG. 29 is a flow chart of a sequence of steps, one or more of which may be performed in a coronary angioplasty procedure, in accordance with some applications of the present invention.

Reference is now made to FIG. 29, which is a flow chart of a sequence of steps, one or more of which may be performed in a coronary angioplasty procedure, in accordance with some applications of the present invention. For some applications, the steps of the procedure are not performed in the order in which they are shown in FIG. 29. Typically, the procedure includes one or more of the following steps:

a. During the diagnosis of the coronary tree by means of angiography, an angiographic image frame suitable for a road map is derived, typically automatically. For some applications, the sequence leading to such derivation is the one described with reference to steps 1 through 5 of FIG. 1. The derived angiographic image frame is displayed, typically without displaying a road map. Steps a and b of the present flow chart may be repeated for multiple viewing angles and/or different sections of the coronary tree.

b. For each derived angiographic image frame, measurements are generated automatically or mostly automatically, typically relatively to some known reference dimension.

c. Lesion and/or artery dimensions, or distance indicators for such dimensions, are identified automatically or mostly automatically, typically relatively to some known reference dimension.

d. Tools (e.g., balloons and stents of specific dimensions) are selected based upon those measurements.

e. A suitable angiographic image frame is presented side-by-side to the fluoroscopic image stream. The fluoroscopic image stream may be native or stabilized. The frames may be presented side-by-side in real time, near real time, or in reloop mode.

f. An ROI is determined automatically or indicated by the user in either the angiographic image frame, or, as is typically the case, in the current fluoroscopic image stream.

g. Once a tool has entered the ROI, its radiopaque segment(s)/markers(s) are automatically identified by the system. For some applications, the user clicks on the tool or in the vicinity of the tool, at which point automatic identification of the segment(s)/marker(s) commences.

h. The fluoroscopic image stream, and/or the angiographic image frame is automatically zoomed into the ROI, according to some predetermined zoom factor, or according to a zoom factor that is input by the user.

i. Image tracking of the fluoroscopic image stream commences automatically with respect to the radiopaque tool segment(s)/markers(s). A tracked image stream is generated and (optionally) displayed. Motion of the tool over the course of the heart's motion cycle, relative to the vessel and, specifically, relative to a designated lesion, may be observed and (optionally) highlighted by graphical means.

j. An image stream that is both tracked and enhanced is displayed. In accordance with respective applications, enhancement is performed with respect to a vessel highlighted by contrast agent, a balloon being inflated, a deployed stent, or any combination thereof.

k. The pre-deployed tool is positioned such that its location is appropriate, relative to the designated lesion, at a selected phase of the cardiac cycle.

l. Tool deployment is performed such that it is synchronized, during some or all of the deployment process, to the selected phase in the cardiac cycle.

Percutaneous Valve Replacement and/or Repair

Although some applications are described herein with respect to the diagnosis and treatment of the coronary arteries in the context of coronary angiography and/or angioplasty, the scope of the present invention includes applying the apparatus and methods described herein to other medical procedures. For example, the apparatus and methods described herein may be applied to percutaneous valvuloplasty, and/or replacement and/or repair of a valve (also known as percutaneous valve procedure), such as an aortic valve, a mitral valve, a pulmonary valve, or a tricuspid valve. For some applications, the percutaneous approach is transvascular (such as transfemoral). Alternatively, the percutaneous approach is via an incision (such as transapical). For some applications, using the techniques described herein facilitates accurate deployment of the valve, relative to the surrounding anatomy, even within a beating heart, or a moving vessel.

Figure 30:
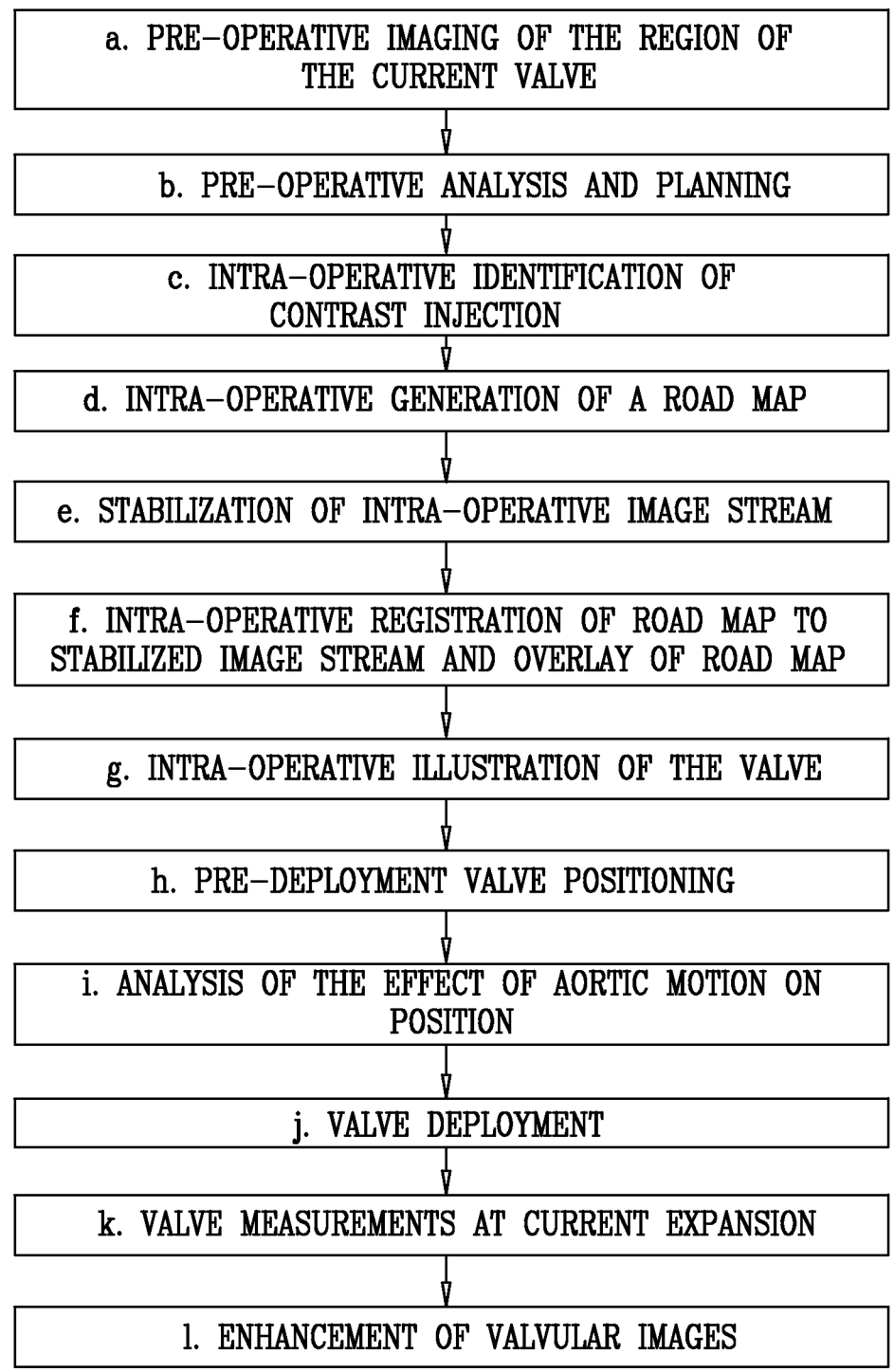
FIG. 30 is a flow chart of a sequence of steps of a percutaneous aortic valve replacement (PAVR) procedure, in accordance with some applications of the current invention.
Figure 31:
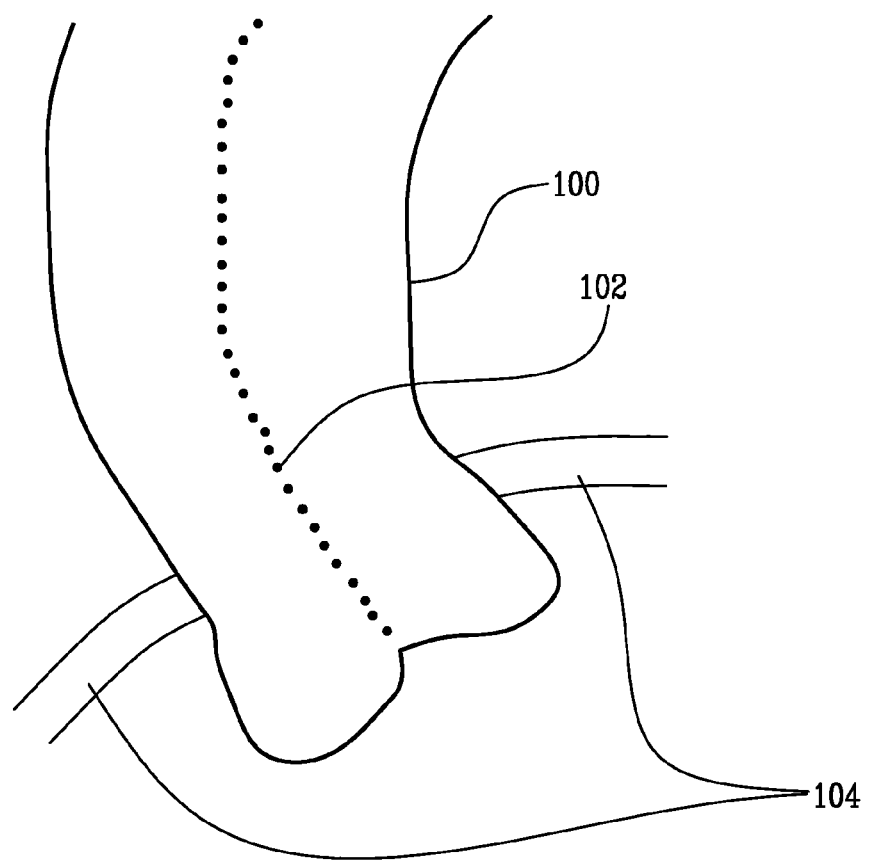
FIG. 31 shows a road map of the ascending aorta, in accordance with some applications of the present invention.
Figure 32:
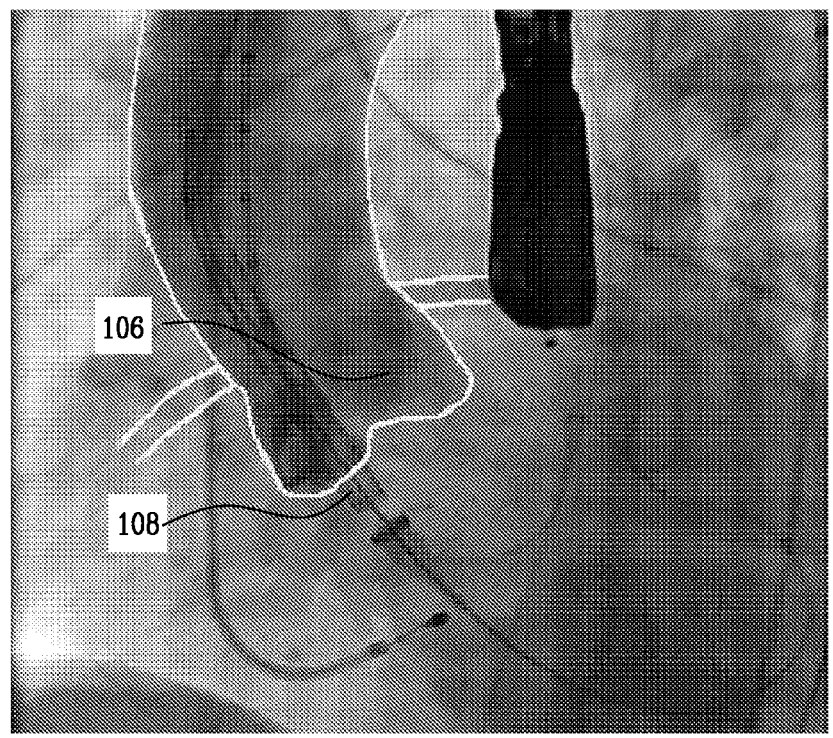
FIG. 32 shows the road map of the ascending aorta overlaid upon a fluoroscopic image stream of the corresponding anatomy, in accordance with some applications of the present invention.

Reference is now made to FIG. 30, which is a flow chart of a sequence of steps, one or more of which may be performed in a percutaneous valve procedure, in accordance with some applications of the present invention. For some applications, the steps of the procedure are not performed in the order in which they are shown in FIG. 30. The procedure is described herein using percutaneous aortic valve replacement (PAVR) as an example. However, the scope of the present invention includes applying the procedure described hereinbelow to any percutaneous valve procedure, applied to any valve, using any suitable equipment, and performed via any percutaneous access route. Typically, the procedure includes one or more of the following steps:

a. The region of the current valve (e.g., the native valve, or a previously-placed replacement valve) is imaged pre-operatively, such as by CT, ultrasound, or using a different imaging modality.

b. The pre-operative images are analyzed to determine the desired location, position and dimensions of the new aortic valve. For some applications, target lines pertaining to the desired location and/or angle of the positioned valve are added. Alternatively or additionally, virtual valves are deployed using some of the techniques described hereinabove. Optionally, such pre-operative images are later registered to, and displayed in conjunction with, the intra-operative image stream. For some applications, intra-operative images generated by rotational angiography or CT-like cross-sectional angiography, typically at the beginning of the procedure, are later registered to, and displayed in conjunction with, the intra-operative image stream.

c. An intra-operative injection of contrast agent under fluoroscopic imaging into the ascending aorta is detected, typically automatically, using the techniques described hereinabove. This step is typically performed on muld. Reference is now made to FIG. 31, which shows a road map of the ascending aorta 100, in accordance with some applications of the present invention. Typically, the road map is generated automatically, in accordance with the techniques described herein. Typically, one or multiple image frames of the contrast agent are utilized for generating a road map of the ascending aorta (or a portion thereof such as the lower portion adjacent to the location of the native valve), typically automatically, and typically on-line, using techniques described hereinabove. For some applications, the road map includes a center line 102 which may later be useful for leading the valve into position and/or placing the valve at a desired orientation relative to the native anatomy. Alternatively or additionally, the road map includes target lines pertaining to the desired location and/or angle of the valve after it will be positioned. Further alternatively or additionally, the road map includes segments 104 of the coronary arteries, which may later be useful for ensuring that the new valve is positioned so that it does not block any of the coronary arteries. For some applications, the road map also includes calcified portions of the anatomy (such as calcifications in the existing valve, in the aorta, in sections of the coronary arteries connecting to the aorta, or in other portions of the subject's body). Alternatively or additionally, the road map includes a radiopaque portion (such as a ring) of a previously-placed replacement valve which may later be used as a reference for positioning a new replacement valve.

e. Image tracking is applied to the intra-operative image stream, typically automatically. For example, one or more observable features are tracked, such as radiopaque segments or markers of the valve delivery device, of one or more sections of the valve itself which may be radiopaque by design or become radiopaque due to the presence of contrast agent within it, or one or more sections of a previously-placed replacement valve. For some applications, one of the techniques for image tracking and stabilization described hereinabove are applied to the PAVR procedure. Thus, for some applications, a stabilized image stream is displayed in real time or near real time. For some applications, the image stream that is displayed is gated to a selected phase in the cardiac cycle, and (optionally) gap filling among the gated image frames is applied.

f. The road map is registered, typically automatically, and typically on-line, to the fluoroscopic image stream of the corresponding anatomy. In accordance with respective applications, the road map is registered to the fluoroscopic image stream that has or has not been stabilized (for example, via image tracking) Typically, based on the registration of the road map to the fluoroscopic image stream the road map is overlaid on the fluoroscopic image stream. Further typically, fiducials are identified within the road map and within the fluoroscopic image stream, in order to facilitate the registration of the road map to the fluoroscopic image stream. For some applications, registration fiducials include the edges of the ascending aorta, the new valve's delivery mechanism, radiopaque sections of the new valve, calcified portions (which may typically be observed under fluoroscopy) of the original valve, a radiopaque portion (such as a ring) of a previously-placed replacement valve, and/or a radiopaque portion of a pigtail catheter. Reference is now made to FIG. 32, which shows a road map of the ascending aorta 106 overlaid upon a fluoroscopic image stream of the corresponding anatomy. For some applications, the observable feature(s) used for the aforementioned image tracking are not the same as the fiducial(s) used for the aforementioned registration of the road map to the image stream. For example, a valve or a valve delivery device 108 may be used for image tracking, while a pigtail catheter, which is generally stable relative to the aorta, may be used for the registration (including dynamic registration) of the road map.

Figure 33A:
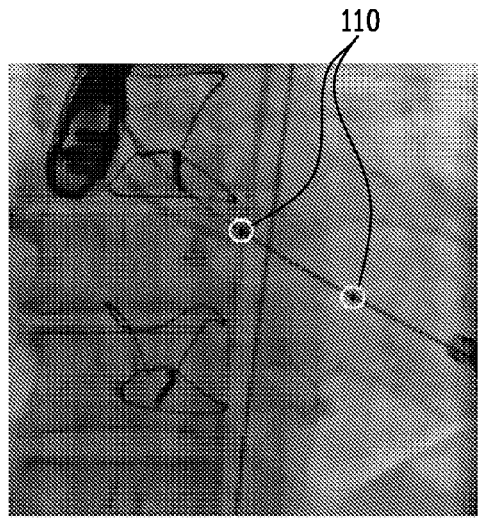
FIGS. 33A and 33B show radiopaque markers of a transapical valve delivery device and of a transfemoral pigtail catheter, which are automatically identified, in accordance with some applications of the present invention.
Figure 33B:
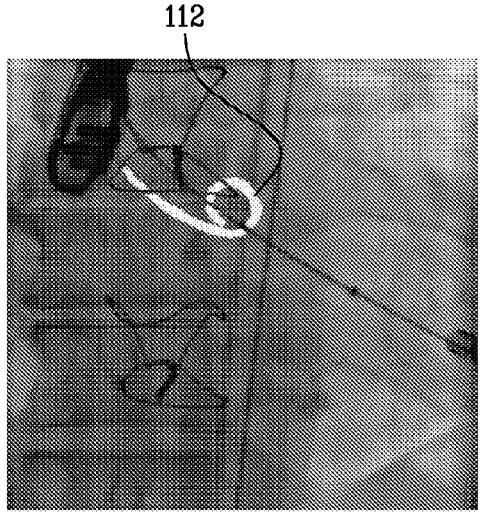

Reference is now made to FIG. 33A, which shows an image in which radiopaque markers 110 of a transapical valve delivery device have been identified for the purpose of image tracking. The markers are typically identified automatically, as described hereinabove. The markers are highlighted in the image. Reference is also made to FIG. 33B, which shows an image in which a transfemoral pigtail catheter 112 has been identified for the purpose of registering the image to a road map. The pigtail catheter is typically identified automatically, using techniques similar to those described hereinabove (e.g., using pattern matching). The catheter is highlighted in the image.

For some applications, the aforementioned valve and the aforementioned pigtail catheter are inserted via similar routes of access (such as transfemoral). Alternatively, the valve and the pigtail catheter are inserted via different routes of access (for example, the valve may be inserted transapically, while the pigtail catheter is inserted transfemorally).

g. For some applications (for example, if the valve itself is not sufficiently radiopaque to be clearly visible in the fluoroscopic image stream), a graphic of a valve is generated, based on a known geometrical location of the valve relative to the radiopaque valve delivery device, or to a feature (e.g., a stent) to which the valve is fixed. Typically, most of the replacement valve is illustrated graphically. However, for some applications, only the distal edge of the valve is graphically illustrated, but the remainder of the valve is imaged.

Figure 34:
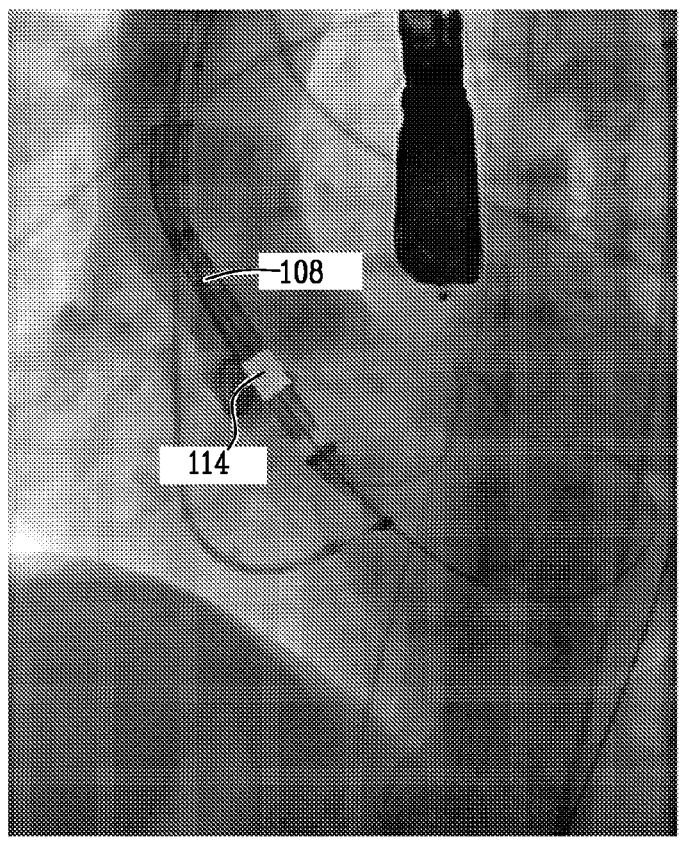
FIG. 34 shows a valve, which is graphically illustrated based on its known location relative to a radiopaque valve delivery device, in accordance with some applications of the present invention.
Figure 35:
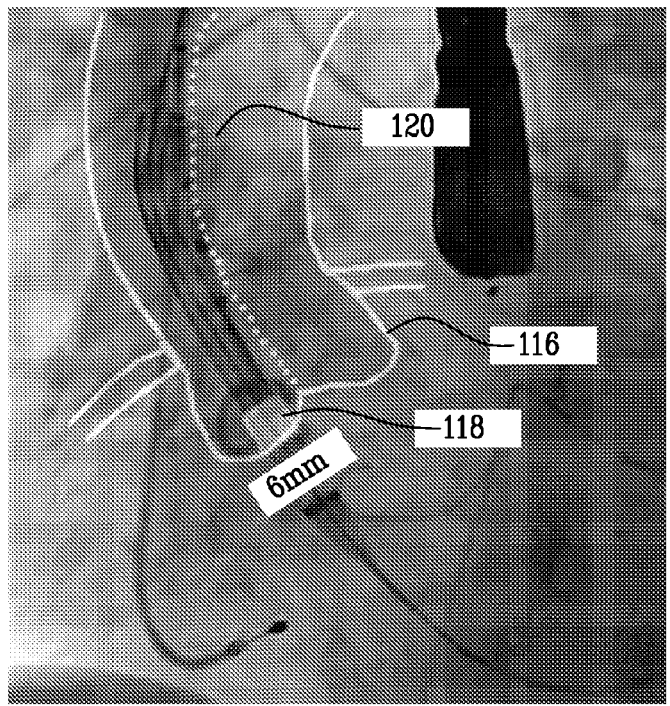
FIG. 35 shows an image of a pre-deployed graphically illustrated valve positioned upon a stabilized image stream on which a road map has been overlaid, in accordance with some applications of the present invention.

Reference is now made to FIG. 34, which shows a valve 114 that has been graphically illustrated. Typically, the valve is graphically illustrated based on its known relative location to radiopaque valve delivery device 108.

h. The valve delivery device is positioned, optionally using the road map, such that the location of the pre-deployed valve (or of the aforementioned illustrated valve) in the typically stabilized image stream is appropriate, relative to an implantation location of the valve. For example, a line marking the distal edge (or any other known section) of the new valve may be guided toward a target line in the road map till the two significantly overlap. Alternatively or additionally, a line marking the longitudinal orientation of the new valve is guided toward a longitudinal target line in the road map till the two significantly overlap. Reference is now made to FIG. 35, which shows a pre-deployed graphically illustrated valve 118 positioned upon a stabilized image stream of the aorta 120 on which a road map 116 has been overlaid.

i. In the prior art, certain replacement valves are typically deployed under rapid pacing in order to momentarily neutralize the aortic blood flow (which is typically very forceful). For some applications, techniques are provided to account for cases of "valve shift," i.e., cases in which once rapid pacing is stopped and the forceful flow of blood along the aorta resumes, the implanted valve shifts distally relative to its original position of deployment. For example, the valve may shift due to a "sail in the wind" effect of the blood flow on the valve. Thus, for some applications, the positions of the pre-deployed valve are determined at different phases in the cardiac cycle, such as systole and diastole, during the subject's normal heart beat, and not during rapid pacing. Determination of the valve's positions is typically facilitated by observing an image stream that has been stabilized by means of image-tracking the pre-deployed valve, according to techniques described hereinabove. For some applications, it is determined that the pre-deployed valve shifts by a distance D mm along the vessel over the course of the cardiac cycle. Therefore, the valve is aimed and deployed at a distance from its designated implantation location in the ascending aorta that is determined based upon the observed shift of the valve of D mm. For example, the valve may be deployed at the distance of D mm from its designated implantation location. For some applications, the non-deployed valve shifts by a smaller distance than the deployed valve, due to blood flow having a greater sail in the wind effect on the deployed valve than the non-deployed valve. Therefore, the valve is deployed at a distance that is greater than D mm from its designated implantation location. Alternatively, the non-deployed valve shifts by a greater distance than the deployed valve, for example, due to greater resistance of the vessel walls on the deployed valve than on the non-deployed valve. Therefore, the valve is deployed at a distance that is less than D mm from its designated implantation location.

Typically, the final position of the deployed valve, after rapid pacing has been stopped and "valve shift" has occurred, is closer to the designated implantation location of the valve compared with deployment of the valve when the shift of the valve is not measured and accounted for, ceteris paribus. Furthermore, accurate determination of the valve shift is typically facilitated by the use of a stabilized image stream for determining the shift of the pre-deployed valve over the course of the subject's cardiac cycle. For example, an image stream may be stabilized by image tracking the image stream with respect to the valve delivery device, the pigtail catheter, and/or a portion of the subject's anatomy that is visible even in the absence of contrast agent (e.g., calcification around the native valve). The valve shift is determined by observing the shift of the valve relative to the vessel in which it is to be deployed, using the image tracked image stream.

Figure 36:
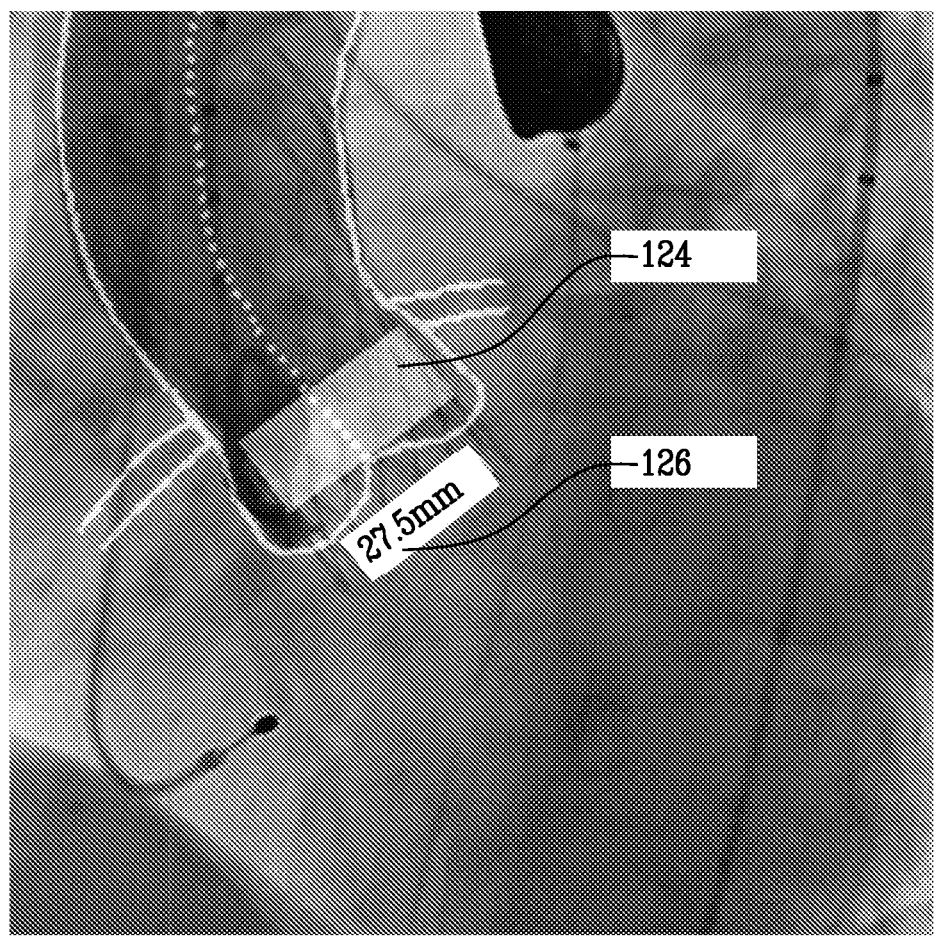
FIG. 36 shows a graphically illustrated expanded valve deployed within the ascending aorta, in accordance with some applications of the present invention.

For some applications, similar techniques to those described with respect to valve shift are applied to account for similar shifting of other tools, such as a stent, or a graft.

j. The valve is deployed. Optionally, deployment is synchronized, in one or more steps, to a selected phase in the cardiac cycle. For some applications, synchronization is performed by a synchronizing device that is connected to the valve delivery device and times its actuation in a gated (e.g., stepwise) manner to a selected phase in the cardiac cycle. For some applications, the synchronization reduces or eliminates the need for rapid pacing during a deployment of a valve that otherwise would have required such pacing. For some applications, deployment of the valve is synchronized to the same phase with respect to which the stabilized intra-operative image stream is gated. For some applications, the synchronization is also applied to a preceding pre-dilatation step, in which the original valve is dilated, such as by means of a balloon, in order to overcome typically-rigid calcified sections and create a space into which to place the new valve. Reference is now made to FIG. 36, which shows a graphically-generated image 124 of a valve being deployed within the ascending aorta. The current outer diameter 126 of the valve is displayed on the image, in accordance with some applications of the present invention.

For some applications, the original (i.e., native) valve is not replaced but rather it is repaired. For example, such repair may include the further coupling, such as via suturing or clipping, of leaves of the native valve to one another. For some applications, pertaining to valve repair (such as mitral valve repair), synchronization is applied to suturing and/or clipping of the cyclically-moving leaflets of the valve. Typically, the synchronization of these procedures facilitates the performance of these procedures because the leaflets shift rapidly back and forth (typically, according to the heart beat). Typically, the synchronization is such that the joining tool is actuated at the phase of the cardiac cycle during which the leaves are closest to one another.

Figure 37A:
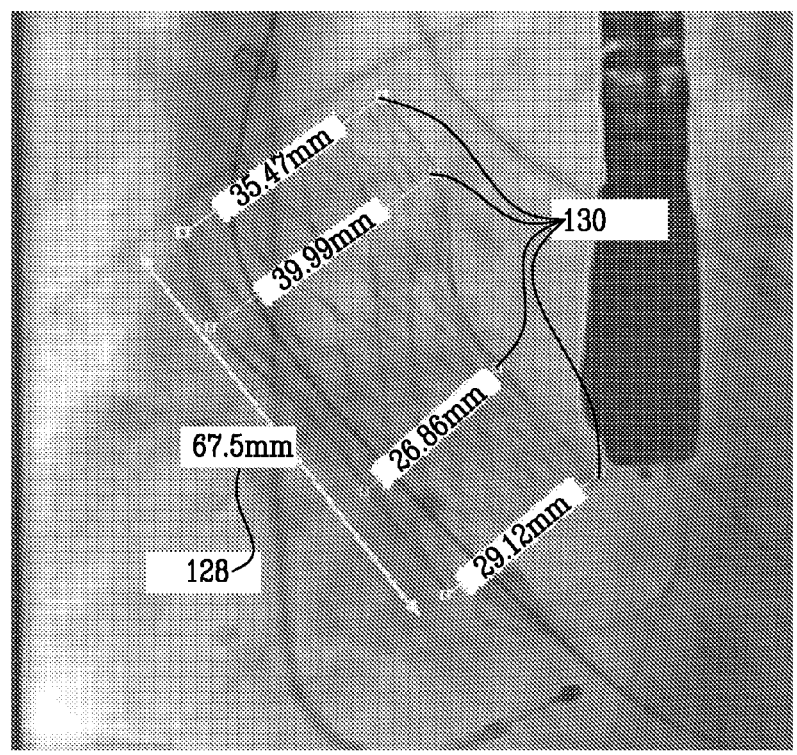
FIGS. 37A and 37B show measurements performed upon a valve deployed in the ascending aorta, in accordance with some applications of the present invention.
Figure 37B:
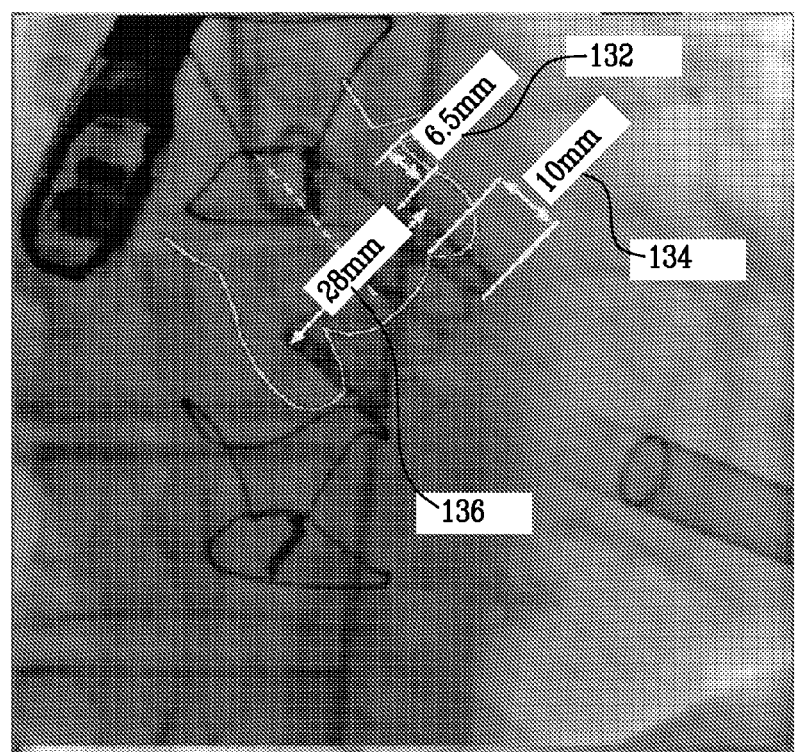

For some applications, synchronization is applied to the deployment of a stent-less valve (i.e., a prosthetic valve typically lacking any rigid supporting structure, such as the Direct Flow valve), which is deployed by being inflated at its designated implantation location. Typically, synchronization is applied to the inflation of sections of the structure of the new valve.

k. At any phase along the process and for any road map, measurements may be generated, automatically or mostly automatically, using techniques described hereinabove. Typically, measurements are performed relative to some known reference dimension such as the diameter of the valve delivery device or the distance between radiopaque elements of the valve itself. For some applications, the measurements include the current size (such as length and/or outer diameter) of the valve while it is being expanded in position, the diameter of the aorta, the space available for deployment of the replacement valve, the distance between the original valve and the aortic ostia of the coronary arteries, the distance between the replacement valve and the aortic ostia of the coronary arteries, the distance between the lower edge of the replacement valve and the aortic annular line, the inner diameter of the replacement valve, the outer diameter of the replacement valve, or any combination thereof. For some applications, measurements are displayed in conjunction with the road map, and/or a fluoroscopic image of the valve. Reference is now made to FIG. 37A which shows, displayed on a fluoroscopic image of a valve deployed in the ascending aorta, measurements of a current length 128, and current outer diameters 130 of respective portions of a valve. Reference is also made to FIG. 37B, which shows, displayed on a fluoroscopic image of a valve deployed in the ascending aorta, measurements of (a) a distance 132 of the valve to the coronary ostium, (b) a distance 134 of the valve to the annular line, and (c) a current outer diameter 136 of the valve.

l. Tool images are enhanced using some of the techniques described hereinabove, both during the deployment, and upon its completion, to assess the properness of the deployment. For some applications, such enhancement is performed and displayed continuously and on-line in the course of valve positioning, deployment and post-deployment.

As used hereinabove, the term "valve delivery device" refers both to insertion elements that are retrieved subsequent to valve deployment, and to fixation elements (such as a stent-like feature) that remain inside the aorta together with the new valve.

Examples of Additional Medical Procedures

Although many of the applications of the present invention are described with reference to the diagnosis and treatment of the coronary arteries in the context of coronary angiography and/or angioplasty, the scope of the present invention includes applying the apparatus and methods described herein to other medical interventions. The scope of the present invention includes applying the techniques described herein to any bodily lumen or cavity on which diagnosis and/or treatment may be performed, including but not limited to the vascular system, the heart's chambers, the bronchial tract, the gastro-intestinal tract, or any combination thereof, and using any form of imaging and any applicable medical tool. For example, the techniques described hereinabove can be applied to any of the following additional procedures, or to any combination thereof (For some applications, the techniques described hereinabove are applied to the following procedures in combination with techniques described in WO 08/107,905 to Iddan, which is incorporated herein by reference.)

- Percutaneous placement, replacement or repair of a valve as disclosed hereinabove. It is noted that the applications described herein pertaining to the suturing of a valve include the suturing of a native or a replacement valve to a lumen of the subject's body, and/or the suturing of leaflets of a valve to each other.
- Catheterization of pulmonary arteries, applying the tools and techniques (e.g., guide wire, balloon, stent, occlusion-opening tools) previously described in the context of the coronary arteries. For some applications, such a procedure is performed in conjunction with stabilized imaging as described hereinabove. For example, an image stream of the procedure is stabilized by means of image tracking the observable feature(s) of one or more tools applied in the course of the procedure, in accordance with the techniques described hereinabove. For some applications, the image stream is stabilized with respect to a given phase of the cardiac cycle. Alternatively or additionally, the procedure is performed in synchronization with the cardiac cycle, so as to achieve improved deployment of a balloon or a stent, or better penetration of an occlusion. Typically, the phase during which a tool is deployed is the same as the phase at which the pre-deployed tool has been observed to be properly positioned in the stabilized image stream.
- Closure of holes in the septal wall, such as in the treatment of patent foramen ovale (PFO), ventricular septal defect (VSD) and atrial septal defect (ASD), within the cyclically-moving heart. In accordance with techniques described herein, a carrier carrying a closure tool is led to, and positioned at, a desired anatomical location (such as the site of the hole in the septum) while both the carrier and the heart anatomy are viewed in an image stream that is typically stabilized. For some applications, the image stream is stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the closure tool is deployed at the desired anatomical location at a given phase of the cardiac cycle. (Deployment of the tool includes its positioning, assembly, expansion, and/or release from the carrier.) The phase during which the tool is deployed is typically the same as the phase at which the pre-deployed tool has been observed to be properly positioned in the stabilized image stream. For some applications, the closure tool is deployed by expanding the closure tool at the given phase during a single cycle. Alternatively, the closure tool is deployed by expanding the closure tool in a stepwise manner, at the selected phase, during more than one cycle.
- Placement of a stent graft within the cyclically-moving aorta to treat abdominal aortic aneurysms. In accordance with techniques described herein, a carrier carrying a stent graft is led to, and positioned at, a desired anatomical location (such as the site of the aneurysm) while both carrier and aortic anatomy are viewed in an image stream that is typically stabilized. For some applications, the image stream is stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the stent graft is deployed at the desired anatomical location at a given phase of the cardiac cycle. (Deployment of the stent graft includes its assembly, expansion and/or release from the carrier.) The phase during which the tool is deployed is typically the same as the phase at which the pre-deployed tool has been observed to be properly positioned in the stabilized image stream. For some applications, the graft is deployed at the desired anatomical location at a given phase of the cardiac cycle (such as when the corresponding section of the target vessel is at its peak dimensions), without observing stabilized images. For some applications, the stent is a self-expansible stent.
- Trans-catheter placement of a bypass graft to a cyclically-moving vessel. In accordance with techniques described herein, a catheter carrying a bypass graft (or any other form of a bypass) is led to, and positioned at, a desired anatomical location (such as proximally to the site of a total occlusion) while both carrier and occlusion are viewed in an image stream that is typically stabilized with respect to a given phase of the cardiac cycle. Alternatively or additionally, the image stream is stabilized by means of image tracking the observable feature(s) of one or more tools applied in the course of the procedure, in accordance with the techniques described hereinabove. Subsequently, the bypass graft is deployed at the desired anatomical location at a given phase of the cardiac cycle, the deployment typically including departure from the native vessel proximally to the site of the occlusion and re-entry to the native vessel distally to the site of the occlusion. (Deployment of the graft includes its assembly, expansion and/or release from the carrier.) The phase during which the graft is deployed is typically the same as the phase at which the pre-deployed graft has been observed to be properly positioned in the stabilized image stream. For some applications, the graft is deployed at the desired anatomical location at a given phase of the cardiac cycle (such as when the corresponding section of the target vessel is at its peak dimensions), without observing stabilized images.

Localized energy application to a tissue, such as within the heart (e.g., cardiac ablation performed by means of radio frequency ablation, cryoablation, laser, electrocautery, or ultrasound, to treat cardiac arrhythmia). For some applications, the present invention facilitates the ablation of endocardial tissue in a desired pattern, such as a continuous line or a series of lines, for example, to apply a Maze procedure to the tissue. For some applications, movement of the ablation tool is performed in synchronization with a given phase in the cardiac cycle. Alternatively or additionally, delivery of energy is performed in synchronization with a given phase in the cardiac cycle. For some applications, the endocardial tissue is observed via an image stream that is stabilized with respect to a given phase of the cardiac cycle, and/or movement and/or actuation of energy delivery of the tool is synchronized to the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Percutaneous myocardial revascularization, such as via creating holes in the heart muscle in a desired pattern and by means of an energy delivery or mechanical penetration tool. For some applications, movement of the tool is performed in synchronization with a given phase of the cardiac cycle. For some applications, the tool is actuated (for example, to deliver energy or drill a hole) in synchronization with a given phase of the cardiac cycle. For some applications, the endocardial tissue is observed via an image stream that is stabilized with respect to a given phase of the subject's cardiac cycle, and/or movement and/or activation of the tool is synchronized with the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Delivering any material or substance, such as, for example, gene therapy or stem cells, to specific locations in the heart muscle. For some applications of the present invention, a substance is injected into the heart muscle in a desired pattern, such as a series of points spread across a surface area. For some applications, movement of the tool is performed in synchronization with a given phase of the cardiac cycle. Alternatively or additionally, delivery of the substance is performed in synchronization with the given phase of the cardiac cycle. For some applications, the endocardial tissue is observed via an image stream that is stabilized with respect to a given phase of the cardiac cycle, and/or movement of the tool and/or delivery of the substance is synchronized with the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Repairing tissue in a cyclically-moving portion of a subject's body, such as in a bypass or a valve or a graft, for example, by clipping, suturing, gluing, and/or another technique. For some applications, movement of the repair tool is performed in synchronization with a selected phase in the cardiac cycle. Alternatively or additionally, the repair (e.g., the suturing) is performed in synchronization with a selected phase in the cardiac cycle. For some applications, the endocardial tissue is observed via an image stream that is stabilized with respect to a given phase of the cardiac cycle, and/or movement of the tool and/or the repair (e.g., the suturing) is synchronized to the given phase, over the course of a plurality of cardiac cycles. Alternatively or additionally, the image stream is stabilized by means of image tracking the observable feature(s) of one or more tools applied in the course of the procedure, in accordance with the techniques described hereinabove.

Trans Thoracic Needle Aspiration (TTNA), such as when a cyclically-moving lesion within the lungs needs to be biopsied. Typically, the techniques described herein facilitate the prevention of penetration of life-critical organs, during such a procedure. For some applications of the present invention, an aspiration needle is led to, and positioned at, a desired anatomical location in the thorax (such as a lung lesion) while both the tool and thoracic anatomy are viewed in an image stream (such as CT images) that is typically stabilized with respect to a given phase of the respiratory and/or cardiac cycle. Alternatively or additionally, the image stream is stabilized by means of image tracking the observable feature(s) of one or more tools applied in the course of the procedure, in accordance with the techniques described hereinabove. Subsequently, aspiration is performed at the desired anatomical location in synchronization with a given phase of the cardiac and/or respiratory cycle, which is typically the phase, with respect to which the image stream was stabilized.

Trans Bronchial Needle Aspiration (TBNA), such as when a cyclically-moving lesion within the lungs needs to be biopsied. Typically, the techniques described herein facilitate the prevention of penetration of life-critical organs, during such a procedure.

Neural stimulation in the brain, its activation being synchronized with an EEG signal.

Attaching or placing a tool at a desired location, on or within a cyclically-moving organ.

Moving or directing a tool to a desired location, on or within a cyclically-moving organ.

It is noted that although section headers are used in various portions of the present patent application, the techniques described with respect to one of the sections are typically applicable in combination with techniques described in others of the sections. The use of headers is simply intended to help the reader.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a portion of a subject's body that assumes a plurality of different shapes, the apparatus comprising:
an image-acquisition device configured to acquire a plurality of image frames of the portion of the subject's body;
a display; and at least one computer processor, configured to:

receive the image frames, designate at least one of the image frames as a first baseline image frame, a shape of the portion in the first baseline image frame being designated as a first baseline shape of the portion, identify the portion within a first non-baseline-shape image frame of the plurality of image frames, the portion not being shaped in the first baseline shape within the first non-baseline-shape image frame, deform the first non-baseline-shape image frame by deforming the shape of the portion in the first non-baseline-shape image frame, such that the shape of the portion becomes more similar to the first baseline shape of the portion than when the portion in the non-baseline-shape image frame is not deformed, form at least a first composite image that is of higher clarity with respect to anatomy of the portion, relative to each of the acquired image frames, by averaging at least the deformed first non-baseline-shape image frame with the first baseline image frame, and drive the display to display the first composite image.

2. The apparatus according to claim 1, wherein the processor is configured to:

designate at least one of the image frames as a second baseline image frame, a shape of the portion in the second baseline image frame being designated as a second baseline shape of the portion, identify the portion within a second non-baseline-shape image frame of the plurality of image frames, the portion not being shaped in the second baseline shape within the second non-baseline-shape image frame, deform the second non-baseline-shape image frame by deforming the shape of the portion in the second non-baseline-shape image frame, such that the shape of the portion becomes more similar to the second baseline shape of the portion than when the portion in the second non-baseline image frame is not deformed, form a second composite image that is of higher clarity with respect to the anatomy of the portion, relative to each of the acquired image frames, by averaging the deformed second non-baseline-shape image frame with the second baseline image frame, and drive the display to display the first and second composite images as an image stream.

3. The apparatus according to claim 1, wherein the portion of subject's body includes a portion of the subject's body that undergoes cyclic motion, wherein the apparatus is for use with a tool that is configured to be inserted into the portion of the subject's body, and wherein the computer processor is further configured to:

determine an extent of movement of the tool with respect to the portion of the body that is due to the cyclic motion of the portion of the body; and in response thereto, generate an output that is indicative of the determined extent of the movement of the tool with respect to the portion of the body.

4. A method for use with a portion of a subject's body that assumes a plurality of different shapes, the method comprising:

using an image acquisition device, acquiring a plurality of image frames of the portion of the subject's body;

using at least one computer processor, designating at least one of the image frames as a first baseline image frame, a shape of the portion in the first baseline image frame being designated as a first baseline shape of the portion;

using the processor, identifying the portion within a first non-baseline-shape image frame of the plurality of image frames, the portion not being shaped in the first baseline shape within the first non-baseline-shape image frame;

using the processor, deforming the first non-baseline-shape image frame by deforming the shape of the portion in the first non-baseline-shape image frame, such that the shape of the portion becomes more similar to the first baseline shape of the portion than when the portion in the non-baseline-shape image frame is not deformed;

using the processor, forming at least a first composite image that is of higher clarity with respect to anatomy of the portion, relative to each of the acquired image frames, by averaging at least the deformed first non-baseline-shape image frame with the first baseline image frame; and using a display, displaying the first composite image.

5. The method according to claim 4, further comprising:

using the processor, designating at least one of the image frames as a second baseline image frame, a shape of the portion in the second baseline image frame being designated as a second baseline shape of the portion;

using the processor, identifying the portion within a second non-baseline-shape image frame of the plurality of image frames, the portion not being shaped in the second baseline shape within the second non-baseline-shape image frame;

using the processor, deforming the second non-baseline-shape image frame by deforming the shape of the portion in the second non-baseline-shape image frame, such that the shape of the portion becomes more similar to the second baseline shape of the portion than when the portion in the second non-baseline image frame is not deformed; and using the processor, forming a second composite image that is of higher clarity with respect to the anatomy of the portion, relative to each of the acquired image frames, by averaging the deformed second non-baseline-shape image frame with the second baseline image frame, wherein displaying the output comprises displaying the first and second composite images as an image stream.

6. The method according to claim 4, wherein the portion of subject's body includes a portion of the subject's body that undergoes cyclic motion, wherein the method is for use with a tool that is configured to be inserted into the portion of the subject's body, and wherein the method further comprises, using at least one computer processor:

determining an extent of movement of the tool with respect to the portion of the body that is due to the cyclic motion of the portion of the body; and in response thereto, generating an output that is indicative of the determined extent of the movement of the tool with respect to the portion of the body.

* * * * *